US010426931B2

(12) United States Patent
Blanchard et al.

(10) Patent No.: US 10,426,931 B2
(45) Date of Patent: *Oct. 1, 2019

(54) CATHETER PLACEMENT DEVICE AND METHOD

(71) Applicant: C. R. Bard, Inc., Murray Hill, NJ (US)

(72) Inventors: Daniel B. Blanchard, Bountiful, UT (US); John W. Hall, North Salt Lake, UT (US); Jason R. Stats, Layton, UT (US); Mark A. Christensen, Salt Lake City, UT (US)

(73) Assignee: C. R. Bard, Inc., Murray Hill, NJ (US)

( * ) Notice: Subject to any disclaimer, the term of this patent is extended or adjusted under 35 U.S.C. 154(b) by 212 days.

This patent is subject to a terminal disclaimer.

(21) Appl. No.: 14/585,800

(22) Filed: Dec. 30, 2014

(65) Prior Publication Data

US 2015/0119806 A1    Apr. 30, 2015

Related U.S. Application Data

(63) Continuation of application No. 13/107,781, filed on May 13, 2011, now Pat. No. 8,932,258.

(Continued)

(51) Int. Cl.
*A61M 25/06* (2006.01)
*A61M 25/00* (2006.01)
(Continued)

(52) U.S. Cl.
CPC .... *A61M 25/0618* (2013.01); *A61M 25/0097* (2013.01); *A61M 25/0102* (2013.01); *A61M 25/0105* (2013.01); *A61M 25/09041* (2013.01)

(58) Field of Classification Search
CPC ...... A61M 25/0618; A61M 25/009041; A61M 25/0097; A61M 25/0105; A61M 25/0102
See application file for complete search history.

(56) References Cited

U.S. PATENT DOCUMENTS

D138,589 S    8/1944  Brandenburg
3,185,151 A   5/1965  Czorny
(Continued)

FOREIGN PATENT DOCUMENTS

AU    710967 B2    9/1999
CN    1178707 A    4/1998
(Continued)

OTHER PUBLICATIONS

Access Scientific, The PICC Wand® Product Data Sheet, Revision F, May 22, 2012.

(Continued)

*Primary Examiner* — Nathan R Price
*Assistant Examiner* — Melissa A Snyder
(74) *Attorney, Agent, or Firm* — Rutan & Tucker, LLP

(57) ABSTRACT

An insertion tool for inserting a catheter into a body of a patient is disclosed. The insertion tool unifies needle insertion, guidewire advancement, and catheter insertion in a single device. In one embodiment, the insertion tool comprises a housing in which at least a portion of the catheter is initially disposed, a hollow needle distally extending from the housing with at least a portion of the catheter pre-disposed over the needle, and a guidewire pre-disposed within the needle. A guidewire advancement assembly is also included for selectively advancing the guidewire distally past a distal end of the needle in preparation for distal advancement of the catheter. In one embodiment a catheter advancement assembly is also included for selectively advancing the catheter into the patient. Each advancement assembly can include a slide or other actuator that enables a user to selectively advance the desired component.

13 Claims, 43 Drawing Sheets

Related U.S. Application Data

(60) Provisional application No. 61/385,844, filed on Sep. 23, 2010, provisional application No. 61/372,050, filed on Aug. 9, 2010, provisional application No. 61/345,005, filed on May 14, 2010, provisional application No. 61/345,022, filed on May 14, 2010, provisional application No. 61/415,248, filed on Nov. 18, 2010.

(51) Int. Cl.
*A61M 25/01* (2006.01)
*A61M 25/09* (2006.01)

(56) References Cited

U.S. PATENT DOCUMENTS

| | | |
|---|---|---|
| 3,297,030 A | 1/1967 | Czorny et al. |
| 3,500,828 A | 3/1970 | Podhora |
| 3,589,361 A | 6/1971 | Loper et al. |
| 3,592,192 A | 7/1971 | Harautuneian |
| 3,682,173 A | 8/1972 | Center |
| 3,921,631 A | 11/1975 | Thompson |
| 3,995,628 A | 12/1976 | Gula et al. |
| 4,079,738 A | 3/1978 | Dunn et al. |
| 4,354,491 A | 10/1982 | Marbry |
| 4,417,886 A | 11/1983 | Frankhouser et al. |
| 4,456,017 A | 6/1984 | Miles |
| 4,581,019 A | 4/1986 | Curelaru et al. |
| D287,877 S | 1/1987 | Holewinski et al. |
| 4,728,322 A | 3/1988 | Walker et al. |
| 4,772,264 A | 9/1988 | Cragg |
| 4,772,267 A | 9/1988 | Brown |
| 4,781,703 A | 11/1988 | Walker et al. |
| 4,792,531 A | 12/1988 | Kakihana |
| 4,826,070 A | 5/1989 | Kakihana |
| 4,828,547 A | 5/1989 | Sahi et al. |
| 4,834,708 A | 5/1989 | Pillari |
| 4,840,613 A | 6/1989 | Balbierz |
| 4,840,622 A | 6/1989 | Hardy |
| 4,846,812 A | 7/1989 | Walker et al. |
| 4,869,259 A | 9/1989 | Elkins |
| D304,079 S | 10/1989 | McFarlane |
| 4,871,358 A | 10/1989 | Gold |
| 4,883,699 A | 11/1989 | Aniuk et al. |
| 4,894,052 A | 1/1990 | Crawford |
| 4,906,956 A | 3/1990 | Kakihana |
| 4,911,691 A | 3/1990 | Aniuk et al. |
| 4,913,704 A | 4/1990 | Kurimoto |
| 4,917,671 A | 4/1990 | Chang |
| 4,955,863 A | 9/1990 | Walker et al. |
| 4,966,586 A | 10/1990 | Vaillancourt |
| 4,994,042 A | 2/1991 | Vadher |
| 4,994,047 A | 2/1991 | Walker et al. |
| 4,995,866 A | 2/1991 | Amplatz et al. |
| 5,007,901 A | 4/1991 | Shields |
| 5,009,642 A | 4/1991 | Sahi |
| 5,019,048 A | 5/1991 | Margolin |
| 5,019,049 A | 5/1991 | Haining |
| D318,733 S | 7/1991 | Wyzgala |
| 5,034,347 A | 7/1991 | Kakihana |
| D321,250 S | 10/1991 | Jepson et al. |
| 5,061,254 A | 10/1991 | Karakelle et al. |
| 5,078,694 A | 1/1992 | Wallace |
| 5,078,696 A | 1/1992 | Nedbaluk |
| 5,093,692 A | 3/1992 | Su et al. |
| 5,098,392 A | 3/1992 | Fleischhacker et al. |
| 5,098,395 A | 3/1992 | Fields |
| 5,108,375 A | 4/1992 | Harrison et al. |
| 5,108,376 A | 4/1992 | Bonaldo |
| 5,112,312 A | 5/1992 | Luther |
| 5,120,317 A | 6/1992 | Luther |
| 5,125,906 A | 6/1992 | Fleck |
| 5,135,487 A | 8/1992 | Morrill et al. |
| 5,137,515 A | 8/1992 | Hogan |
| 5,149,326 A | 9/1992 | Woodgrift et al. |
| 5,156,596 A | 10/1992 | Balbierz et al. |
| 5,158,544 A | 10/1992 | Weinstein |
| 5,186,168 A | 2/1993 | Spofford et al. |
| 5,186,712 A | 2/1993 | Kelso et al. |
| 5,190,528 A | 3/1993 | Fonger et al. |
| 5,192,301 A | 3/1993 | Kamiya et al. |
| 5,195,974 A | 3/1993 | Hardy |
| 5,195,985 A | 3/1993 | Hall |
| 5,215,527 A | 6/1993 | Beck et al. |
| 5,215,528 A | 6/1993 | Purdy et al. |
| 5,217,435 A | 6/1993 | Kring |
| 5,219,335 A | 6/1993 | Willard et al. |
| 5,222,944 A | 6/1993 | Harris |
| 5,225,369 A | 7/1993 | Su et al. |
| 5,226,899 A | 7/1993 | Lee et al. |
| D338,955 S | 8/1993 | Gresl et al. |
| 5,246,426 A | 9/1993 | Lewis et al. |
| 5,257,980 A | 11/1993 | Van Antwerp et al. |
| D345,419 S | 3/1994 | Horrigan et al. |
| 5,297,546 A | 3/1994 | Spofford et al. |
| 5,312,361 A | 5/1994 | Zadini et al. |
| 5,352,205 A | 10/1994 | Dales et al. |
| 5,358,796 A | 10/1994 | Nakamura et al. |
| 5,366,441 A | 11/1994 | Crawford |
| 5,368,661 A | 11/1994 | Nakamura et al. |
| D353,668 S | 12/1994 | Banks et al. |
| 5,380,290 A | 1/1995 | Makower et al. |
| 5,380,292 A | 1/1995 | Wilson |
| 5,395,341 A | 3/1995 | Slater |
| 5,397,311 A | 3/1995 | Walker et al. |
| 5,405,323 A | 4/1995 | Rogers et al. |
| 5,415,177 A | 5/1995 | Zadini et al. |
| 5,415,645 A | 5/1995 | Friend et al. |
| 5,419,766 A | 5/1995 | Chang et al. |
| 5,431,506 A | 7/1995 | Masunaga |
| 5,454,785 A | 10/1995 | Smith |
| 5,458,658 A | 10/1995 | Sircom |
| 5,480,389 A | 1/1996 | McWha et al. |
| 5,482,395 A | 1/1996 | Gasparini |
| 5,484,419 A | 1/1996 | Fleck |
| 5,487,734 A | 1/1996 | Thorne et al. |
| 5,496,281 A | 3/1996 | Krebs |
| 5,507,300 A | 4/1996 | Mukai et al. |
| 5,520,657 A | 5/1996 | Sellers et al. |
| D371,195 S | 6/1996 | Krebs |
| 5,522,807 A | 6/1996 | Luther |
| 5,527,290 A | 6/1996 | Zadini et al. |
| 5,527,291 A | 6/1996 | Zadini et al. |
| 5,531,701 A | 7/1996 | Luther |
| 5,533,988 A | 7/1996 | Dickerson et al. |
| 5,554,136 A | 9/1996 | Luther |
| 5,562,631 A | 10/1996 | Bogert |
| 5,562,633 A | 10/1996 | Wozencroft et al. |
| 5,569,202 A | 10/1996 | Kovalic et al. |
| 5,569,217 A | 10/1996 | Luther |
| 5,591,194 A | 1/1997 | Berthiaume |
| 5,599,291 A | 2/1997 | Balbierz et al. |
| 5,613,663 A | 3/1997 | Schmidt et al. |
| 5,634,475 A | 6/1997 | Wolvek |
| 5,634,913 A | 6/1997 | Stinger |
| 5,651,772 A | 7/1997 | Arnett |
| D383,538 S | 9/1997 | Erskine et al. |
| 5,674,241 A | 10/1997 | Bley et al. |
| 5,676,658 A | 10/1997 | Erskine |
| 5,683,368 A | 11/1997 | Schmidt |
| 5,683,370 A | 11/1997 | Luther et al. |
| 5,685,855 A | 11/1997 | Erskine |
| 5,685,858 A | 11/1997 | Kawand |
| 5,685,860 A | 11/1997 | Chang et al. |
| 5,688,249 A | 11/1997 | Chang et al. |
| 5,702,369 A | 12/1997 | Mercereau |
| 5,704,914 A | 1/1998 | Stocking et al. |
| 5,725,503 A | 3/1998 | Arnett |
| 5,730,150 A | 3/1998 | Peppel et al. |
| 5,730,741 A | 3/1998 | Horzewski et al. |
| 5,738,660 A | 4/1998 | Luther |
| 5,743,882 A | 4/1998 | Luther |
| 5,743,888 A | 4/1998 | Wilkes et al. |
| 5,749,371 A | 5/1998 | Zadini et al. |

(56) References Cited

U.S. PATENT DOCUMENTS

| | | | |
|---|---|---|---|
| 5,755,693 A | 5/1998 | Walker et al. | |
| 5,762,630 A | 6/1998 | Bley et al. | |
| 5,762,636 A | 6/1998 | Rupp et al. | |
| 5,765,682 A | 6/1998 | Bley et al. | |
| 5,782,807 A | 7/1998 | Falvai et al. | |
| 5,800,395 A * | 9/1998 | Botich | A61B 5/1405 604/110 |
| 5,807,342 A | 9/1998 | Musgrave et al. | |
| 5,810,835 A | 9/1998 | Ryan et al. | |
| 5,813,411 A | 9/1998 | Van Bladel et al. | |
| 5,817,069 A | 10/1998 | Arnett | |
| 5,824,001 A | 10/1998 | Erskine | |
| 5,827,202 A | 10/1998 | Miraki et al. | |
| 5,830,224 A | 11/1998 | Cohn et al. | |
| 5,839,470 A | 11/1998 | Hiejima et al. | |
| 5,846,259 A | 12/1998 | Berthiaume | |
| 5,851,196 A | 12/1998 | Arnett | |
| 5,853,393 A | 12/1998 | Bogert | |
| 5,855,615 A | 1/1999 | Bley et al. | |
| 5,879,332 A | 3/1999 | Schwemberger et al. | |
| 5,885,217 A | 3/1999 | Gisselberg et al. | |
| 5,885,251 A | 3/1999 | Luther | |
| 5,891,105 A | 4/1999 | Mahurkar | |
| 5,902,274 A | 5/1999 | Yamamoto et al. | |
| 5,902,832 A | 5/1999 | Van Bladel et al. | |
| 5,913,848 A | 6/1999 | Luther et al. | |
| 5,916,208 A | 6/1999 | Luther et al. | |
| 5,928,199 A | 7/1999 | Nakagami | |
| 5,944,690 A | 8/1999 | Falwell et al. | |
| 5,947,930 A | 9/1999 | Schwemberger et al. | |
| 5,951,520 A | 9/1999 | Burzynski et al. | |
| 5,954,698 A | 9/1999 | Pike | |
| 5,957,893 A | 9/1999 | Luther et al. | |
| 5,964,744 A | 10/1999 | Balbierz et al. | |
| 5,984,895 A | 11/1999 | Padilla et al. | |
| 5,997,510 A | 12/1999 | Schwemberger | |
| 6,004,294 A | 12/1999 | Brimhall et al. | |
| 6,004,295 A | 12/1999 | Langer et al. | |
| 6,011,988 A | 1/2000 | Lynch et al. | |
| 6,022,319 A | 2/2000 | Willard et al. | |
| 6,024,727 A | 2/2000 | Thorne et al. | |
| 6,024,729 A | 2/2000 | Dehdashtian et al. | |
| 6,045,734 A | 4/2000 | Luther et al. | |
| 6,056,726 A | 5/2000 | Isaacson | |
| 6,066,100 A | 5/2000 | Willard et al. | |
| 6,080,137 A | 6/2000 | Pike | |
| 6,096,004 A | 8/2000 | Meglan et al. | |
| 6,120,494 A | 9/2000 | Jonkman | |
| 6,126,641 A | 10/2000 | Shields | |
| 6,139,532 A | 10/2000 | Howell et al. | |
| 6,159,179 A | 12/2000 | Simonson | |
| 6,176,842 B1 | 1/2001 | Tachibana et al. | |
| 6,197,007 B1 | 3/2001 | Thorne et al. | |
| 6,203,527 B1 | 3/2001 | Zadini et al. | |
| 6,213,978 B1 | 4/2001 | Voyten | |
| 6,217,558 B1 | 4/2001 | Zadini et al. | |
| 6,221,049 B1 | 4/2001 | Selmon et al. | |
| 6,224,569 B1 * | 5/2001 | Brimhall | A61M 25/0618 604/164.06 |
| 6,228,062 B1 | 5/2001 | Howell et al. | |
| 6,228,073 B1 | 5/2001 | Noone et al. | |
| 6,268,399 B1 | 7/2001 | Hultine et al. | |
| 6,270,480 B1 | 8/2001 | Dorr et al. | |
| 6,309,379 B1 | 10/2001 | Willard et al. | |
| D452,003 S | 12/2001 | Niermann | |
| 6,336,914 B1 | 1/2002 | Gillespie, III | |
| 6,368,337 B1 | 4/2002 | Kieturakis et al. | |
| 6,379,333 B1 | 4/2002 | Brimhall et al. | |
| D457,955 S | 5/2002 | Bilitz | |
| D460,179 S | 7/2002 | Isoda et al. | |
| 6,422,989 B1 | 7/2002 | Hektner | |
| 6,436,070 B1 | 8/2002 | Botich et al. | |
| 6,451,052 B1 | 9/2002 | Burmeister et al. | |
| 6,461,362 B1 | 10/2002 | Halseth et al. | |
| 6,475,217 B1 | 11/2002 | Platt | |
| 6,478,779 B1 | 11/2002 | Hu | |
| 6,497,681 B1 | 12/2002 | Brenner | |
| 6,524,276 B1 | 2/2003 | Halseth et al. | |
| D471,980 S | 3/2003 | Caizza | |
| 6,527,759 B1 | 3/2003 | Tachibana et al. | |
| 6,540,725 B1 | 4/2003 | Ponzi | |
| 6,540,732 B1 | 4/2003 | Botich et al. | |
| 6,544,239 B2 | 4/2003 | Kinsey et al. | |
| 6,547,762 B1 | 4/2003 | Botich et al. | |
| 6,558,355 B1 | 5/2003 | Metzger et al. | |
| 6,582,402 B1 | 6/2003 | Erskine | |
| 6,585,703 B1 | 7/2003 | Kassel et al. | |
| 6,589,262 B1 | 7/2003 | Honebrink et al. | |
| 6,595,955 B2 | 7/2003 | Ferguson et al. | |
| 6,607,511 B2 | 8/2003 | Halseth et al. | |
| 6,620,136 B1 | 9/2003 | Pressly, Sr. et al. | |
| 6,626,869 B1 | 9/2003 | Bint | |
| 6,632,201 B1 | 10/2003 | Mathias et al. | |
| 6,638,252 B2 | 10/2003 | Moulton et al. | |
| 6,641,564 B1 | 11/2003 | Kraus | |
| 6,645,178 B1 | 11/2003 | Junker et al. | |
| 6,652,490 B2 | 11/2003 | Howell | |
| 6,663,577 B2 | 12/2003 | Jen et al. | |
| 6,663,592 B2 | 12/2003 | Rhad et al. | |
| 6,666,865 B2 | 12/2003 | Platt | |
| 6,679,900 B2 | 1/2004 | Kieturakis et al. | |
| 6,695,856 B2 | 2/2004 | Kieturakis et al. | |
| 6,695,860 B1 | 2/2004 | Ward et al. | |
| 6,712,790 B1 | 3/2004 | Prestidge et al. | |
| 6,716,197 B2 | 4/2004 | Svendsen | |
| 6,749,588 B1 | 6/2004 | Howell et al. | |
| 6,764,468 B1 | 7/2004 | East | |
| D494,270 S | 8/2004 | Reschke | |
| 6,796,962 B2 | 9/2004 | Ferguson et al. | |
| 6,860,871 B2 | 3/2005 | Kuracina et al. | |
| 6,902,546 B2 | 6/2005 | Ferguson | |
| 6,913,595 B2 | 7/2005 | Mastorakis | |
| 6,916,311 B2 | 7/2005 | Vojtasek | |
| 6,953,448 B2 | 10/2005 | Moulton et al. | |
| 6,960,191 B2 | 11/2005 | Howlett et al. | |
| 6,972,002 B2 | 12/2005 | Thorne | |
| 6,974,438 B2 | 12/2005 | Shekalim | |
| 6,994,693 B2 | 2/2006 | Tal | |
| 7,001,396 B2 | 2/2006 | Glazier et al. | |
| 7,004,927 B2 | 2/2006 | Ferguson et al. | |
| 7,018,390 B2 | 3/2006 | Turovskiy et al. | |
| 7,025,746 B2 | 4/2006 | Tal | |
| 7,090,656 B1 | 8/2006 | Botich et al. | |
| 7,097,633 B2 | 8/2006 | Botich et al. | |
| 7,125,396 B2 | 10/2006 | Leinsing et al. | |
| 7,141,040 B2 | 11/2006 | Lichtenberg | |
| 7,153,276 B2 | 12/2006 | Barker et al. | |
| 7,179,244 B2 | 2/2007 | Smith et al. | |
| 7,191,900 B2 | 3/2007 | Opie et al. | |
| 7,192,433 B2 | 3/2007 | Osypka et al. | |
| 7,303,548 B2 | 12/2007 | Rhad et al. | |
| 7,354,422 B2 | 4/2008 | Riesenberger et al. | |
| 7,413,562 B2 | 8/2008 | Ferguson et al. | |
| 7,422,572 B2 | 9/2008 | Popov et al. | |
| 7,458,954 B2 | 12/2008 | Ferguson et al. | |
| 7,465,294 B1 | 12/2008 | Vladimirsky | |
| 7,491,176 B2 | 2/2009 | Mann | |
| 7,494,010 B2 | 2/2009 | Opie et al. | |
| 7,513,887 B2 | 4/2009 | Halseth et al. | |
| 7,530,965 B2 | 5/2009 | Villa et al. | |
| 7,566,323 B2 | 7/2009 | Chang | |
| D601,243 S | 9/2009 | Bierman et al. | |
| D604,839 S | 11/2009 | Crawford et al. | |
| 7,611,485 B2 | 11/2009 | Ferguson | |
| 7,618,395 B2 | 11/2009 | Ferguson | |
| 7,645,263 B2 | 1/2010 | Angel et al. | |
| 7,654,988 B2 | 2/2010 | Moulton et al. | |
| 7,658,725 B2 | 2/2010 | Bialecki et al. | |
| D612,043 S | 3/2010 | Young et al. | |
| 7,682,358 B2 | 3/2010 | Gullickson et al. | |
| D615,197 S | 5/2010 | Koh et al. | |
| 7,713,243 B2 | 5/2010 | Hillman | |
| 7,722,567 B2 | 5/2010 | Tal | |
| D617,893 S | 6/2010 | Bierman et al. | |

(56) References Cited

U.S. PATENT DOCUMENTS

| | | |
|---|---|---|
| 7,736,332 B2 | 6/2010 | Carlyon et al. |
| 7,736,339 B2 | 6/2010 | Woehr et al. |
| 7,753,887 B2 | 7/2010 | Botich et al. |
| 7,762,993 B2 | 7/2010 | Perez |
| 7,766,879 B2 | 8/2010 | Tan et al. |
| 7,798,994 B2 | 9/2010 | Brimhall |
| 7,828,773 B2 | 11/2010 | Swisher et al. |
| 7,828,774 B2 | 11/2010 | Harding et al. |
| D634,843 S | 3/2011 | Kim et al. |
| 7,905,857 B2 | 3/2011 | Swisher |
| 7,922,696 B2 | 4/2011 | Tal et al. |
| 7,922,698 B2 | 4/2011 | Riesenberger et al. |
| 7,935,080 B2 | 5/2011 | Howell et al. |
| 8,029,472 B2 | 10/2011 | Leinsing et al. |
| D653,329 S | 1/2012 | Lee-Sepsick |
| D667,111 S | 9/2012 | Robinson |
| 8,273,054 B2 | 9/2012 | St. Germain et al. |
| D672,456 S | 12/2012 | Lee-Sepsick |
| 8,337,424 B2 | 12/2012 | Palmer et al. |
| 8,337,471 B2 | 12/2012 | Baid |
| D675,318 S | 1/2013 | Luk et al. |
| D687,548 S | 8/2013 | Hayashi |
| D700,318 S | 2/2014 | Amoah et al. |
| 8,679,063 B2 | 3/2014 | Stout et al. |
| 8,721,546 B2 * | 5/2014 | Belson .............. A61M 25/0105 600/371 |
| D710,495 S | 8/2014 | Wu et al. |
| D713,957 S | 9/2014 | Woehr et al. |
| D714,436 S | 9/2014 | Lee-Sepsick |
| D715,931 S | 10/2014 | Watanabe et al. |
| 8,932,258 B2 | 1/2015 | Blanchard et al. |
| D726,908 S | 4/2015 | Yu et al. |
| 8,998,852 B2 | 4/2015 | Blanchard et al. |
| D728,781 S | 5/2015 | Pierson et al. |
| D733,289 S | 6/2015 | Blanchard et al. |
| D735,321 S | 7/2015 | Blanchard |
| 9,095,683 B2 | 8/2015 | Hall et al. |
| D740,410 S | 10/2015 | Korkuch et al. |
| D746,445 S | 12/2015 | Lazarus |
| D748,254 S | 1/2016 | Freigang et al. |
| 9,227,038 B2 | 1/2016 | Woehr |
| D748,774 S | 2/2016 | Caron |
| D748,777 S | 2/2016 | Uenishi et al. |
| D749,214 S | 2/2016 | Uenishi et al. |
| D749,727 S | 2/2016 | Wapler et al. |
| D751,194 S | 3/2016 | Yu et al. |
| D752,737 S | 3/2016 | Ohashi |
| D755,368 S | 5/2016 | Efinger et al. |
| 9,522,254 B2 | 12/2016 | Belson |
| 9,616,201 B2 | 4/2017 | Belson |
| 9,675,784 B2 | 6/2017 | Belson |
| 9,757,540 B2 | 9/2017 | Belson |
| 9,861,792 B2 | 1/2018 | Hall et al. |
| 9,872,971 B2 | 1/2018 | Blanchard |
| 9,950,139 B2 | 4/2018 | Blanchard et al. |
| 10,232,146 B2 | 3/2019 | Braithwaite et al. |
| 2002/0103446 A1 | 8/2002 | McFann et al. |
| 2002/0177812 A1 | 11/2002 | Moulton et al. |
| 2003/0032922 A1 | 2/2003 | Moorehead |
| 2003/0032936 A1 | 2/2003 | Lederman |
| 2003/0153874 A1 | 8/2003 | Tal |
| 2003/0187396 A1 | 10/2003 | Ponzi |
| 2004/0019329 A1 | 1/2004 | Erskine |
| 2004/0044302 A1 | 3/2004 | Bernard et al. |
| 2004/0092879 A1 | 5/2004 | Kraus et al. |
| 2004/0111059 A1 | 6/2004 | Howlett et al. |
| 2004/0122373 A1 | 6/2004 | Botich et al. |
| 2004/0176758 A1 | 9/2004 | Yassinzadeh |
| 2004/0215146 A1 | 10/2004 | Lampropoulos et al. |
| 2004/0236288 A1 | 11/2004 | Howell et al. |
| 2005/0004524 A1 | 1/2005 | Newby et al. |
| 2005/0020940 A1 | 1/2005 | Opie et al. |
| 2005/0027256 A1 | 2/2005 | Barker et al. |
| 2005/0040061 A1 | 2/2005 | Opie et al. |
| 2005/0075606 A1 | 4/2005 | Botich et al. |
| 2005/0197623 A1 | 9/2005 | Leeflang et al. |
| 2005/0245847 A1 | 11/2005 | Schaeffer |
| 2005/0256505 A1 | 11/2005 | Long et al. |
| 2005/0273057 A1 | 12/2005 | Popov |
| 2006/0025721 A1 | 2/2006 | Duffy et al. |
| 2006/0079787 A1 | 4/2006 | Whiting et al. |
| 2006/0084964 A1 | 4/2006 | Knudson et al. |
| 2006/0155245 A1 * | 7/2006 | Woehr .............. A61M 25/0618 604/164.08 |
| 2006/0167405 A1 | 7/2006 | King et al. |
| 2006/0229563 A1 | 10/2006 | O'Reagan et al. |
| 2006/0264834 A1 | 11/2006 | Vaillancourt |
| 2007/0043422 A1 | 2/2007 | Shmulewitz et al. |
| 2007/0060999 A1 | 3/2007 | Randall et al. |
| 2007/0083188 A1 | 4/2007 | Grandt et al. |
| 2007/0100284 A1 | 5/2007 | Leinsing et al. |
| 2007/0123803 A1 | 5/2007 | Fujiwara et al. |
| 2007/0191777 A1 | 8/2007 | King |
| 2007/0193903 A1 | 8/2007 | Opie et al. |
| 2007/0233007 A1 | 10/2007 | Adams |
| 2007/0244438 A1 | 10/2007 | Perez |
| 2007/0276288 A1 | 11/2007 | Khaw |
| 2008/0108911 A1 | 5/2008 | Palmer |
| 2008/0108944 A1 | 5/2008 | Woehr et al. |
| 2008/0125709 A1 | 5/2008 | Chang et al. |
| 2008/0131300 A1 | 6/2008 | Junod et al. |
| 2008/0243165 A1 | 10/2008 | Mauch et al. |
| 2008/0262430 A1 * | 10/2008 | Anderson .......... A61B 17/3415 604/164.1 |
| 2008/0262431 A1 | 10/2008 | Anderson et al. |
| 2008/0294111 A1 | 11/2008 | Tal et al. |
| 2008/0300574 A1 | 12/2008 | Belson et al. |
| 2009/0030380 A1 | 1/2009 | Binmoeller |
| 2009/0036836 A1 | 2/2009 | Nystrom et al. |
| 2009/0048566 A1 | 2/2009 | Ferguson et al. |
| 2009/0131872 A1 | 5/2009 | Popov |
| 2009/0221961 A1 | 9/2009 | Tal et al. |
| 2009/0292243 A1 | 11/2009 | Harding et al. |
| 2009/0299291 A1 | 12/2009 | Baid |
| 2010/0010447 A1 | 1/2010 | Luther et al. |
| 2010/0036331 A1 | 2/2010 | Sen |
| 2010/0056910 A1 | 3/2010 | Yanuma |
| 2010/0087787 A1 | 4/2010 | Woehr et al. |
| 2010/0094310 A1 | 4/2010 | Warring et al. |
| 2010/0168674 A1 | 7/2010 | Shaw et al. |
| 2010/0204654 A1 | 8/2010 | Mulholland et al. |
| 2010/0204675 A1 | 8/2010 | Woehr et al. |
| 2010/0210934 A1 | 8/2010 | Belson |
| 2010/0246707 A1 | 9/2010 | Michelitsch |
| 2010/0331732 A1 | 12/2010 | Raulerson et al. |
| 2011/0009827 A1 | 1/2011 | Bierman et al. |
| 2011/0015573 A1 | 1/2011 | Maan et al. |
| 2011/0021994 A1 | 1/2011 | Anderson et al. |
| 2011/0137252 A1 | 6/2011 | Oster et al. |
| 2011/0251559 A1 | 10/2011 | Tal et al. |
| 2011/0282285 A1 | 11/2011 | Blanchard et al. |
| 2011/0288482 A1 | 11/2011 | Farrell et al. |
| 2011/0306933 A1 | 12/2011 | Djordjevic et al. |
| 2012/0078231 A1 | 3/2012 | Hoshinouchi |
| 2012/0101440 A1 | 4/2012 | Kamen et al. |
| 2012/0123332 A1 | 5/2012 | Erskine |
| 2012/0184896 A1 | 7/2012 | DeLegge et al. |
| 2012/0197200 A1 | 8/2012 | Belson |
| 2012/0220942 A1 | 8/2012 | Hall et al. |
| 2012/0220956 A1 | 8/2012 | Kuracina et al. |
| 2013/0304030 A1 | 11/2013 | Gray et al. |
| 2014/0031752 A1 | 1/2014 | Blanchard et al. |
| 2014/0088509 A1 | 3/2014 | Sonderegger et al. |
| 2014/0094774 A1 | 4/2014 | Blanchard |
| 2014/0188003 A1 | 7/2014 | Belson |
| 2014/0236099 A1 | 8/2014 | Nakagami et al. |
| 2014/0378867 A1 | 12/2014 | Belson |
| 2015/0231364 A1 | 8/2015 | Blanchard et al. |
| 2015/0290431 A1 | 10/2015 | Hall et al. |
| 2016/0256667 A1 | 9/2016 | Ribelin et al. |
| 2016/0331938 A1 | 11/2016 | Blanchard et al. |
| 2017/0035992 A1 | 2/2017 | Harding et al. |
| 2017/0087338 A1 | 3/2017 | Belson |
| 2017/0209668 A1 | 7/2017 | Belson |

(56) References Cited

U.S. PATENT DOCUMENTS

| | | | |
|---|---|---|---|
| 2017/0259036 | A1 | 9/2017 | Belson |
| 2017/0361071 | A1 | 12/2017 | Belson |
| 2018/0028780 | A1 | 2/2018 | Blanchard et al. |
| 2018/0126125 | A1 | 5/2018 | Hall et al. |
| 2018/0133437 | A1 | 5/2018 | Blanchard |
| 2019/0022358 | A1 | 1/2019 | Belson |

FOREIGN PATENT DOCUMENTS

| | | | |
|---|---|---|---|
| CN | 1319023 | A | 10/2001 |
| CN | 1523970 | | 8/2004 |
| CN | 1871043 | A | 11/2006 |
| CN | 101242868 | A | 8/2008 |
| CN | 101417159 | A | 4/2009 |
| CN | 101784300 | A | 7/2010 |
| CN | 102099075 | A | 6/2011 |
| CN | 102939129 | A | 2/2013 |
| CN | 105073174 | A | 11/2015 |
| CN | 105188826 | A | 12/2015 |
| CN | 105705191 | A | 6/2016 |
| EP | 0314470 | A2 | 5/1989 |
| EP | 747075 | A2 | 12/1996 |
| EP | 832663 | A2 | 4/1998 |
| EP | 2569046 | A1 | 3/2013 |
| JP | 2003-159334 | A | 6/2003 |
| JP | 2004-130074 | A | 4/2004 |
| JP | 2009-500129 | A | 1/2009 |
| JP | 2010-088521 | A | 4/2010 |
| JP | 2013-529111 | | 7/2013 |
| JP | 2018-118079 | A | 8/2018 |
| WO | 9511710 | A1 | 5/1995 |
| WO | 0012167 | A1 | 3/2000 |
| WO | 0107103 | A1 | 2/2001 |
| WO | 01/26725 | A1 | 4/2001 |
| WO | 0241932 | A2 | 5/2002 |
| WO | 02/066093 | A2 | 8/2002 |
| WO | 2004106203 | A2 | 12/2004 |
| WO | 2005002659 | A1 | 1/2005 |
| WO | 2006062996 | A2 | 6/2006 |
| WO | 2007006055 | A2 | 1/2007 |
| WO | 2007/032343 | A1 | 3/2007 |
| WO | 2008030999 | A2 | 3/2008 |
| WO | 2008/131300 | A2 | 10/2008 |
| WO | 2009/001309 | A1 | 12/2008 |
| WO | 2009031161 | A1 | 3/2009 |
| WO | 2009114837 | A2 | 9/2009 |
| WO | 2009/124990 | A1 | 10/2009 |
| WO | 2010015676 | A1 | 2/2010 |
| WO | 2010/048449 | A2 | 4/2010 |
| WO | 2010/132608 | A2 | 11/2010 |
| WO | 2011036574 | A1 | 3/2011 |
| WO | 2011143621 | A1 | 11/2011 |
| WO | 2012154277 | A1 | 11/2012 |
| WO | 2014133617 | A1 | 9/2014 |
| WO | 2015/168655 | A2 | 11/2015 |
| WO | 2016/037127 | A1 | 3/2016 |

OTHER PUBLICATIONS

BD Angiocath™ Autoguard™ Shielded IV Catheter Brochure, © 2001.
BD Saf-T-Intima™ Integrated Safety IV Catheter Brochure, © 2001.
Becton Dickinson, Insyte® AutoGuard™ Shielded I.V. Catheter Brochure, 1998.
CN 201180029526.7 filed Dec. 14, 2012 First Office Action dated Apr. 21, 2014.
Hadaway, Lynn C., A Midline Alternative to Central and Peripheral Venous Access, Caring Magazine, May 1990, pp. 45-50.
Menlo Care, Landmark™ Aquavene® Catheters Brochure, 1992.
Menlo Care, Landmark® Midline Catheters Brochure, 1991.
Menlo Care, Publications on Aquavene® Technology, Aug. 1992.
PCT/US2011/036530 filed May 13, 2011 International Search Report dated Oct. 6, 2011.
PCT/US2011/036530 filed May 13, 2011 Written Opinion of the International Searching Authority dated Oct. 6, 2011.
PCT/US2012/026618 International Preliminary Report on Patentability dated Aug. 27, 2013.
PCT/US2012/026618 International Search Report and Written Opinion dated Jun. 25, 2012.
PCT/US2013/073577 filed Dec. 6, 2013 International Search Report and Written Opinion dated Feb. 24, 2014.
PR Newswire, Luther Medical Products, Inc. Receives Approval to Supply Improved Neonatal Product to Japan, Aug. 20, 1998.
Rasor, Julia S, Review of Catheter-related infection rates: comparison of conventional catheter materials with Aquavene®, JVAN vol. 1, No. 3, Spring 1991.
U.S. Appl. No. 13/107,781, filed May 13, 2011 Final Office Action dated Jul. 18, 2014.
U.S. Appl. No. 13/107,781, filed May 13, 2011 Non-Final Office Action dated Dec. 30, 2013.
U.S. Appl. No. 13/405,096, filed Feb. 24, 2012 Advisory Action dated Apr. 18, 2014.
U.S. Appl. No. 13/405,096, filed Feb. 24, 2012 Final Office Action dated Jan. 31, 2014.
U.S. Appl. No. 13/405,096, filed Feb. 24, 2012 Non-Final Office Action dated Aug. 20, 2013.
U.S. Appl. No. 13/405,096, filed Feb. 24, 2012 Non-Final Office Action dated Nov. 18, 2014.
U.S. Appl. No. 14/044,623, filed Oct. 2, 2013 Notice of Allowance dated Nov. 6, 2014.
Waltimire, B. and Rasor, J.S., Midline catheter: Virtually bloodless insertion technique and needle safety tube minimize potential for transmission of bloodborne disease. Sponsored by national Foundation for Infectious Diseases. 5th National forum on AIDS, Hepatitis, and other blood-borne diseases. Atlanta, GA, Mar. 1992.
CN 2012800008866.6 filed Aug. 14, 2013 Second Office Action dated Aug. 17, 2015.
European search report and opinion dated Dec. 1, 2010 for EP Application No. 10075422.5.
International search report and written opinion dated Jan. 16, 2009 for PCT/US2008/062954.
International search report and written opinion dated Apr. 14, 2014 for PCT Application No. US2014/013557.
Notice of allowance dated Jan. 16, 2014 for U.S. Appl. No. 12/598,053.
Notice of allowance dated Feb. 17, 2015 for U.S. Appl. No. 14/477,717.
Office action dated May 8, 2013 for U.S. Appl. No. 12/598,053.
Office action dated Aug. 28, 2013 for U.S. Appl. No. 12/598,053.
Office action dated Oct. 24, 2013 for U.S. Appl. No. 12/598,053.
Office action dated Dec. 4, 2012 for U.S. Appl. No. 12/598,053.
Office action dated Dec. 18, 2014 for U.S. Appl. No. 14/477,717.
EP 12782187.4 filed Sep. 10, 2013 European search report and written opinion dated Dec. 17, 2015.
International search report and written opinion dated Apr. 2, 2012 for PCT/US2012/023192.
Office action dated Mar. 27, 2013 for U.S. Appl. No. 13/358,099.
PCT/US15/28950 filed May 1, 2015 International Search Report and Written Opinion dated Oct. 19, 2015.
PCT/US2015/048676 filed Sep. 4, 2015 International search report and written opinion dated Dec. 4, 2015.
U.S. Appl. No. 14/174,071, filed Feb. 6, 2014 Non-Final Office Action dated Mar. 31, 2016.
Access Scientific, The Powerwand® Extended Dwell Catheter Brochure (http://accessscientific.com/media/4Fr-POWERWAND-Brochure.pdf) last accessed Sep. 25, 2015.
BD Medical Systems, I.V. Catheter Family Brochure (2006).
Menlo Care, Landmark® Midline Catheter Maintenance and Reference Guide (1993).
Menlo Care, Landmark® Venous Access Device Insertion Instructions (1992).
U.S. Appl. No. 14/099,050, filed Dec. 6, 2013 Non-Final Office Action dated Dec. 22, 2015.

(56) References Cited

OTHER PUBLICATIONS

U.S. Appl. No. 14/167,149, filed Jan. 29, 2014 Non-Final Office Action dated Oct. 21, 2015.
U.S. Appl. No. 14/174,071, filed Feb. 6, 2014 Restriction Requirement dated Dec. 7, 2014.
CN 201280008866.6 filed Aug. 14, 2013 Third Office Action dated Jan. 25, 2016.
JP 2013-510353 filed Oct. 31, 2012 Second Office Action dated Jan. 28, 2016.
U.S. Appl. No. 14/099,050, filed Dec. 6, 2013 Non-Final Office Action dated Jul. 19, 2016.
U.S. Appl. No. 14/167,149, filed Jan. 29, 2014 Notice of Allowance dated Jul. 6, 2016.
U.S. Appl. No. 14/192,541, filed Feb. 27, 2014 Non-Final Office Action dated Jul. 20, 2016.
CN 2012800008866.6 filed Aug. 14, 2013 First Office Action dated Dec. 31, 2014.
JP 2013-510353 filed Oct. 31, 2012 First Office Action dated Feb. 19, 2015.
U.S. Appl. No. 13/405,096, filed Feb. 24, 2012 Notice of Allowance dated Mar. 11, 2015.
EP 12782187.4 filed Sep. 10, 2013 European search report and written opinion dated Aug. 30, 2016.
EP 13876666.2 filed Sep. 7, 2015 Extended European Search Report dated Sep. 20, 2016.
JP 2016-107046 filed May 30, 2016 Office Action dated Jul. 28, 2016.
U.S. Appl. No. 14/174,071, filed Feb. 6, 2014 Non-Final Office Action dated Jul. 29, 2016.
U.S. Appl. No. 14/866,441, filed Sep. 25, 2015 Final Office Action dated Sep. 23, 2016.
U.S. Appl. No. 14/866,738, filed Sep. 25, 2015 Non-Final Office Action dated Oct. 31, 2016.
CN 201510079782.7 filed Feb. 13, 2015 Office Action dated Dec. 30, 2016.
JP 2013-510353 filed Oct. 31, 2012 Office Action dated Dec. 15, 2016.
PCT/US2016/032449 filed May 13, 2016 International Search Report and Written Opinion dated Oct. 5, 2016.
PCT/US2016/032534 filed May 13, 2016 International Search Report and Written Opinion dated Oct. 5, 2016.
U.S. Appl. No. 14/099,050, filed Dec. 6, 2013 Final Office Action dated Jan. 30, 2017.
U.S. Appl. No. 14/174,071, filed Feb. 6, 2014 Final Office Action dated Dec. 2, 2016.
U.S. Appl. No. 14/192,541, filed Feb. 27, 2014 Notice of Allowance dated Dec. 6, 2016.
U.S. Appl. No. 14/250,093, filed Apr. 10, 2014 Non-Final Office Action dated Nov. 16, 2016.
U.S. Appl. No. 14/866,441, filed Sep. 25, 2015 Advisory Action dated Dec. 22, 2016.
CN 201480019467.9 filed Sep. 29, 2015 Office Action dated Apr. 6, 2017.
U.S. Appl. No. 14/192,541, filed Feb. 27, 2014 Notice of Corrected Allowability dated Mar. 8, 2017.
U.S. Appl. No. 14/250,093, filed Apr. 10, 2014 Final Office Action dated Mar. 9, 2017.
U.S. Appl. No. 14/750,658, filed Jun. 25, 2016 Non-Final Office Action dated Mar. 9, 2017.
U.S. Appl. No. 14/866,441, filed Sep. 25, 2015 Final Office Action dated Apr. 7, 2017.
U.S. Appl. No. 14/866,738, filed Sep. 25, 2015 Final Office Action dated Feb. 24, 2017.
U.S. Appl. No. 14/876,735, filed Oct. 6, 2015 Non-Final Office Action dated Mar. 30, 2017.
CA 2,799,360 filed May 13, 2011 Office Action dated Jun. 7, 2017.
JP 2016-107046 filed May 30, 2016 Office Action dated Apr. 26, 2017.
U.S. Appl. No. 14/099,050 filed Dec. 6, 2013 Advisory Action dated Jun. 1, 2017.
U.S. Appl. No. 14/250,093 filed Apr. 10, 2014 Advisory Action dated May 19, 2017.
U.S. Appl. No. 14/250,093 filed Apr. 10, 2014 Panel Decision dated Jul. 14, 2017.
U.S. Appl. No. 14/702,580 filed May 1, 2015 Non-Final Office Action dated May 3, 2017.
U.S. Appl. No. 14/750,658 filed Jun. 25, 2016 Notice of Allowance dated Jul. 20, 2017.
U.S. Appl. No. 14/866,738 filed Sep. 25, 2015 Notice of Panel Decision dated Jun. 23, 2017.
CN 201380073657.4 filed Aug. 21, 2015 Office Action dated Mar. 2, 2018.
CN 201510079782.7 filed Feb. 13, 2015 Office Action dated Feb. 5, 2018.
EP 07783404.2 filed Jan. 19, 2009 Office Action dated Mar. 7, 2018.
EP 12782187.4 filed Sep. 10, 2013 Office Action dated Apr. 24, 2018.
RU 2017141812 filed Nov. 30, 2017 Office Action dated Jan. 31, 2018.
U.S. Appl. No. 14/846,387 filed Sep. 4, 2015 Final Office Action dated Mar. 22, 2018.
U.S. Appl. No. 15/154,808 filed May 13, 2016 Non-Final Office Action dated Apr. 6, 2018.
U.S. Appl. No. 15/692,915 filed Aug. 31, 2017 Non-Final Office Action dated Jan. 29, 2018.
U.S. Appl. No. 29/536,043 filed Aug. 12, 2015 Final Office Action dated Mar. 26, 2018.
U.S. Appl. No. 29/545,436 filed Nov. 12, 2015 Final Office Action dated Mar. 26, 2018.
EP 11781384.0 filed Sep. 21, 2012 Extended European Search Report dated Oct. 31, 2017.
EP 15785819.2 filed Dec. 2, 2016 Extended European Search Report dated Dec. 4, 2017.
JP 2016-107046 filed May 30, 2016 Office Action dated Nov. 7, 2017.
PCT/CN2017/075370 filed Mar. 1, 2017 International Search Report and Written Opinion dated Nov. 30, 2017.
U.S. Appl. No. 14/250,093 filed Apr. 10, 2014 Final Office Action dated Nov. 6, 2017.
U.S. Appl. No. 14/702,580 filed May 1, 2015 Advisory Action dated Nov. 13, 2017.
U.S. Appl. No. 14/702,580 filed May 1, 2015 Notice of Allowance dated Dec. 8, 2017.
U.S. Appl. No. 14/866,738 filed Sep. 25, 2015 Non-Final Office Action dated Nov. 6, 2017.
U.S. Appl. No. 15/154,808 filed May 13, 2016 Restriction Requirement dated Jan. 3, 2018.
CN 201380073657.4 filed Aug. 21, 2015 Office Action dated Jun. 28, 2017.
CN 201510079782.7 filed Feb. 13, 2015 Office Action dated Sep. 19, 2017.
JP 2015-560173 filed Aug. 28, 2015 Office Action dated Sep. 19, 2017.
U.S. Appl. No. 14/099,050 filed Dec. 6, 2013 Notice of Allowance dated Sep. 14, 2017.
U.S. Appl. No. 14/099,050 filed Dec. 6, 2013 Notice of Panel Decision dated Aug. 1, 2017.
U.S. Appl. No. 14/702,580 filed May 1, 2015 Final Office Action dated Sep. 1, 2017.
U.S. Appl. No. 14/846,387 filed Sep. 4, 2015 Non-Final Office Action dated Sep. 22, 2017.
U.S. Appl. No. 29/536,043 filed Aug. 12, 2015 Non-Final Office Action dated Aug. 31, 2017.
U.S. Appl. No. 29/545,436 filed Nov. 12, 2015 Non-Final Office Action dated Sep. 12, 2017.
EP 12782187.4 filed Sep. 10, 2013 Office Action dated Nov. 28, 2018.
SG 11201709185X filed Nov. 8, 2017 Office Action dated Oct. 5, 2018.
SG 11201709193S filed Nov. 8, 2017 Office Action dated Oct. 5, 2018.
U.S. Appl. No. 14/846,387 filed Sep. 4, 2015 Notice of Allowance dated Oct. 29, 2018.

(56) References Cited

OTHER PUBLICATIONS

U.S. Appl. No. 14/866,441 filed Sep. 25, 2015 Notice of Allowance dated Oct. 17, 2018.
U.S. Appl. No. 15/154,808 filed May 13, 2016 Advisory Action dated Oct. 26, 2018.
U.S. Appl. No. 15/377,880 filed Dec. 13, 2016 Final Office Action dated Oct. 19, 2018.
U.S. Appl. No. 15/702,537 filed Sep. 12, 2017 Non-Final Office Action dated Nov. 29, 2018.
EP 16797029.2 filed Nov. 21, 2017 Extended European Search Report dated May 3, 2018.
U.S. Appl. No. 14/250,093 filed Apr. 10, 2014 Examiner's Answer dated Jun. 20, 2018.
U.S. Appl. No. 14/846,387 filed Sep. 4, 2015 Advisory Action dated May 10, 2018.
U.S. Appl. No. 14/866,441 filed Sep. 25, 2015 Final Office Action dated Jun. 5, 2018.
U.S. Appl. No. 15/377,880 filed Dec. 13, 2016 Non-Final Office Action dated May 14, 2018.
U.S. Appl. No. 15/481,773 filed Apr. 7, 2017 Non-Final Office Action dated Jun. 29, 2018.
EP 16797047.4 filed Dec. 6, 2017 Supplemental European Search Report dated Jan. 9, 2019.
JP 2016-563441 filed Oct. 19, 2016 Office Action dated Jan. 25, 2019.
U.S. Appl. No. 15/154,384 filed May 13, 2016 Restriction Requirment dated Jan. 25, 2019.
U.S. Appl. No. 15/481,773 filed Apr. 7, 2017 Final Office Action dated Jan. 10, 2019.
U.S. Appl. No. 15/702,537 filed Sep. 12, 2017 Final Office Action dated Mar. 8, 2019.
EP 07783404.2 filed Jan. 19, 2009 Office Action dated Apr. 16, 2019.
JP 2018-039302 filed Mar. 6, 2018 Office Action dated Feb. 20, 2019.
U.S. Appl. No. 15/154,808 filed May 13, 2016 Notice of Allowance dated Apr. 16, 2019.

* cited by examiner

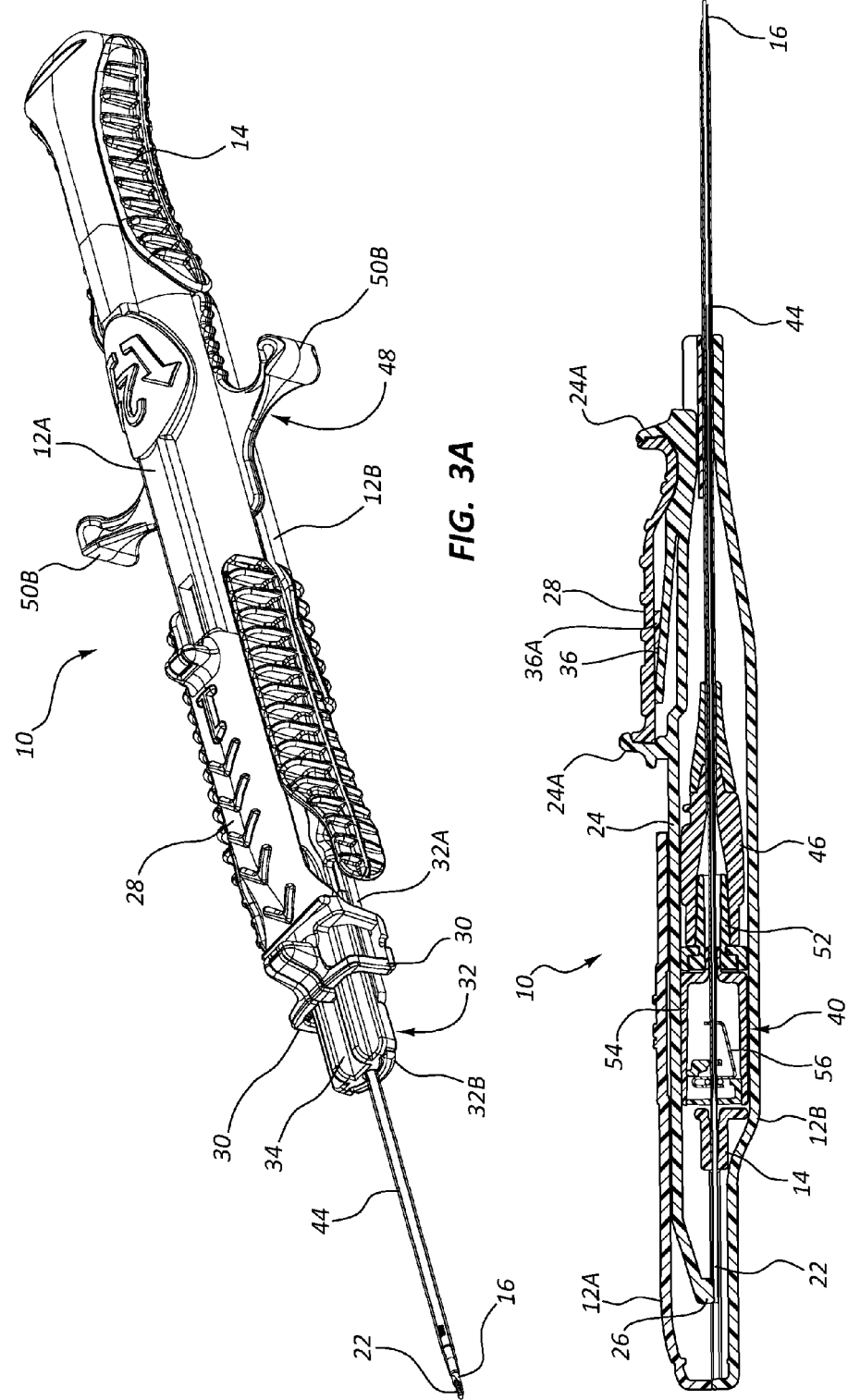

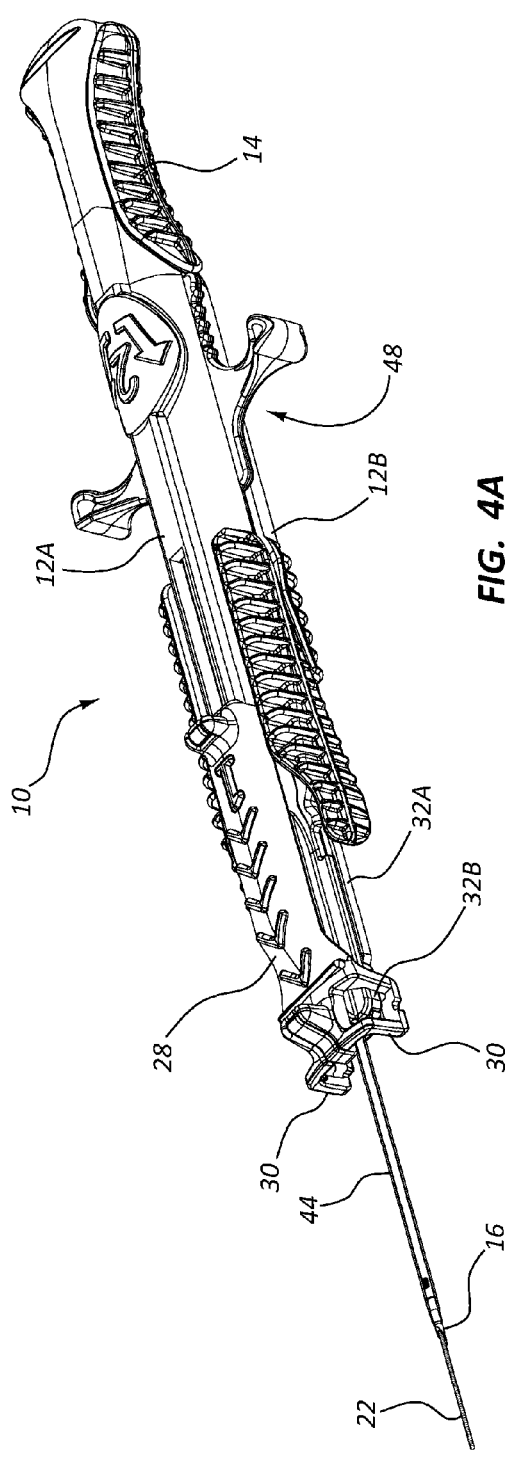
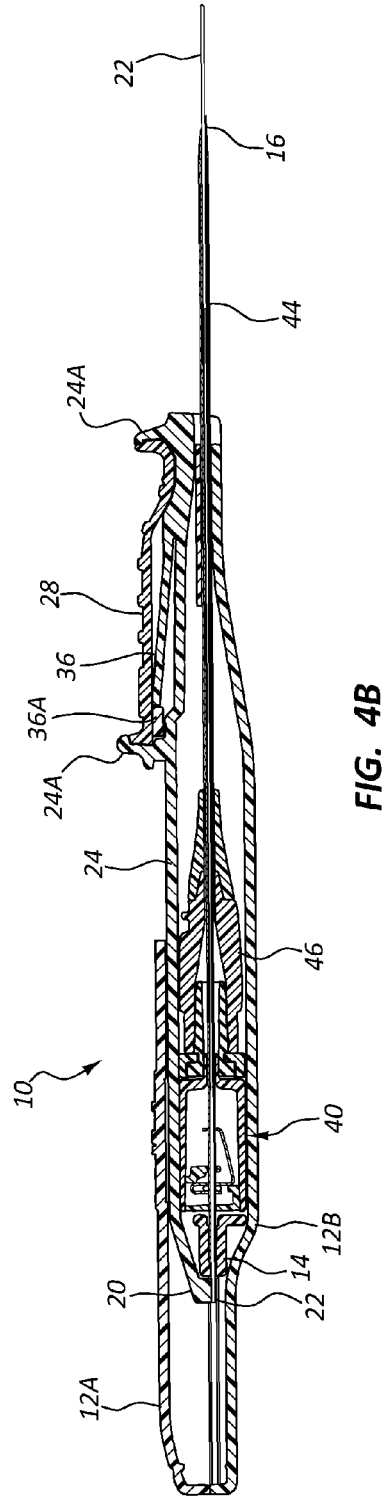
FIG. 4A
FIG. 4B

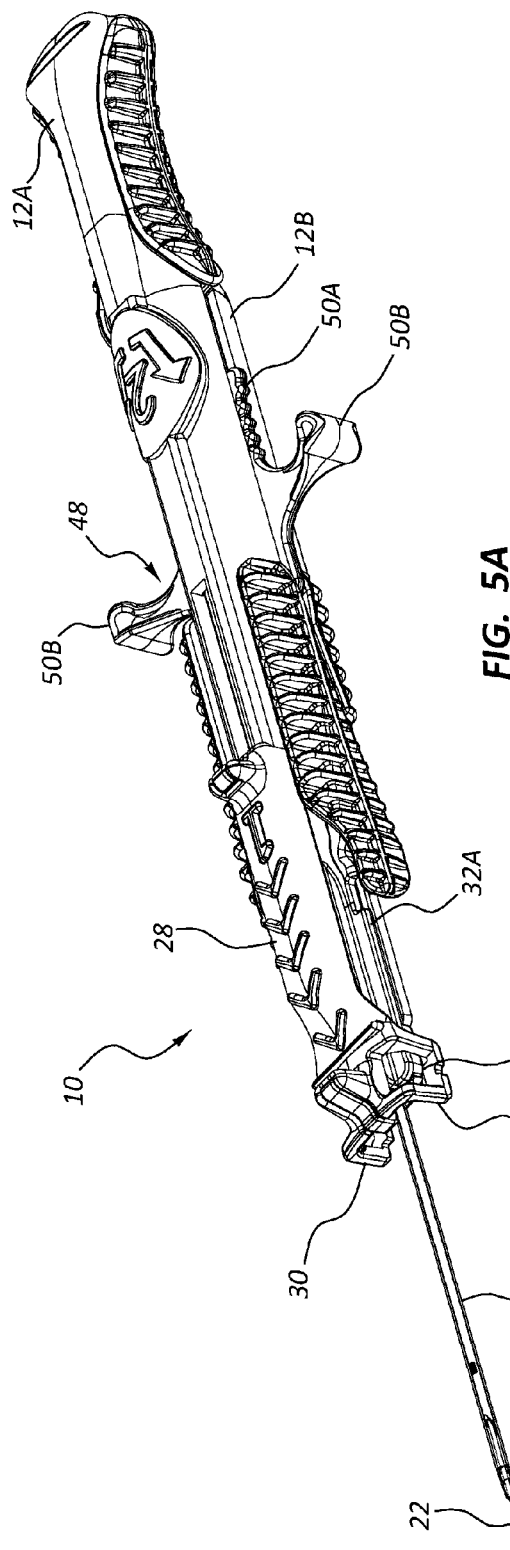
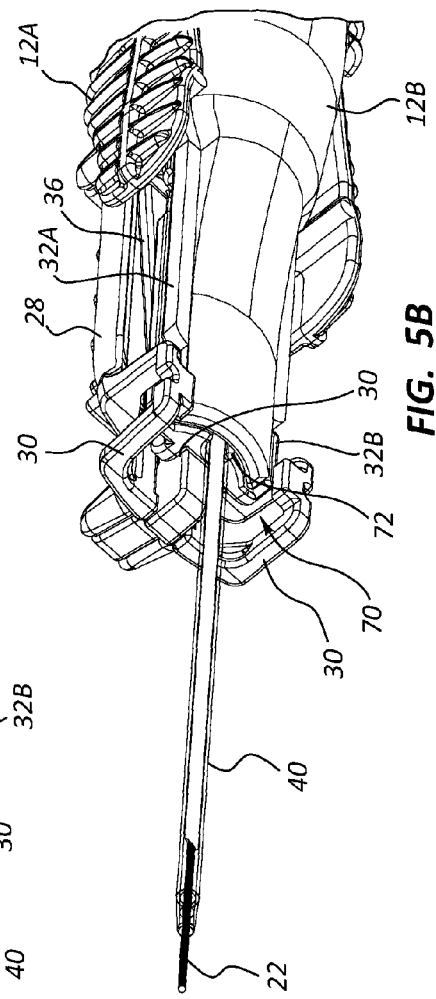
FIG. 5A
FIG. 5B

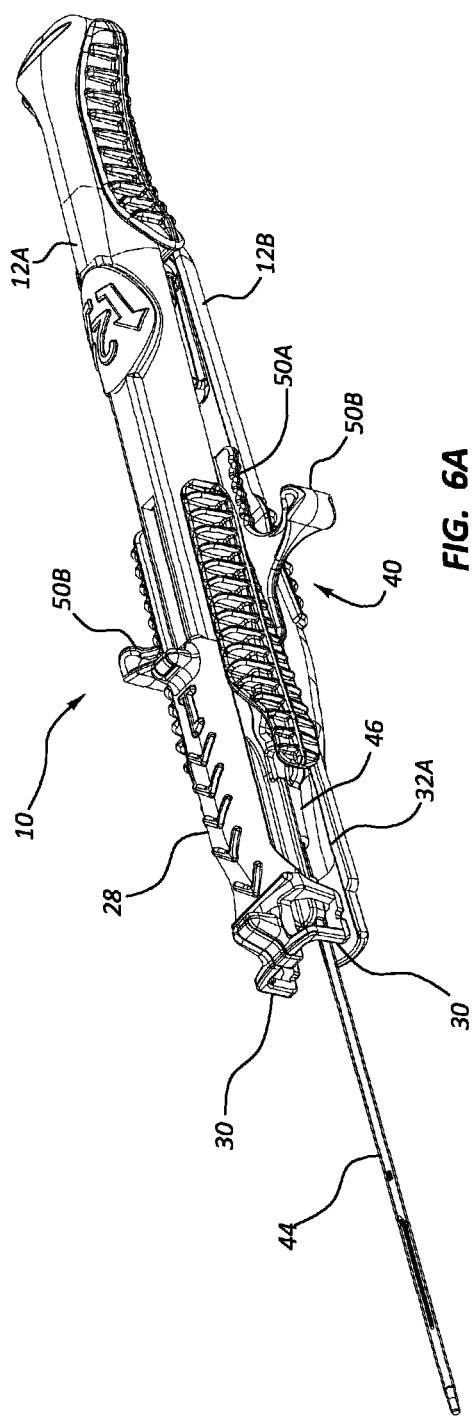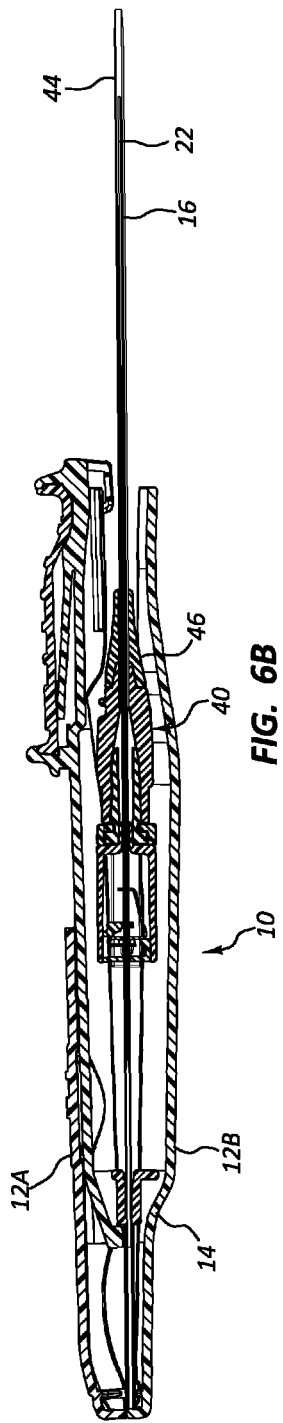
FIG. 6A
FIG. 6B

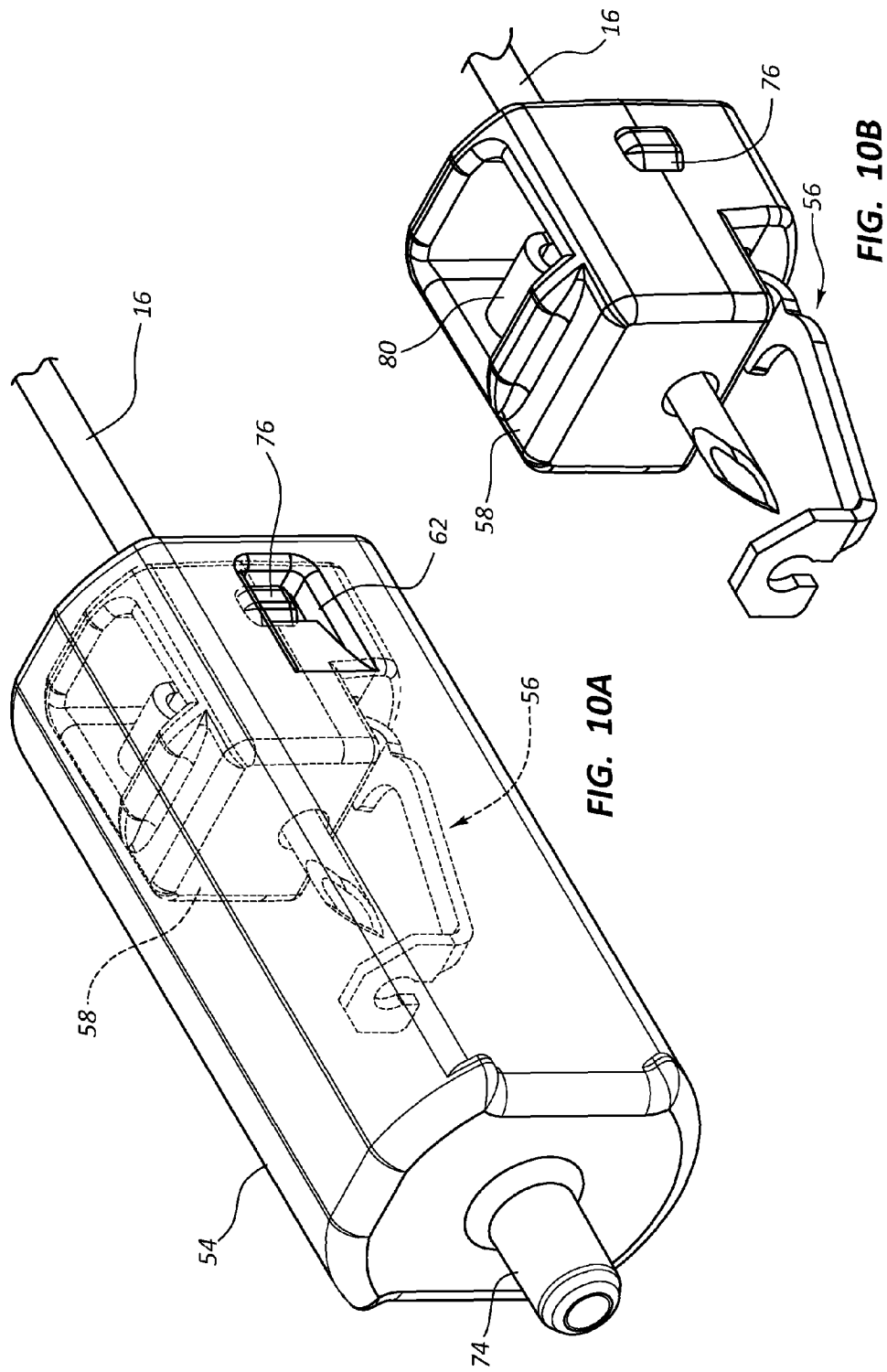

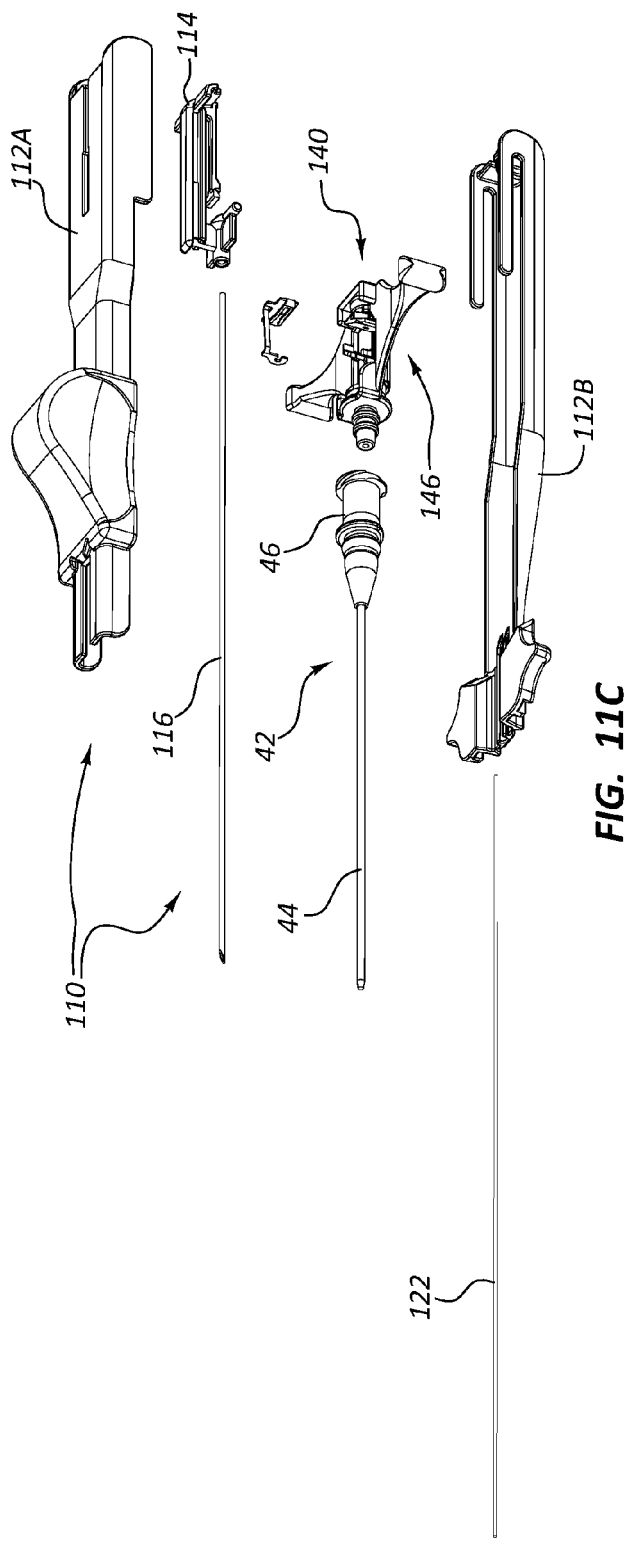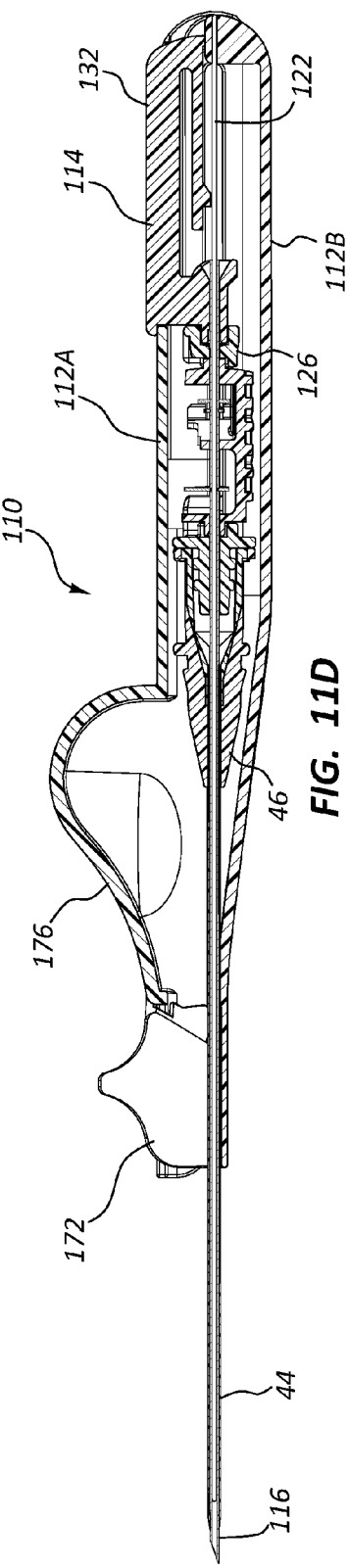

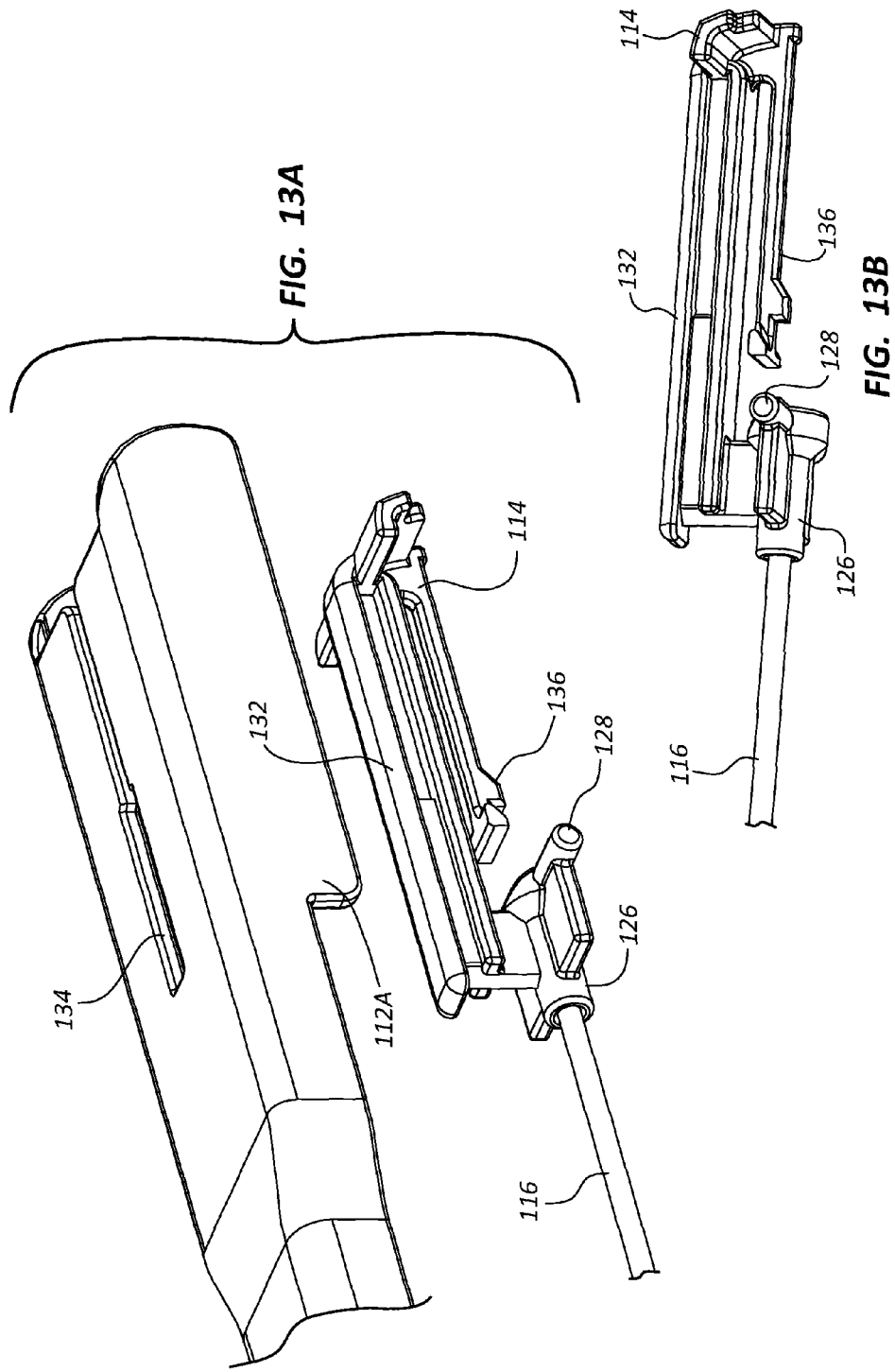

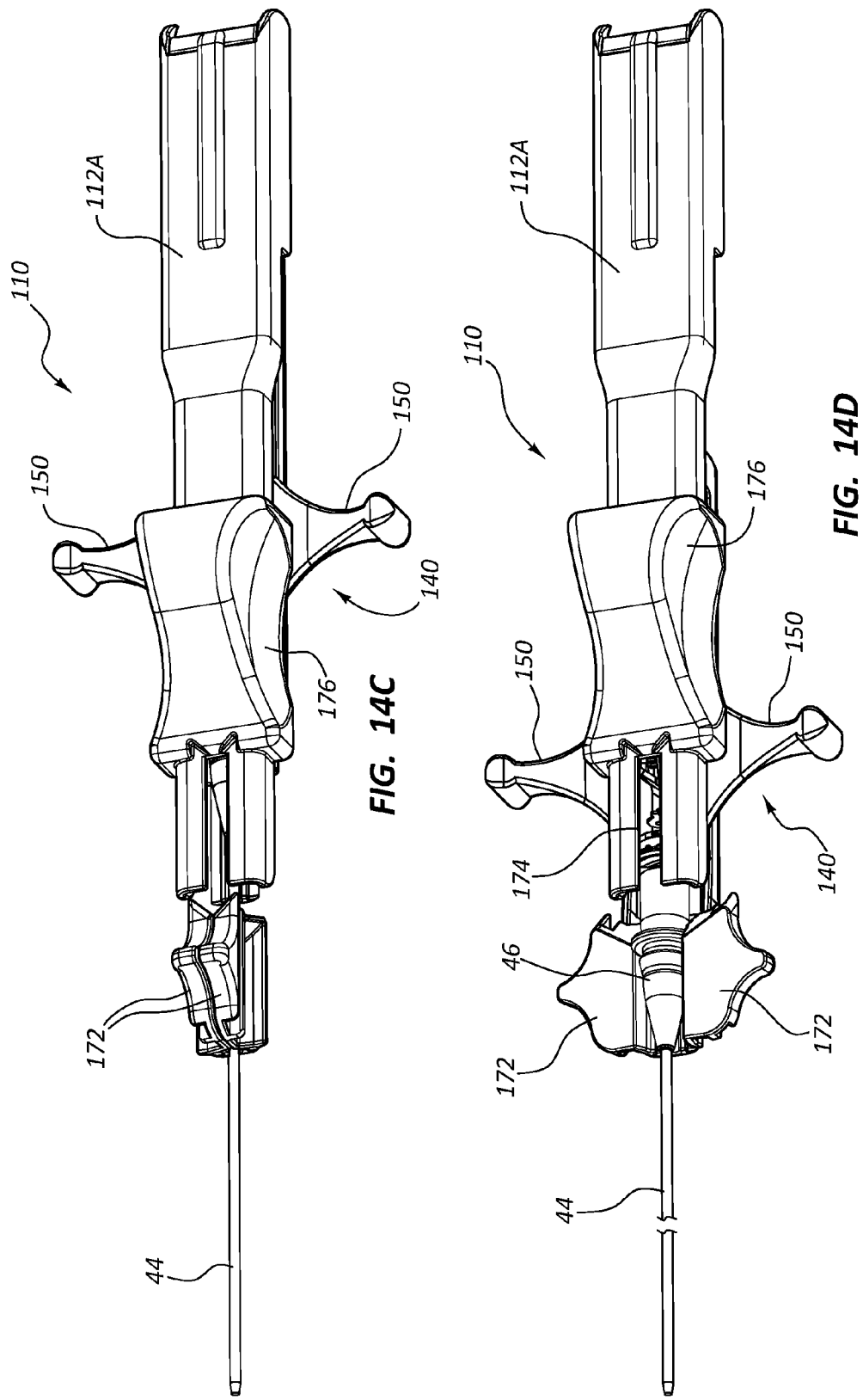

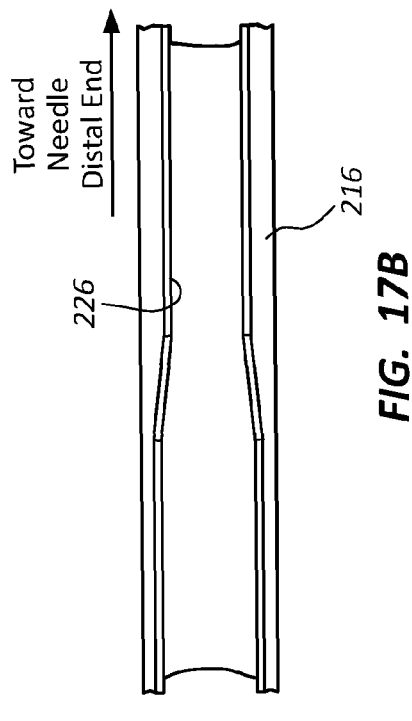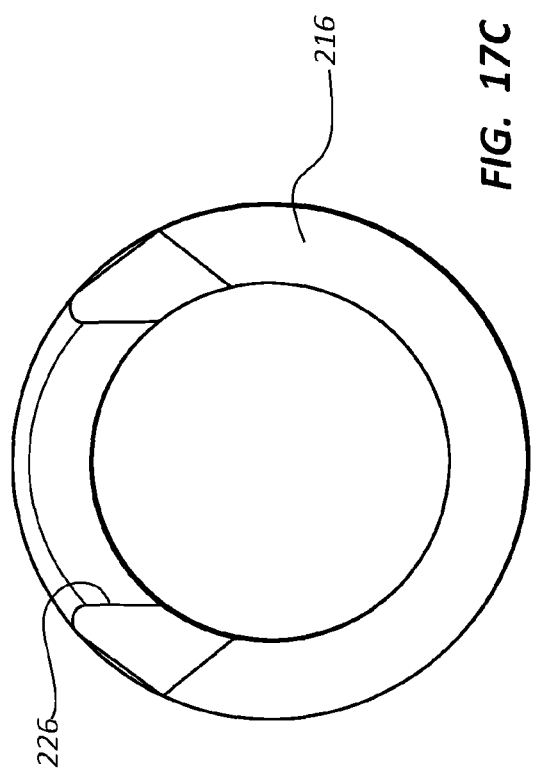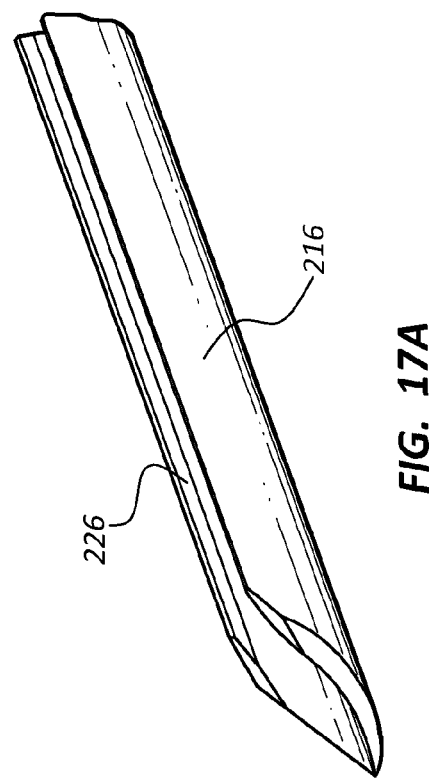
FIG. 17A
FIG. 17B
FIG. 17C

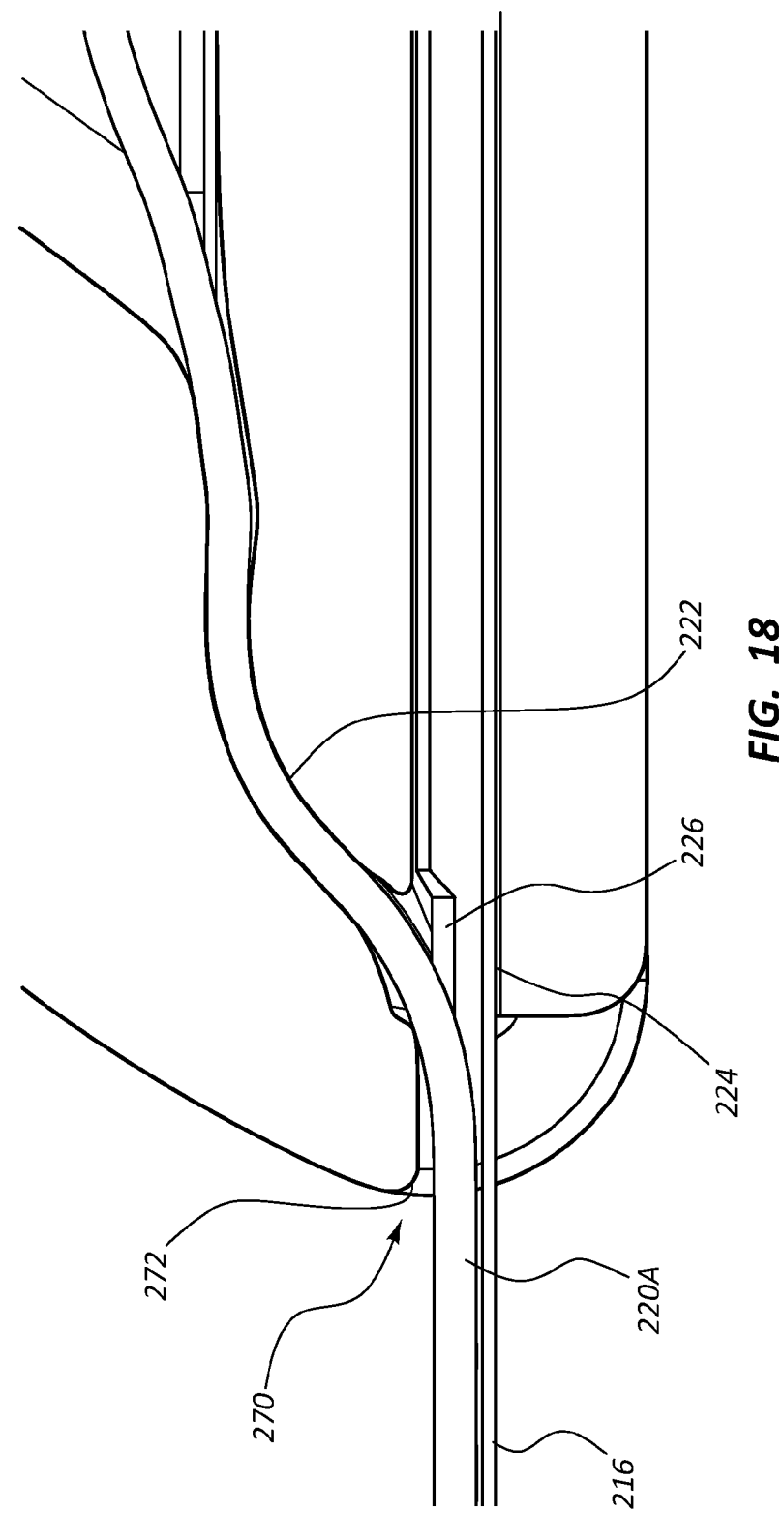

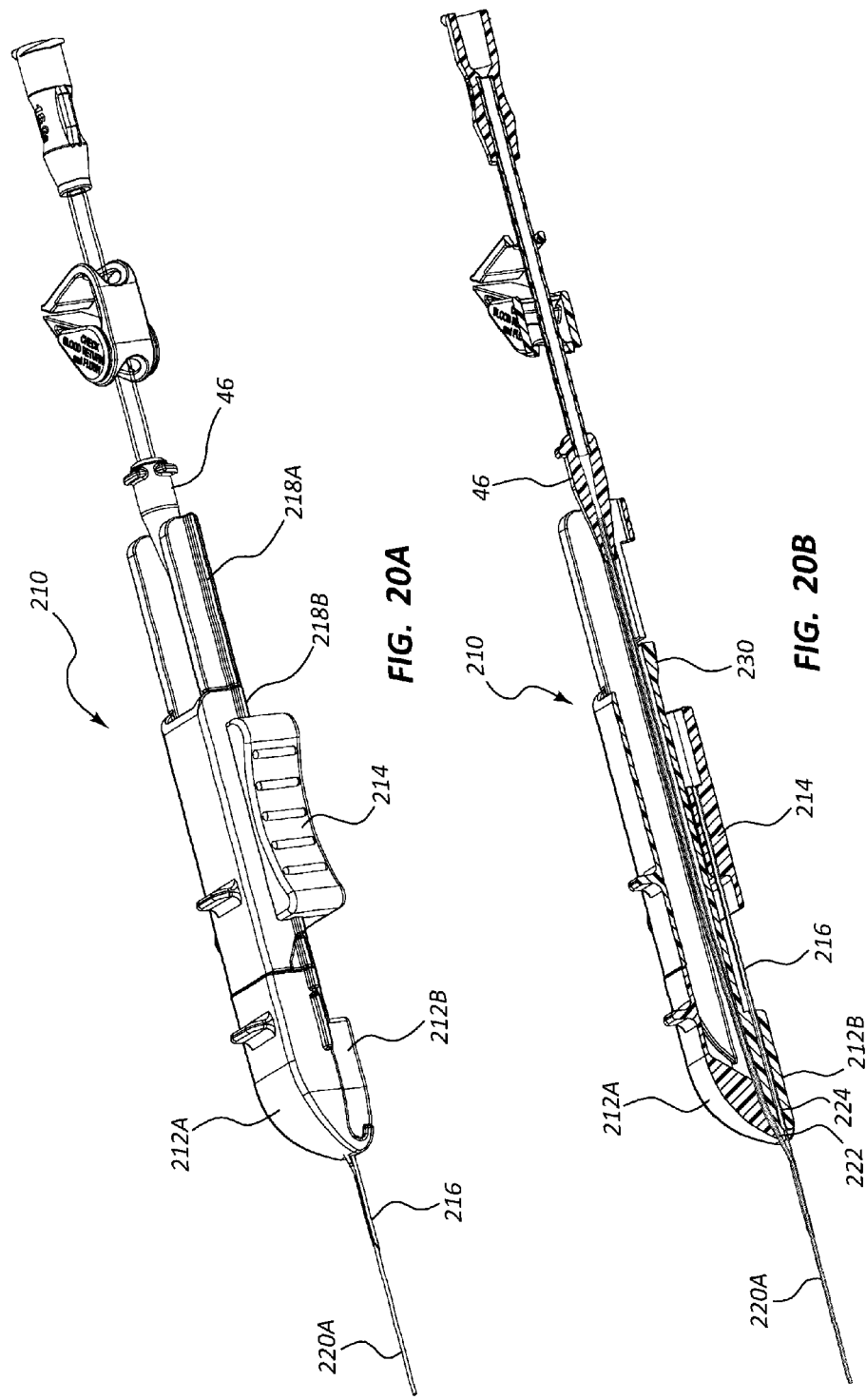

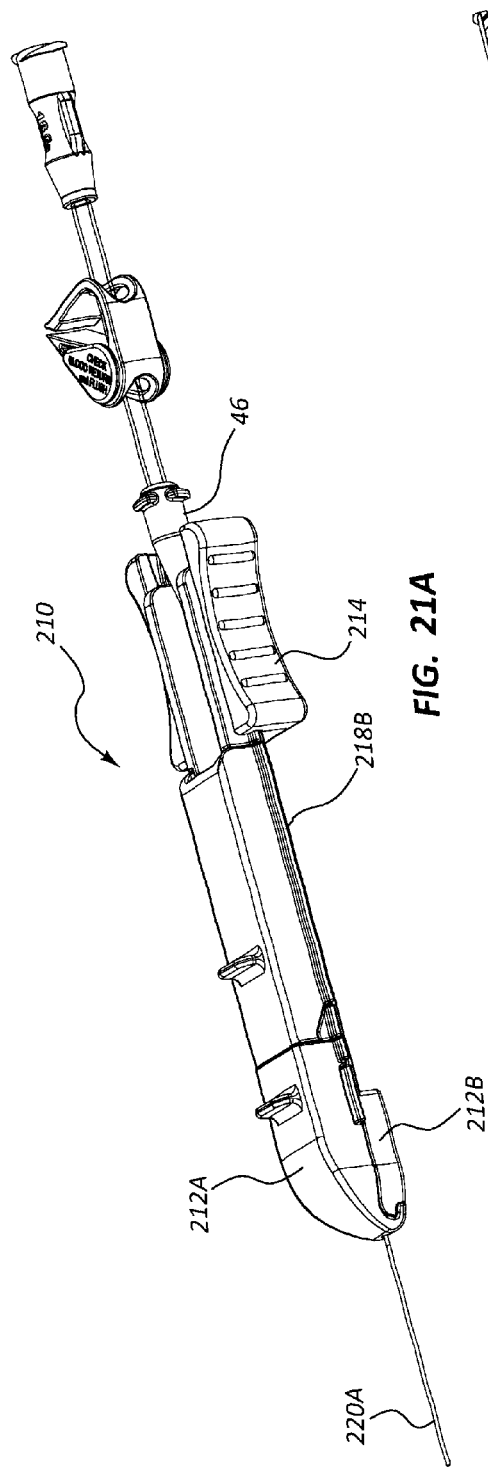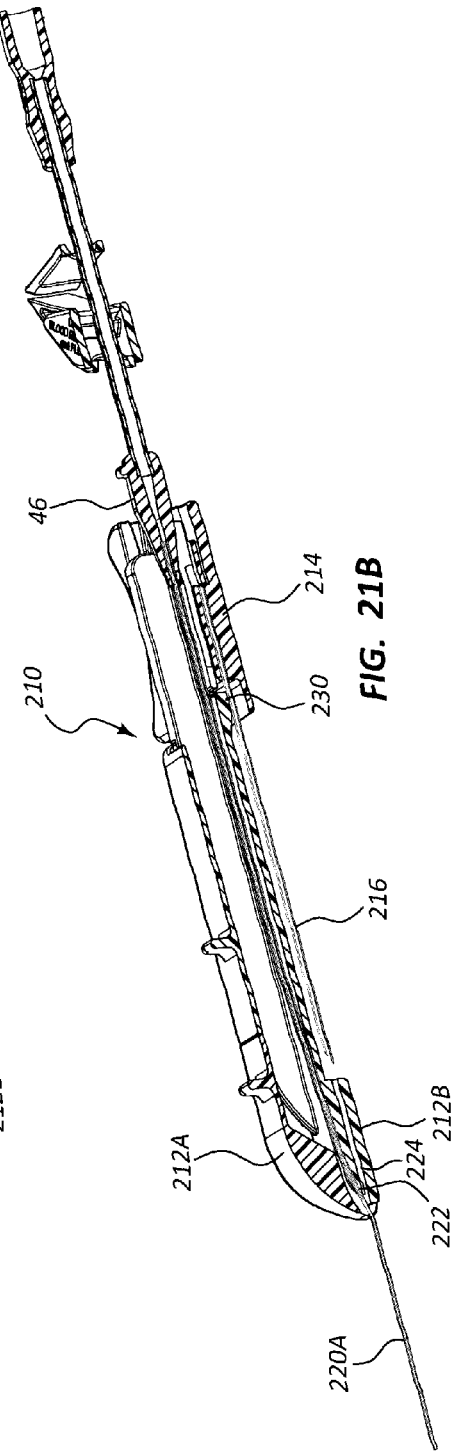
FIG. 21A
FIG. 21B

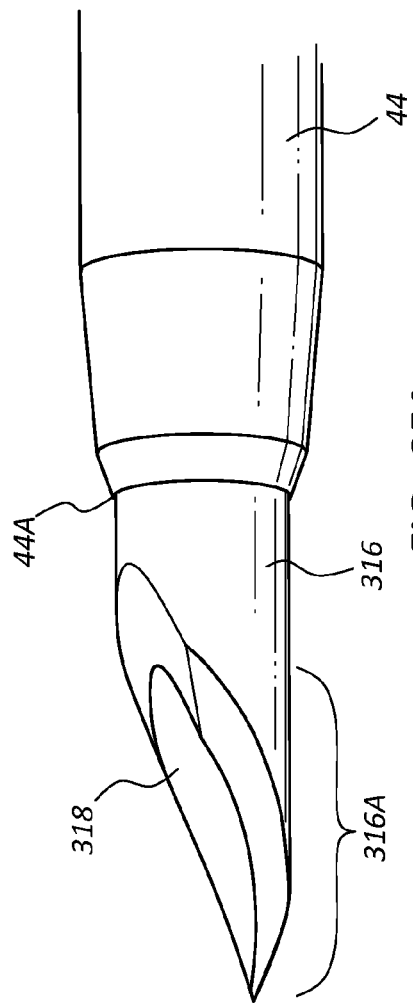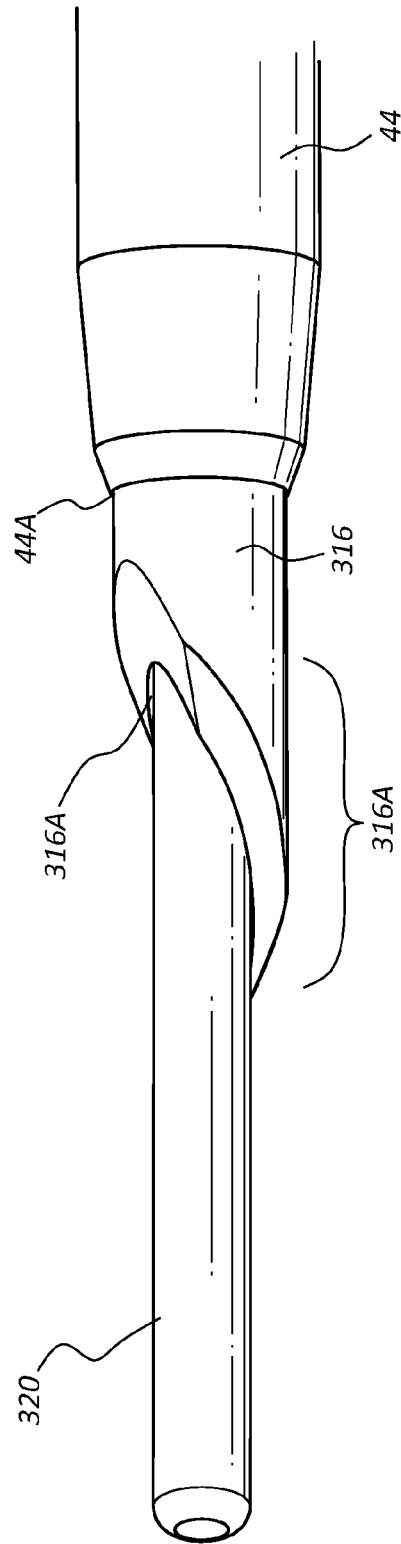
FIG. 25A
FIG. 25B

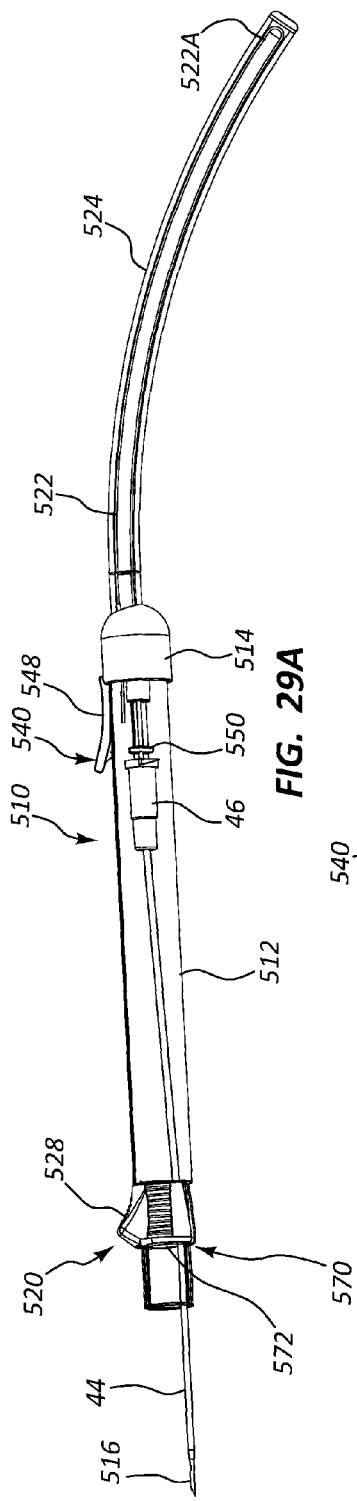
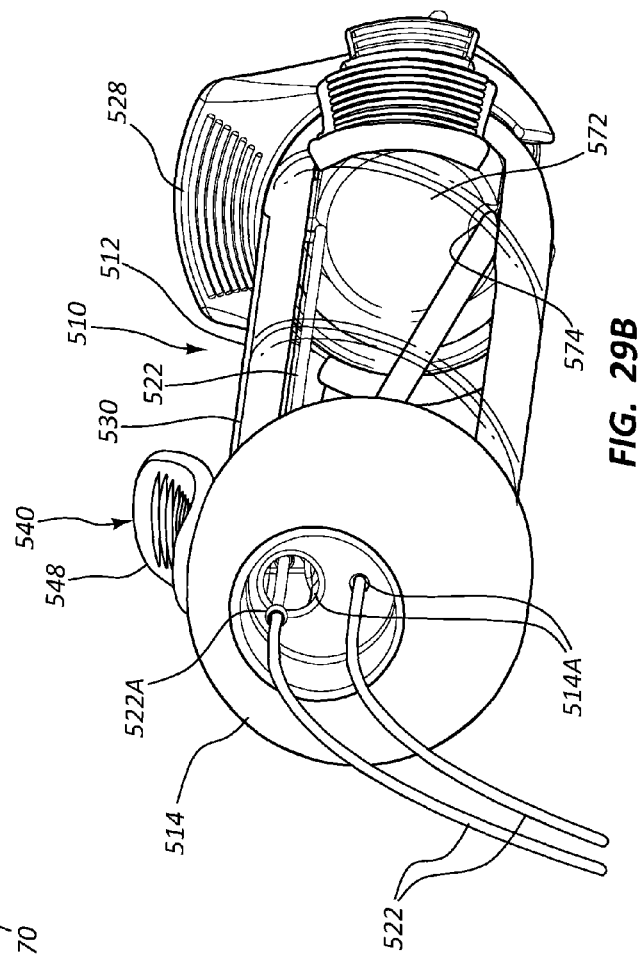
FIG. 29A
FIG. 29B

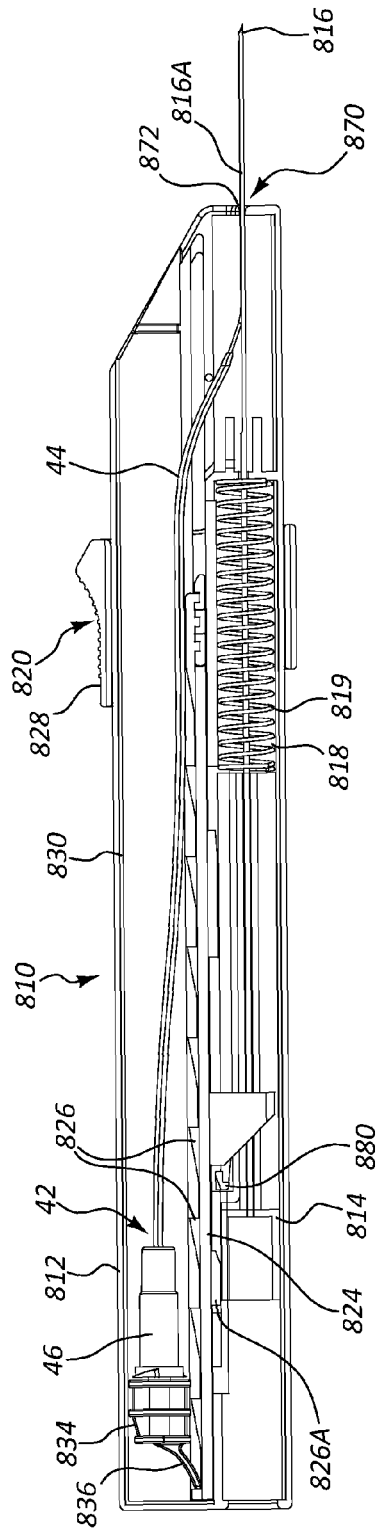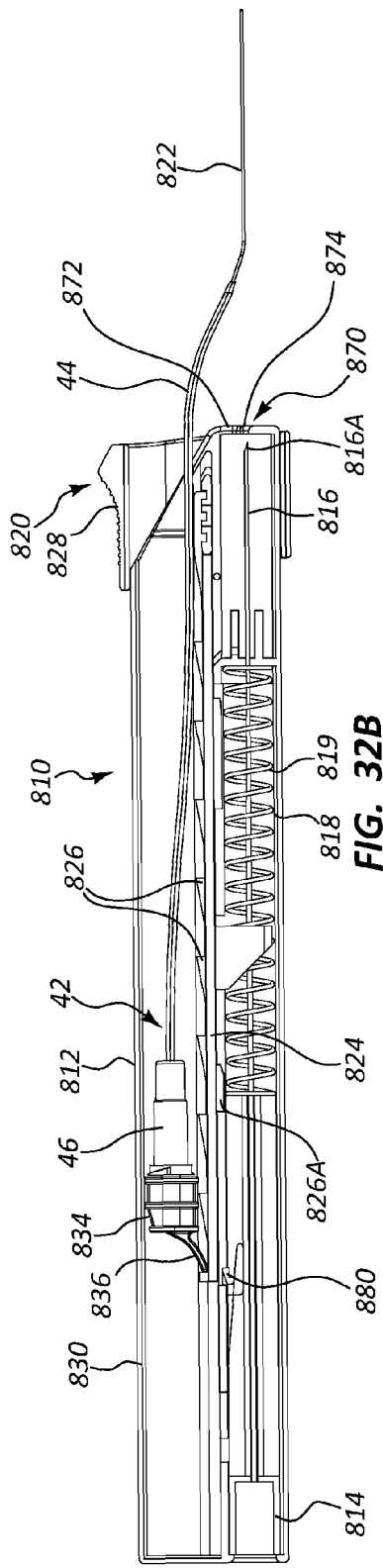
FIG. 32A
FIG. 32B

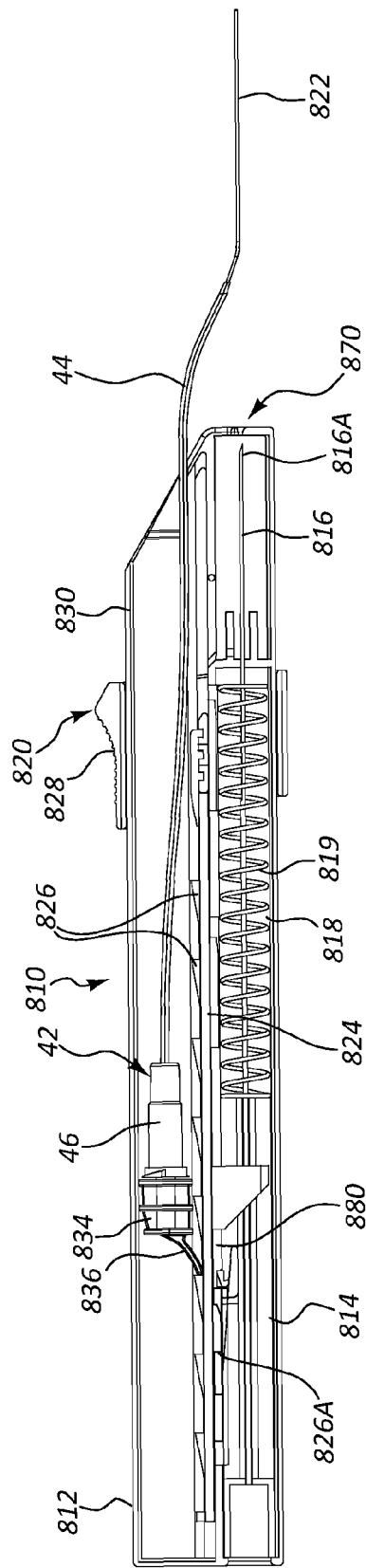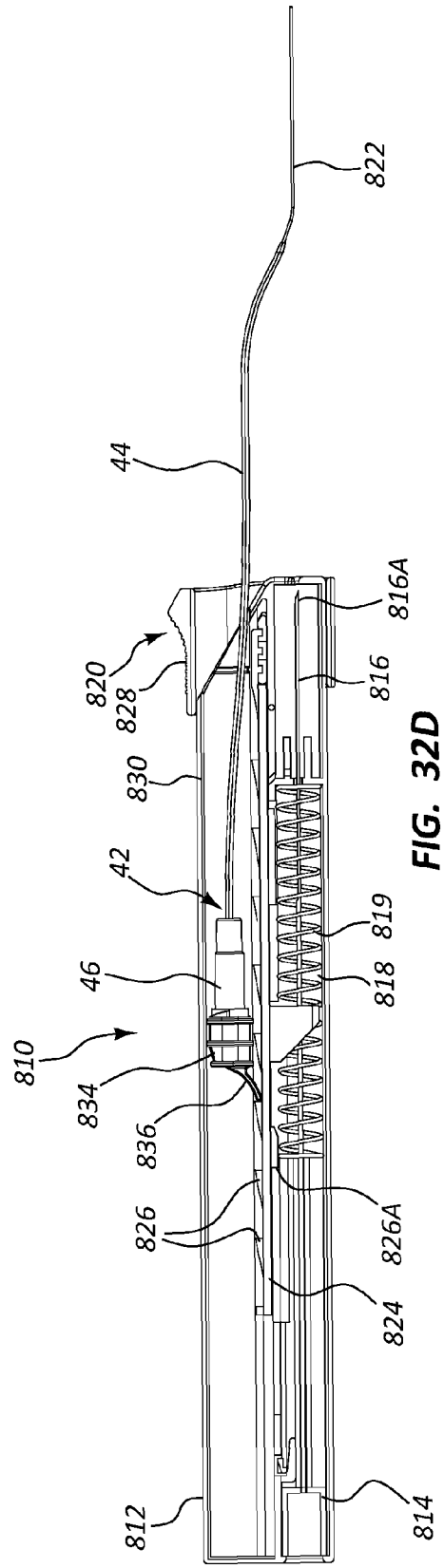
FIG. 32C
FIG. 32D

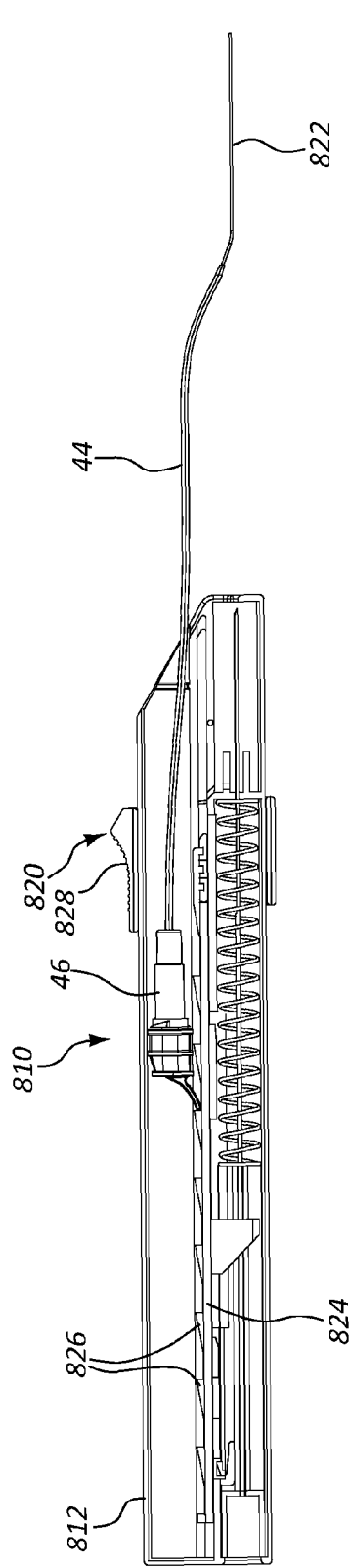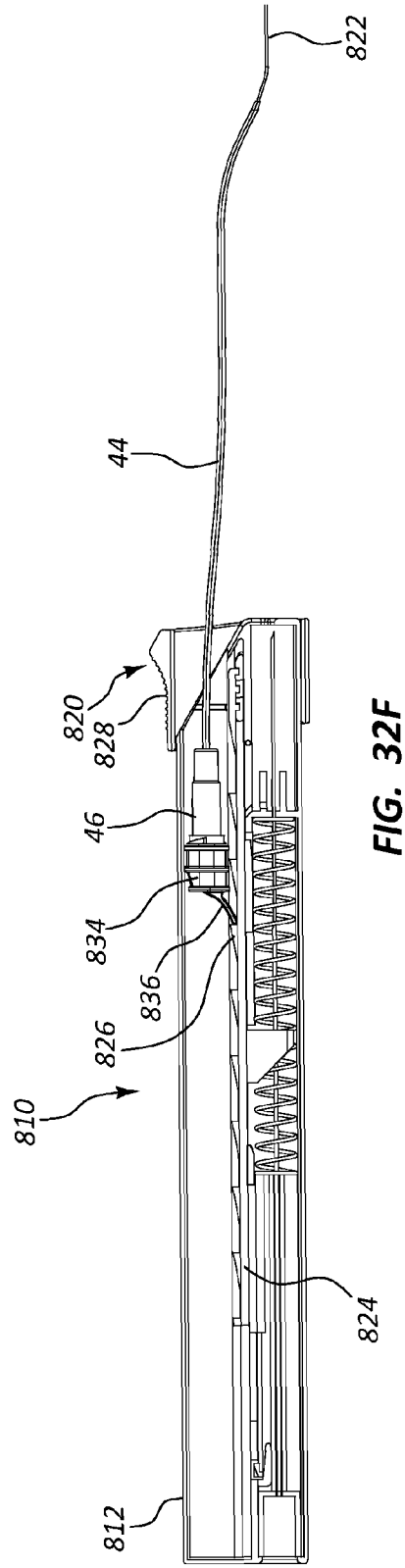
FIG. 32E
FIG. 32F

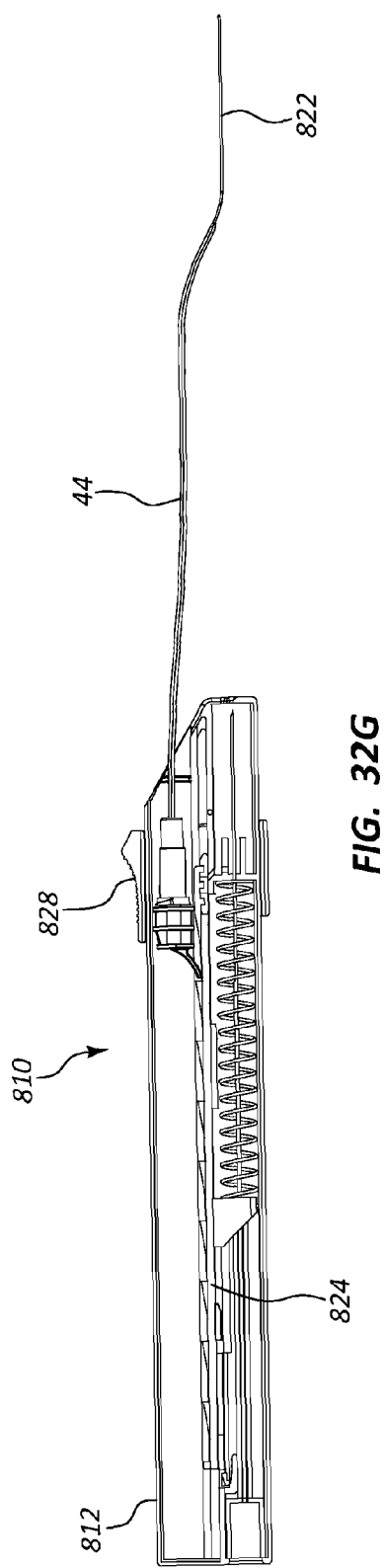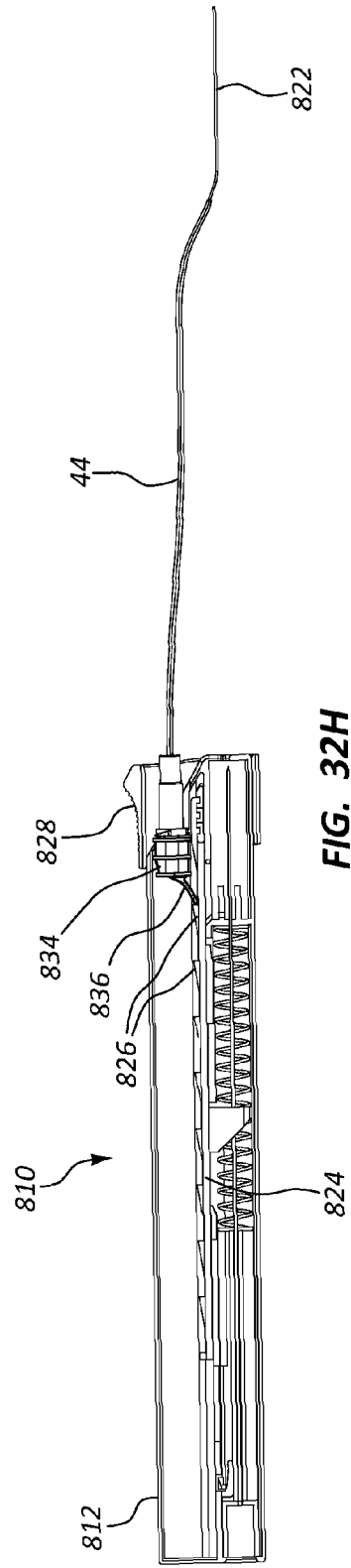

CATHETER PLACEMENT DEVICE AND METHOD

CROSS-REFERENCE TO RELATED APPLICATIONS

This application is a continuation of U.S. patent application Ser. No. 13/107,781, filed May 13, 2011, now U.S. Pat. No. 8,932,258, which claims the benefit of U.S. Provisional Application Nos. 61/345,005, filed May 14, 2010, and titled "Catheter Insertion System Including an Integrated Guidewire Dilator;" 61/345,022, filed May 14, 2010, and titled "Systems and Methods for Placement of an Intermediate Dwell Catheter Including a Needle Blunting System;" 61/372,050, filed Aug. 9, 2010, and titled "Catheter Insertion Tool Including Fold-out Guidewire Advancement Flaps;" 61/385,844, filed Sep. 23, 2010, and titled "Catheter Insertion Tool Including Guidewire Advancement;" and 61/415,248, filed Nov. 18, 2010, and entitled "Catheter Insertion Tool Including Openable Stabilizing Doors." Each of the aforementioned applications is incorporated herein by reference in its entirety.

BRIEF SUMMARY

Briefly summarized, embodiments of the present invention are directed to an insertion tool for inserting a catheter or other tubular medical device into a body of a patient. The insertion tool in one embodiment unifies needle insertion, guidewire advancement, and catheter insertion in a single device to provide for a simple catheter placement procedure.

In one embodiment, the insertion tool comprises a housing in which at least a portion of the catheter is initially disposed, a hollow needle distally extending from the housing with at least a portion of the catheter pre-disposed over the needle, and a guidewire pre-disposed within the needle. An advancement assembly is also included for selectively advancing the guidewire distally past a distal end of the needle in preparation for distal advancement of the catheter. In one embodiment a catheter advancement assembly is also included for selectively advancing the catheter into the patient. Each advancement assembly can include a slide or other actuator that enables a user to selectively advance the desired component.

In one embodiment the catheter advancement assembly further includes a handle that is initially and removably attached to a hub of the catheter within the housing. Distal movement of handle by a user in turn distally moves the catheter distally from the housing. The handle can include a needle safety component for isolating a distal tip of the needle when the needle is removed from the catheter and the distal tip received into the handle.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIGS. 3A and 3B show various views of one stage of use of the catheter insertion tool of FIGS. 1A and 1B according to one embodiment;

FIGS. 4A and 4B show various views of one stage of use of the catheter insertion tool of FIGS. 1A and 1B according to one embodiment;

FIGS. 5A and 5B show various views of one stage of use of the catheter insertion tool of FIGS. 1A and 1B according to one embodiment;

FIGS. 6A and 6B show various views of one stage of use of the catheter insertion tool of FIGS. 1A and 1B according to one embodiment;

FIGS. 10A-10C shows various views of a needle safety component and environment for a catheter insertion tool, according to one embodiment;

FIGS. 11A-11D are various views of a catheter insertion device according to one embodiment;

FIGS. 13A and 13B are various views of a portion of the catheter insertion device of FIGS. 11A-11D;

FIGS. 14A-14F show various stages of use of the catheter insertion tool of FIGS. 11A-11D according to one embodiment;

FIGS. 17A-17C are various views of a slotted needle for use with the catheter insertion device of FIGS. 15A and 15B according to one embodiment;

FIG. 18 is a cross sectional side view of a portion of the catheter insertion device of FIGS. 15A and 15B;

FIGS. 20A and 20B show one stage of use of the catheter insertion tool of FIGS. 15A and 15B according to one embodiment;

FIGS. 21A and 21B show one stage of use of the catheter insertion tool of FIGS. 15A and 15B according to one embodiment;

FIGS. 25A and 25B shows various views of a needle distal tip and guidewire blunting design according to one embodiment;

FIGS. 29A and 29B are various views of a catheter insertion tool according to one embodiment;

FIGS. 32A-32I are various views of a configuration of a catheter insertion tool during use, according to one embodiment.

DETAILED DESCRIPTION OF SELECTED EMBODIMENTS

Figure 1A:
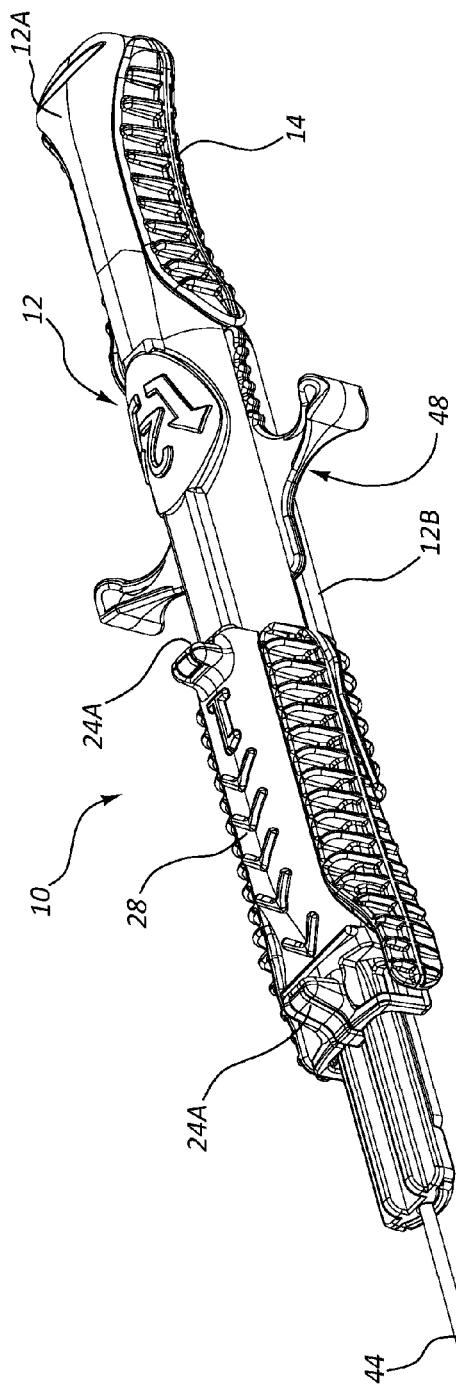
FIGS. 1A and 1B are various views of a catheter insertion device according to one embodiment.

Reference will now be made to figures wherein like structures will be provided with like reference designations. It is understood that the drawings are diagrammatic and schematic representations of exemplary embodiments of the present invention, and are neither limiting nor necessarily drawn to scale.

For clarity it is to be understood that the word "proximal" refers to a direction relatively closer to a clinician using the device to be described herein, while the word "distal" refers to a direction relatively further from the clinician. For example, the end of a catheter placed within the body of a patient is considered a distal end of the catheter, while the catheter end remaining outside the body is a proximal end of the catheter. Also, the words "including," "has," and "having," as used herein, including the claims, shall have the same meaning as the word "comprising."

Embodiments of the present invention are generally directed to a tool for assisting with the placement into a patient of a catheter or other tubular medical device. For example, catheters of various lengths are typically placed into a body of a patient so as to establish access to the patient's vasculature and enable the infusion of medicaments or aspiration of body fluids. The catheter insertion tool to be described herein facilitates such catheter placement. Note that, while the discussion below focuses on the placement of catheters of a particular type and relatively short length, catheters of a variety of types, sizes, and lengths can be inserted via the present device, including peripheral IV's intermediate or extended-dwell catheters, PICC's, central venous catheters, etc. In one embodiment, catheters having a length between about 2.5 inches and about 4.5 inches can be placed, though many other lengths are also possible. In another embodiment a catheter having a length of about 3.25 inches can be placed.

Reference is first made to FIGS. 1A-1B and 2A-2B, which depict various details regarding a catheter insertion tool ("insertion tool"), generally depicted at 10, according to one embodiment. As shown, the insertion tool 10 includes a housing 12 that in turn includes a top housing portion 12A separably mated with a bottom housing portion 12B. A needle hub 14 supporting a hollow needle 16 is interposed between the housing portions 12A and 12B. The needle 16 extends distally from the needle hub 14 so as to extend through the body of the insertion tool 10 and out a distal end of the housing 12. In another embodiment, the needle is at least partially hollow while still enabling the functionality described herein.

A notch 18 is defined through the wall of the needle 16 proximate the distal end thereof. The notch 18 enables flashback of blood to exit the lumen defined by the hollow needle 16 once access to the patient's vasculature is achieved during catheter insertion procedures. Thus, blood exiting the notch 18 can be viewed by a clinician to confirm proper needle placement in the vasculature, as will be explained further below.

Figure 1B:
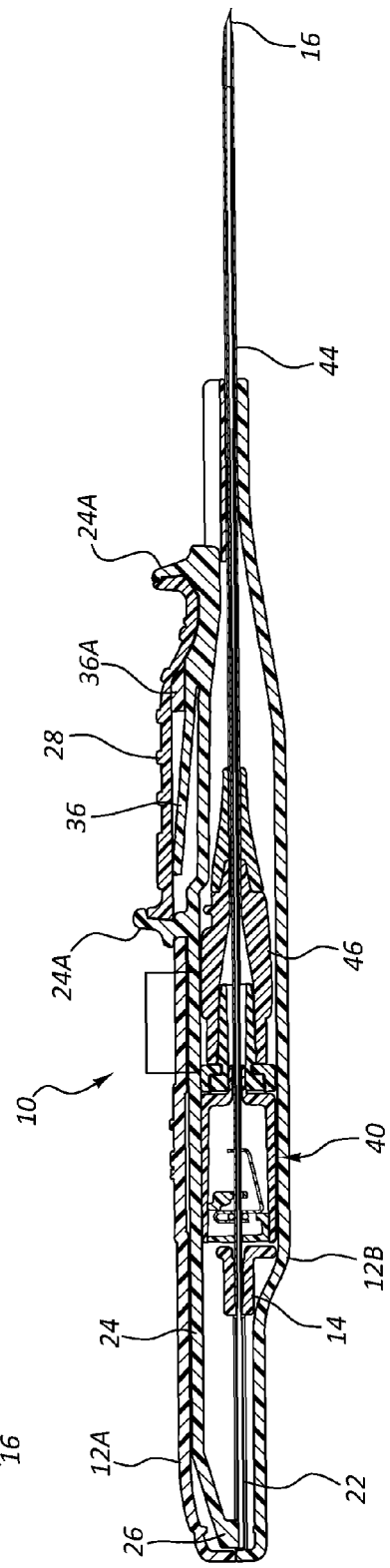
Figure 2A:
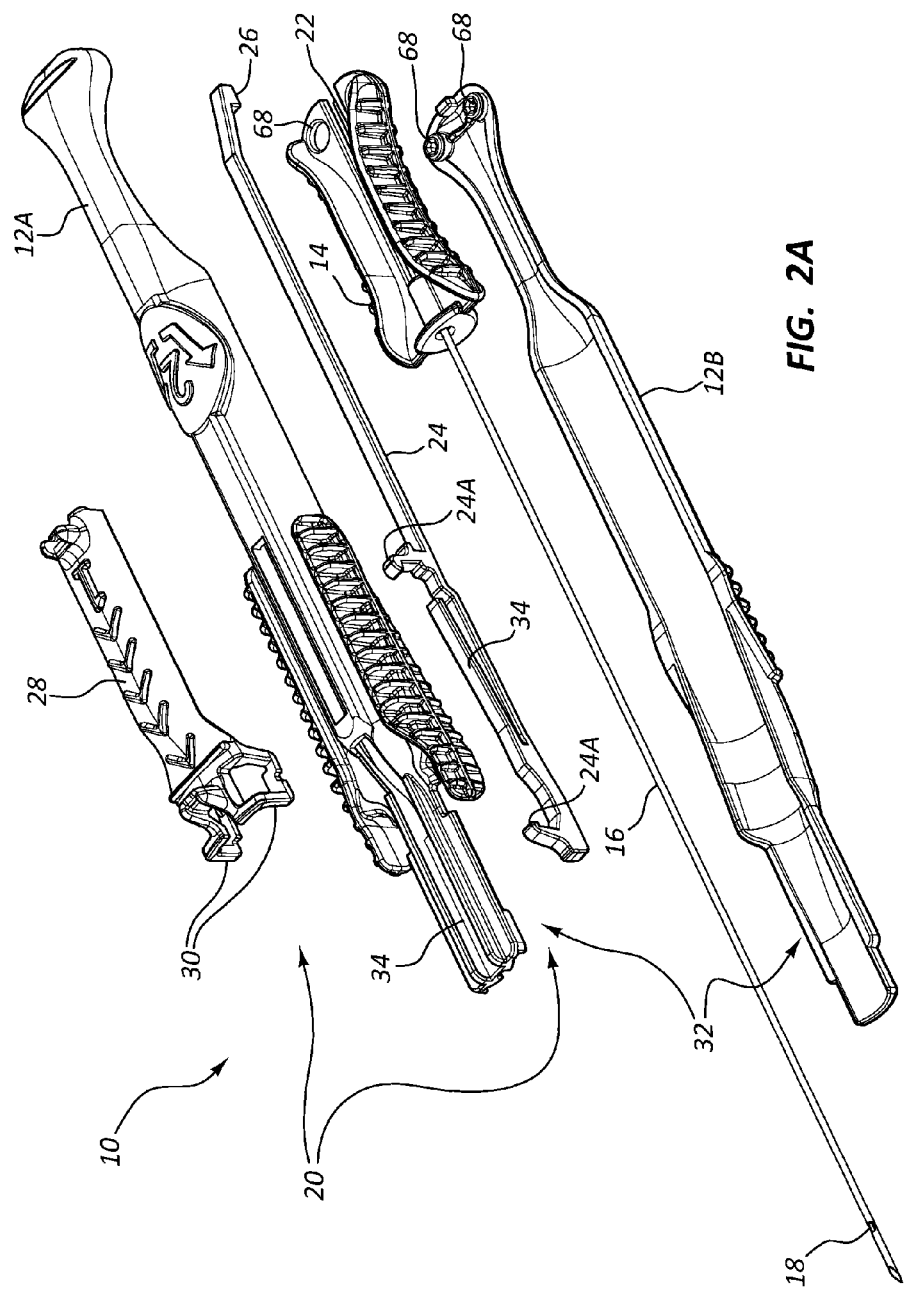
FIGS. 2A and 2B are various exploded views of the catheter insertion device of FIGS. 1A and 1B.

The insertion tool 10 further includes a guidewire advancement assembly 20 for advancing a guidewire 22 through the needle 16 and into the vasculature of the patient once access by the needle has been achieved. The guidewire 22 is pre-disposed within the lumen of the needle 16, with a proximal end of the guidewire positioned proximate the proximal end of the needle hub 14, as best seen in FIGS. 1B and 2A. The guidewire advancement assembly 20 includes a guidewire lever 24 that selectively advances the guidewire in a distal direction during use of the insertion tool 10 such that the distal portion of the guidewire extends beyond the distal end of the needle 16. The guidewire lever 24 includes a lever tab 26 that engages the proximal end of the guidewire 22 so to push the guidewire through the lumen of the needle 16.

The guidewire advancement assembly 20 further includes a slide 28 that is slidably attached to the top housing portion 12A. Two tabs 24A of the guidewire lever 24 operably attach to the slide 28 so that selective movement by a user of the slide results in corresponding movement of the lever 24, and by extension, the guidewire 22. Engagement of the lever tabs 24A to the slide 28 also maintains attachment of the slide to the housing 12. Of course, other engagement schemes to translate user input to guidewire movement could also be employed. Suitable tracks are included in the top housing portion 12A to enable sliding movement of the slide 28 and the lever 24, including a track 34 extending to the distal end of the housing 12.

The slide 28 includes two arms 30 that wrap partially about rails 32 defined by the housing 12. In particular, during initial distal advancement of the slide 28, the arms 30 slide on a bottom housing rail 32A, best seen in FIG. 5B. During further distal advancement of the slide 28, the arms 30 slide past the bottom housing rail 32A and on to a top housing rail 32B, best seen in FIGS. 2A and 3A. With the arms 30 of the slide 28 no longer engaged with the bottom housing rail 32A, the two housing portions 12A and 12B are able to separate, as will be described further below.

The guidewire lever 24 includes a locking arm 36 resiliently disposed so as to spring up and engage an extension 36A defined in the interior of the top housing portion 12A when the slide 28 has been fully slid distally. This prevents inadvertent retraction of the guidewire 22 once distally extended, which could otherwise cause unintended severing of a distal portion of the guidewire by the distal tip of the needle 16 during insertion procedures. Note that engagement of the locking arm 36 with the extension 36A can provide tactile and/or audible feedback to the user in one embodiment so as to indicate full distal extension of the guidewire 22.

The insertion tool 10 further includes a catheter advancement assembly 40 for selectively advancing in a distal direction a catheter 42, pre-disposed in the housing 12, and including a catheter tube 44 and a hub 46 at a proximal end thereof. As seen in FIGS. 1A and 1B, the catheter 42 is partially and initially pre-disposed within a volume defined by the housing 12 such that the lumen of the catheter tube 44 is disposed over the needle 16, which in turn is disposed over the guidewire 22, as mentioned.

In particular, the catheter advancement assembly 40 includes a handle 48 that defines a base 48A and two arms 50 extending from the handle base. Each arm 50 defines a grip surface 50A, finger grabs 50B, and one of two teeth 50C. The grip surfaces 50A and finger grabs 50B enable the handle to be grasped or contacted by a user in order to selectively advance the catheter 42 in a distal direction during use of the insertion tool 10 to insert the catheter into the body of the patient. The teeth 50C engage corresponding raised surfaces on the hub 46 so as to removably connect the handle 48 to the catheter 42.

Figure 2B:
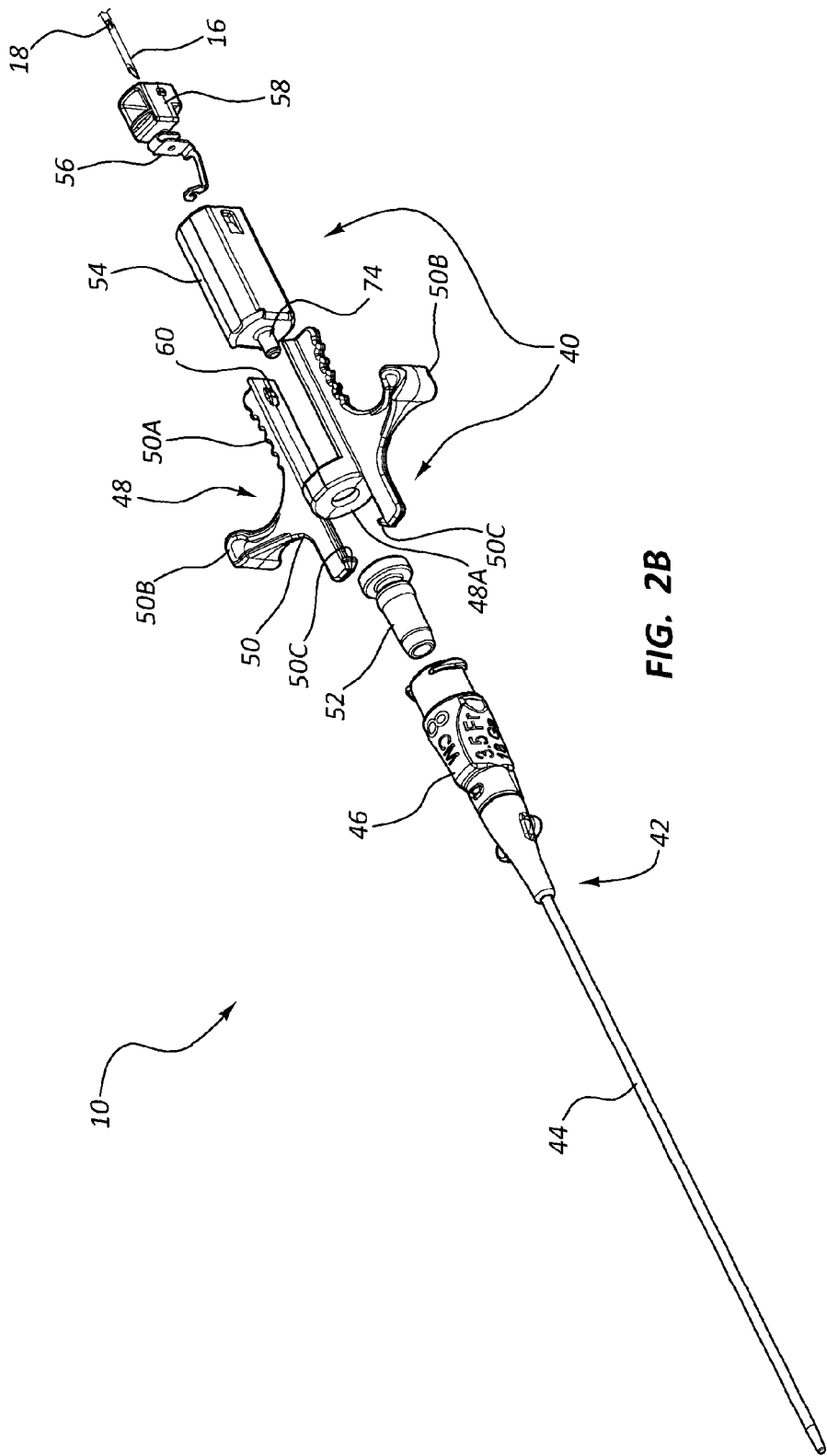

Additional components are included in relation to the handle 48 of the catheter advancement assembly 40. A plug, or valve 52, is interposed between the handle base 48A and the catheter hub 46 to prevent blood spillage when the catheter is first introduced into the patient vasculature. A safety housing 54, including a needle safety component 56 therein, is removably attached to the handle 48 between the arms 50. Specifically, protrusions 60 included on the inner surfaces of the handle arms 50 engage with corresponding recesses 62 (FIG. 10A) defined in the safety housing 54 to removably secure the safety housing to the handle 48. A cap 58 supports the needle safety component 56 and covers the end of the safety housing 54. As shown in FIG. 1B, the needle 16 initially extends through the aforementioned components in the order as shown in FIG. 2B. Further details regarding the operation of these components are given below.

Note that in one embodiment the outer diameters of the needle 16 and the catheter tube 44 are lubricated with silicone or other suitable lubricant to enhance sliding of the catheter tube with respect to the needle and for aiding in the insertion of the catheter into the body of the patient.

The insertion tool 10 further includes a support structure 70 for stabilizing the needle 16 proximate its point of exit from the housing 12. In the present embodiment, the support structure 70 includes an interface 72 of the top housing portion 12A and bottom housing 12B that is shaped to closely match the round shape of the needle 16 and catheter tube 44. The interface 72 stabilizes the needle 16 so as to prevent excessive "play" in the needle, thus improving user accuracy when initially accessing the vasculature of the patient.

As best seen in FIG. 2A, the top housing 12A, the needle hub 14, and the bottom housing 12B include engagement features 68 to maintain attachment of the proximal end of the housing 12 even when more distal portions of the housing are separated, discussed below. Note, however, that various types, sizes, and numbers of engagement features can be employed to achieve this desired functionality.

FIGS. 3A-9 depict various stages of use of the insertion tool 10 in placing the catheter 42 in the vasculature of a patient. For clarity, the various stages are depicted without actual insertion into a patient being shown. With the insertion tool 10 in the configuration shown in FIG. 1A, a user grasping the insertion tool 10 first guides the distal portion of the needle 16 through the skin at a suitable insertion site and accesses a subcutaneous vessel. Confirmation of proper vessel access having been achieved is evident via blood flash, i.e., the presence of blood between the outer diameter of the needle 16 and the inner diameter of the catheter tube 44 due to blood passing out the notch 18 from the hollow interior of the needle. Note that in one embodiment, the presence of blood in the safety housing 54, which in one embodiment is a translucent housing, can serve as a secondary blood flash indicator due to blood entering the housing from the needle 16 when the vessel is accessed.

After needle access to the vessel is confirmed, the guidewire advancement assembly 20 is actuated, wherein the slide 28 is advanced by the finger of the user to distally advance the guidewire 22 (FIGS. 3A and 3B), initially disposed within the hollow needle 16. Note that the guidewire is distally advanced by the lever 24, which is operably attached to the slide 28. Note also that during distal advancement of the slide 28, the slide arms 30 thereof travel along the rails 32 on either side of the housing 12: first the bottom housing rails 32A, then the top housing rails 32B.

Distal guidewire advancement continues until the slide 28 has been distally slid its full travel length, resulting in a predetermined length of the guidewire 22 extending past the distal end of the needle 16, as shown in FIGS. 4A and 4B. In one embodiment, further distal advancement of the slide 28 is prevented by contact of the lever tab 26 with a distal portion of the needle hub 14, as shown in FIG. 4B. FIGS. 5A and 5B show that, upon full distal advancement of the slide 28, the slide arms 30 thereof are no longer engaged with the bottom housing rails 32A, but rather with only the top housing rails 32B. This in turn enables the housing portions 12A and 12B to separate, as seen further below.

As seen in FIGS. 5A and 5B, once the guidewire 22 has been fully extended within the vessel of the patient (FIGS. 4A and 4B), the catheter advancement assembly 40 is actuated, wherein the handle 48 is distally advanced by the user to cause the catheter tube 44 to slide over distal portions of the needle 16 and guidewire 22 and into the patient's vasculature via the insertion site. FIGS. 6A and 6B show that, as the catheter is advanced via the handle 48, the housing portions 12A and 12B are easily separated so as to enable the catheter hub 46 to exit the distal end of the housing 12 and for the catheter to be inserted into the patient vasculature to a suitable degree.

Figure 7A:
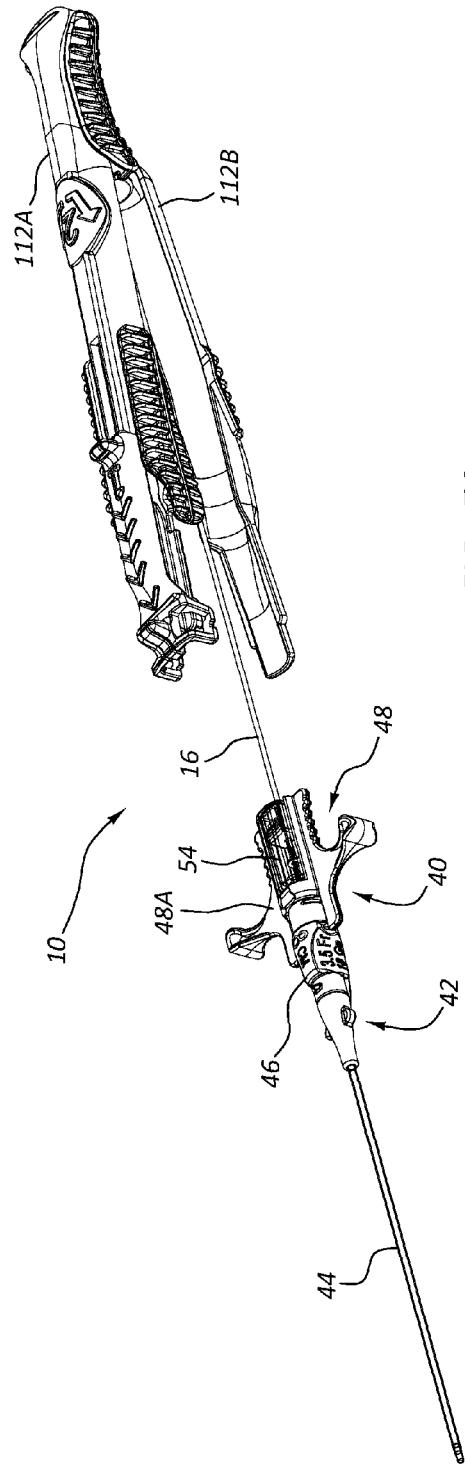
FIGS. 7A and 7B show various views of one stage of use of the catheter insertion tool of FIGS. 1A and 1B according to one embodiment.
Figure 7B:
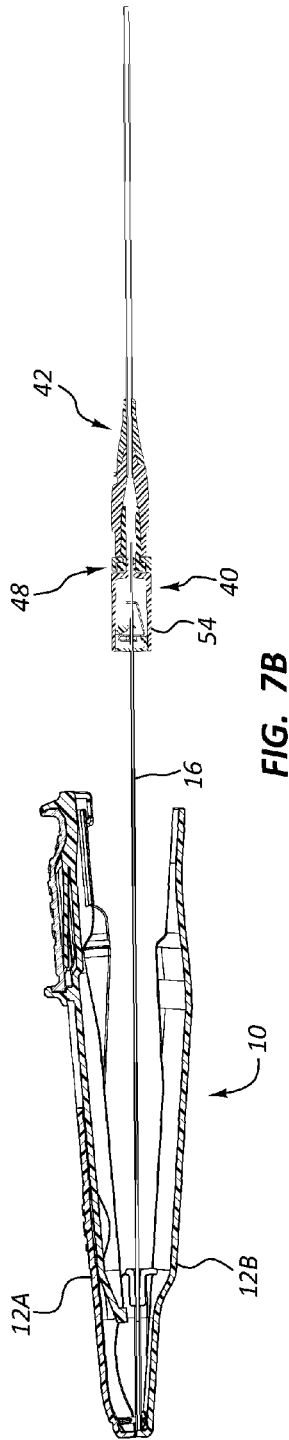
Figure 8:
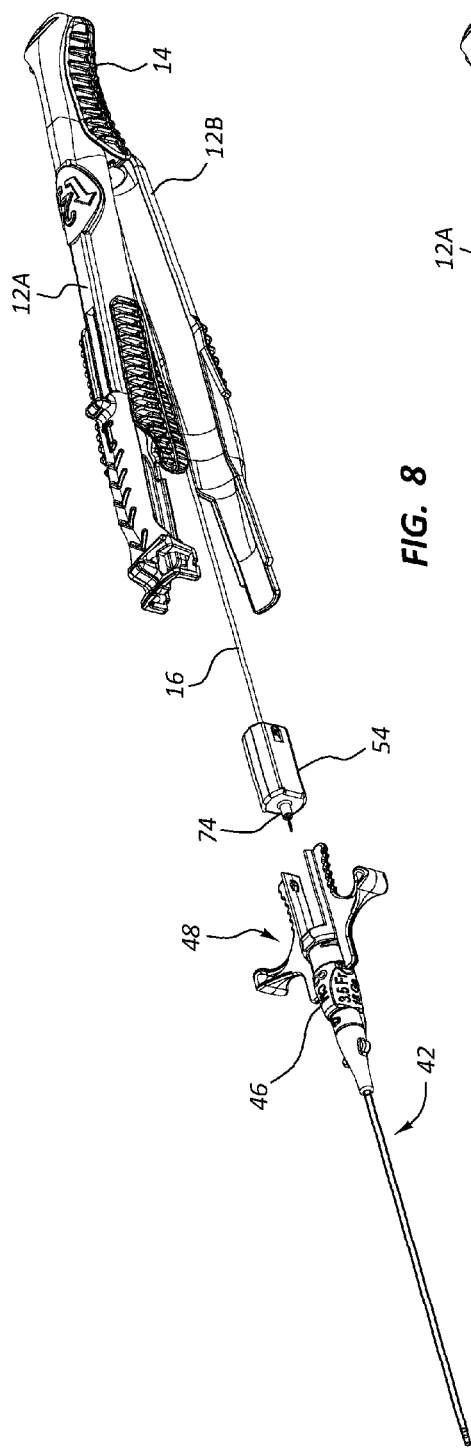
FIG. 8 shows one stage of use of the catheter insertion tool of FIGS. 1A and 1B according to one embodiment.
Figure 9:
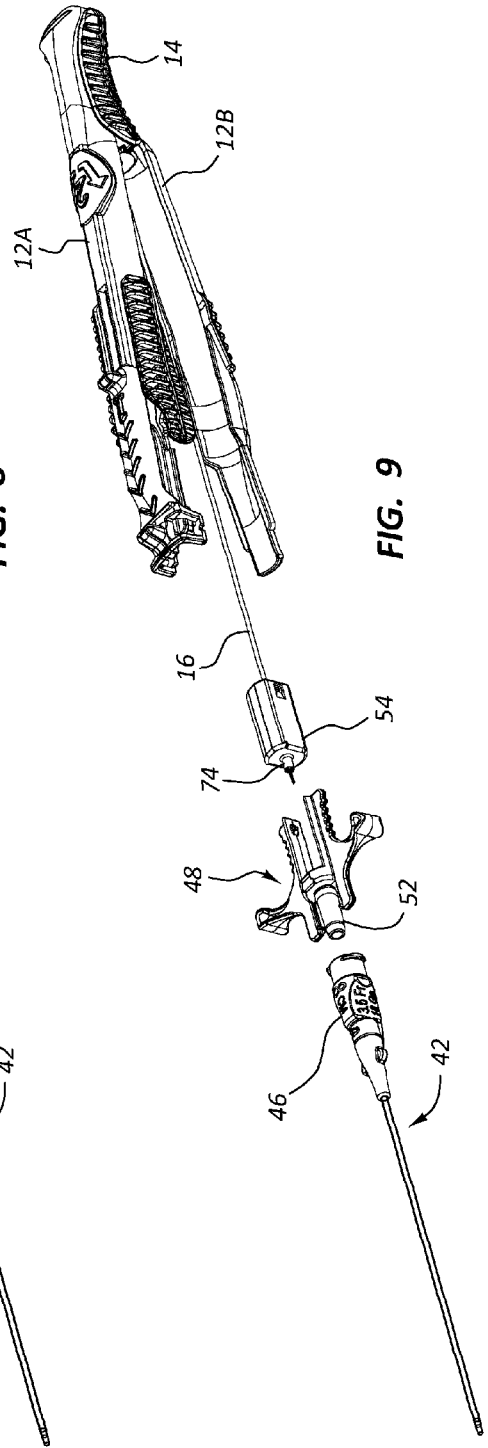
FIG. 9 shows one stage of use of the catheter insertion tool of FIGS. 1A and 1B according to one embodiment.

Note that, as shown in FIGS. 7A and 7B, during removal of the catheter from within the housing 12 of the insertion tool 10, the catheter slides distally along the needle 16 until the distal needle tip is received into the safety housing 54 and engaged with the needle safety component 56. FIG. 8 shows that the insertion tool 10 can then be separated from the catheter 42, leaving the handle 48 still attached to the catheter hub 46. As mentioned, the handle 48 includes the valve 52 interposed between the catheter hub 46 and the handle 48. Upon removal of the needle 16 and safety housing 54 from the catheter 42, the valve 52 occludes the catheter lumen so as to prevent inadvertent blood spillage from the catheter hub 46. As shown in FIG. 9, the handle 48 can be removed from engagement with the catheter hub 46 via pulling, twisting, etc., so as to disengage the teeth 50C of the handle from the hub. An extension leg can be attached to the catheter hub and the catheter 42 dressed down, per standard procedures. Then housing 12 and handle 48 of the insertion tool 10 can be discarded.

Figure 10C:
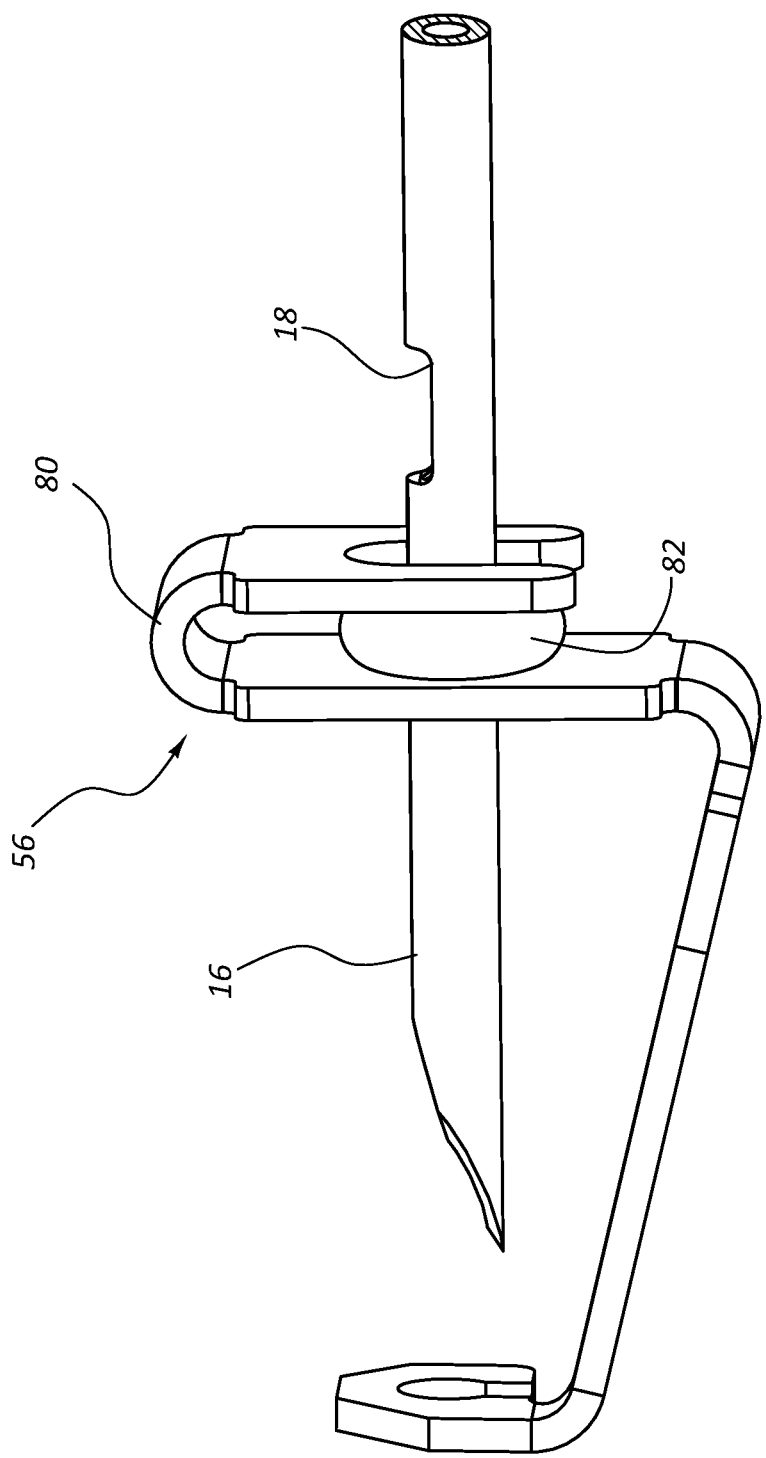
Figure 11A:
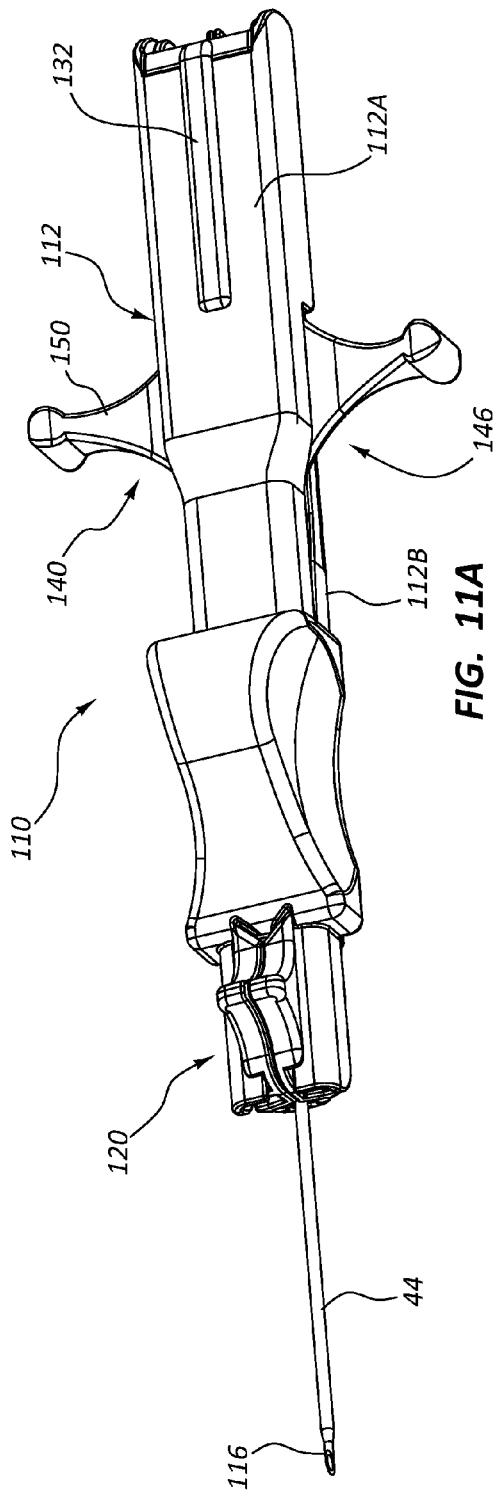
Figure 11B:
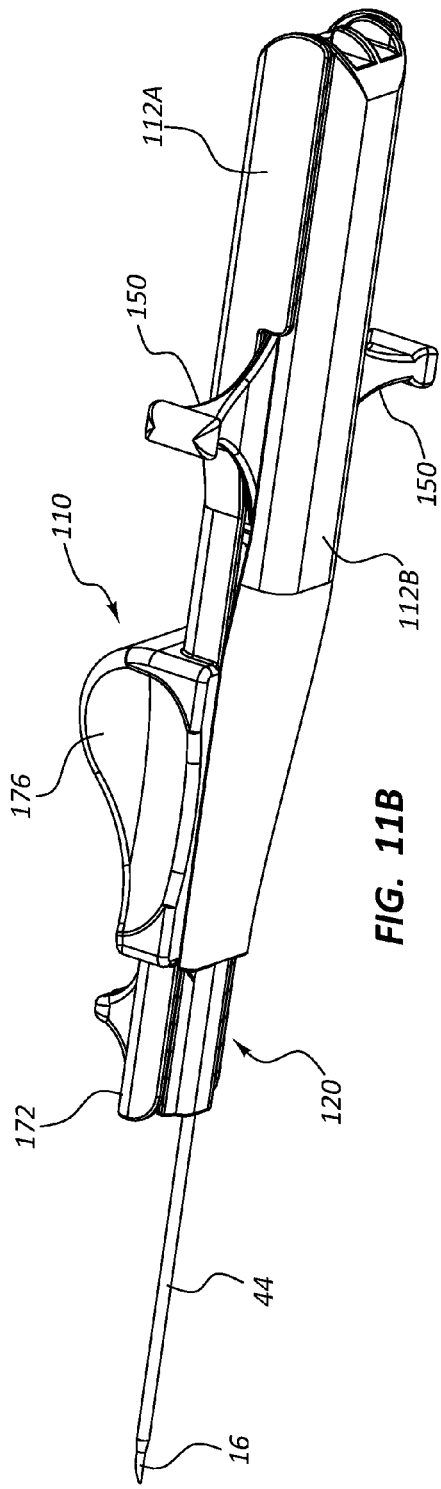

FIGS. 10A-10C give further details regarding the safety housing 54, as well as the needle safety component 56 and its interaction with the needle 16 in isolating the distal end thereof. As shown, the safety housing 54 is configured to enable the needle 16 to pass therethrough during use of the insertion tool 10, as has been described, exiting the housing via the extension 74 on the distal end of the housing. The cap 58 is placed into the proximal end of the safety housing 54 and is configured to support the needle safety component 56 such that he needle 16 initially passes through the safety housing, the cap, and the needle safety component. Note that the extension 74 of the safety housing 54 in the present embodiment extends into the valve 52 so as to open the valve during use of the insertion tool 10, which eliminates undesired friction between the valve and the needle.

FIG. 10C shows that the needle safety component 56 includes a bent body, or binding element 80 through which the needle initially extends, and a friction element 82. As seen in FIG. 10A, when the needle 16 is withdrawn from the catheter 42 (FIG. 8), the distal tip of the needle is withdrawn proximally through the extension 74 and past the distal portion of the needle safety component such that the needle is no longer in contact therewith. This enables the friction element 82 to cause the binding element 80 to cant slightly, thus binding the needle 16 in place and preventing its further travel with respect to the safety housing 54 and isolating the needle distal tip within the housing so as to prevent inadvertent needle sticks. In the present embodiment the friction element 82 includes a suitably sized O-ring. Suitable O-rings can be acquired from Apple Rubber Products, Lancaster, N.Y., for instance. Note that further details regarding the needle safety component, its operating principles, and similar devices are disclosed in U.S. Pat. Nos. 6,595,955, 6,796,962, 6,902,546, 7,179,244, 7,611,485, and 7,618,395, each of which is incorporated herein by reference in its entirety. Of course, other needle safety devices can be employed to isolate the distal end of the needle.

Reference is now made to FIGS. 11A-13B in describing a catheter insertion tool 110 according to one embodiment. Note that in this and succeeding embodiments, various features are similar to those already described in connection with the above embodiment. As such, only selected aspects of each embodiment to follow will be described.

The insertion tool 110 includes a housing 112 defined by a top housing portion 112A and a bottom housing portion 112B that together partially enclose the catheter 42. A needle hub 114 supporting a distally extending needle 116 is included for disposal within the housing 112 and positioned such that the catheter tube 44 of the catheter 42 is disposed over the needle. Note that partial enclosure of the catheter by the insertion tool in this and other embodiments enables a clinician to manipulate the insertion tool with hands that are closer to the distal end of the needle than what would otherwise be possible.

FIGS. 13A and 13B give further details regarding the needle hub 114, which is attached to the top housing portion 112A. A needle holder 126, included on a distal end of the needle hub 114, receives the proximal end of the needle 116 therein. The needle 116 is secured within the needle holder 126 via adhesive, welding, or other suitable manner. Extensions 128 are included on opposite sides of the needle holder 126 and are configured to be slidably received within corresponding slots 130 defined on the sides of the bottom housing portion 112B. Such engagement enables the bottom housing portion 112B to slide distally with respect to the top housing portion 112A.

A top rail 132 is included on the needle hub 114 and is configured to engage a corresponding slot 134 defined in the proximal portion of the top housing portion 112A so as to secure the needle hub to the top housing portion. A lock out arm 136 is also included with the needle hub 114 and positioned to engage the back plate 124 when the bottom housing portion 112B is slid distally to extend the guidewire from the needle 116, thus preventing its retraction. Note that the guidewire 122 initially distally extends from the back plate 124 and through the needle holder 126 and needle 116, as best seen in FIG. 11D.

A guidewire advancement assembly 120 is included to selectively advance a guidewire 122, initially disposed within the lumen of the needle, distally past the distal end of the needle 116. The guidewire advancement assembly 120 includes the bottom housing portion 112B to which the guidewire 122 is attached at a proximal back plate 124 thereof. As will be seen, the bottom housing portion 112B is distally slidable with respect to the top housing portion 112A to enable selective distal advancement of the guidewire 122.

Figure 12A:
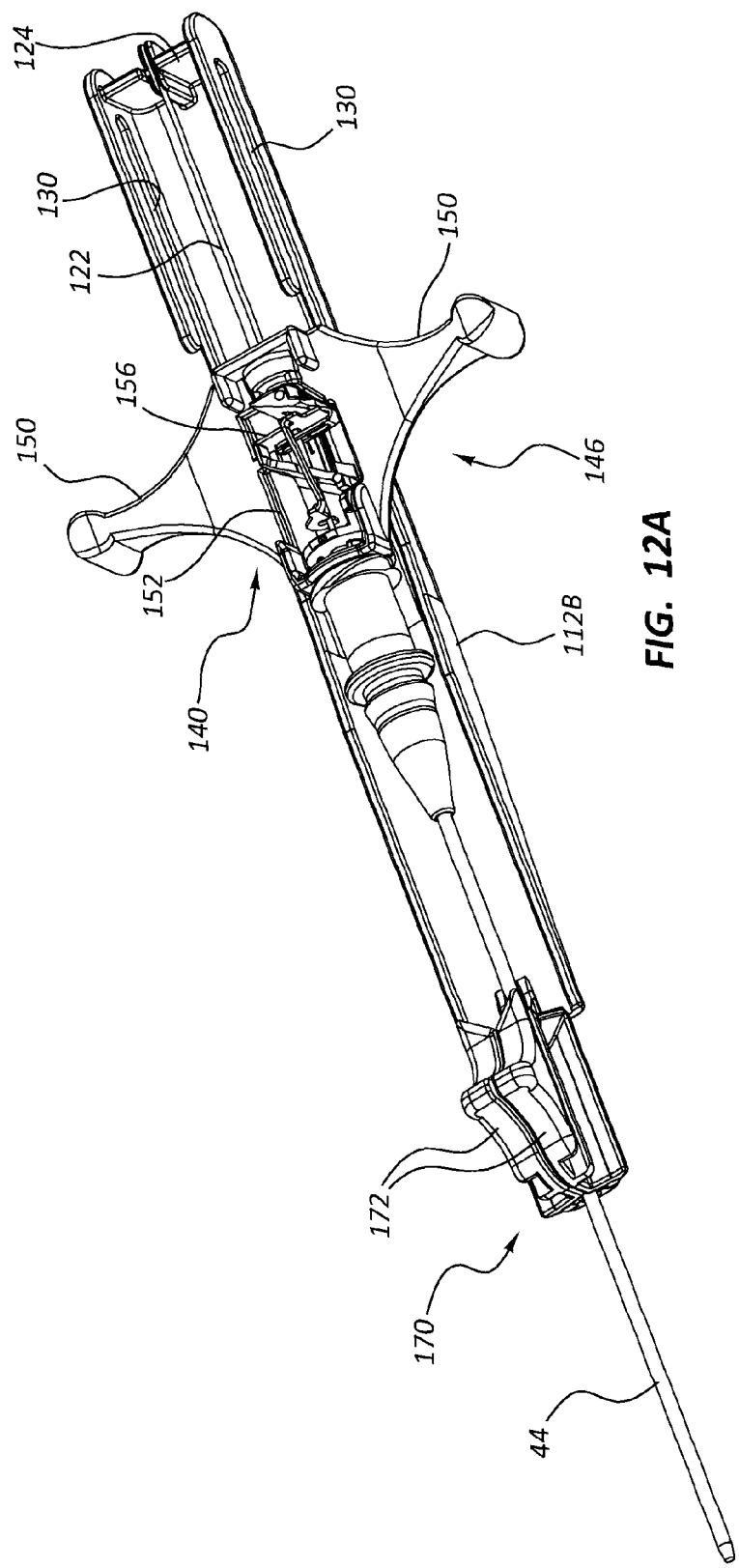
FIGS. 12A and 12B are various views of a portion of the catheter insertion device of FIGS. 11A-11D.
Figure 12B:
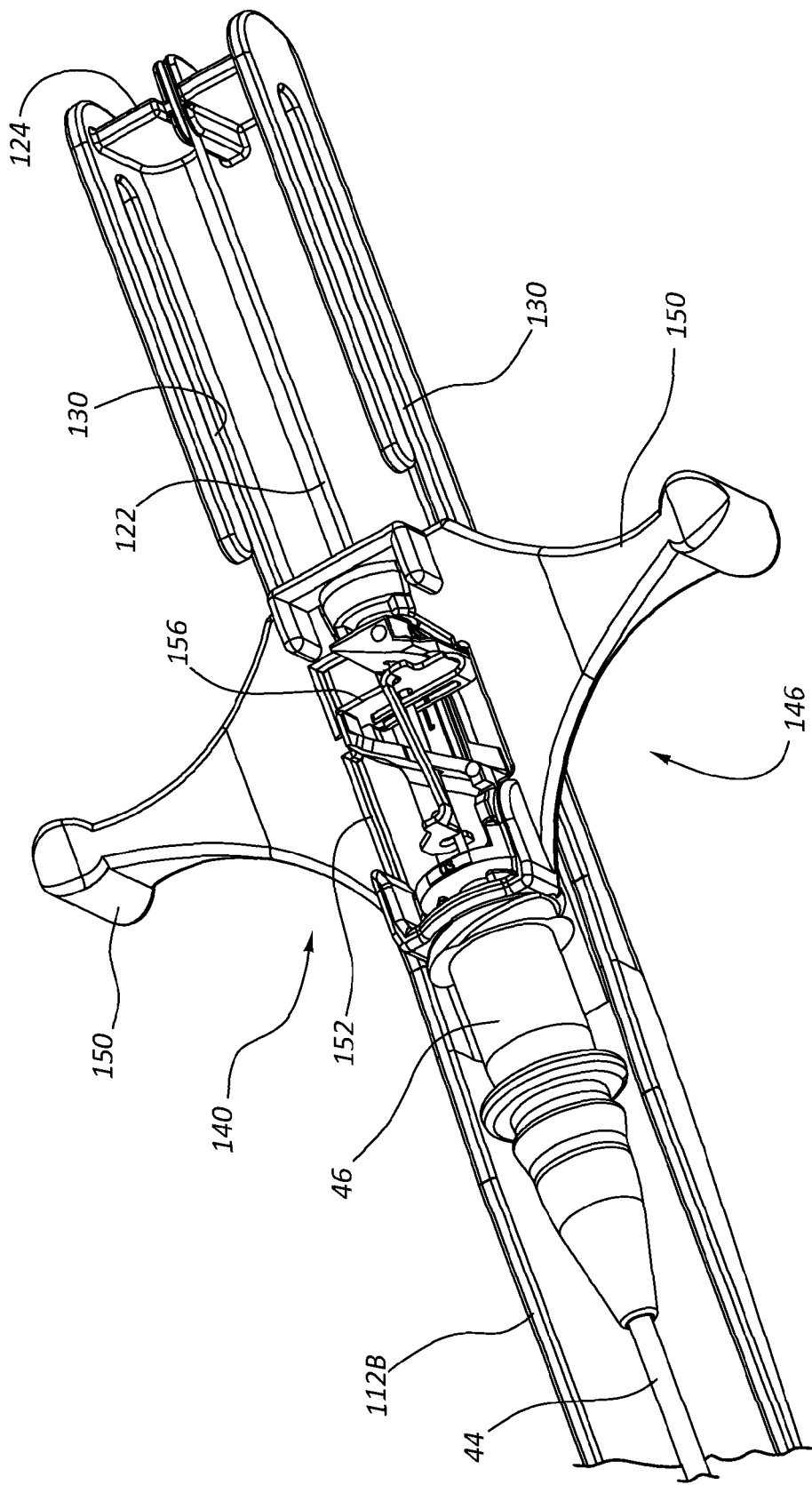

The insertion tool 110 further includes a catheter advancement assembly 140 for selectively advancing the catheter 42 over the needle 116. The advancement assembly 140 includes a handle 146 initially and slidably disposed between the top and bottom housings 112A and 112B and removably attached to the hub 46 of the catheter 42. As best seen in FIGS. 12A and 12B, the handle 146 includes two arms 150 for allowing a user to selectively slide the handle in order to advance the catheter 42. The handle 146 further includes a recess 152 in which is placed a needle safety component 156 for isolating the distal tip of the needle 116 when the needle is withdrawn from the catheter 42. Further details regarding the needle safety component are disclosed in U.S. Pat. Nos. 6,595,955, 6,796,962, 6,902,546, 7,179,244, 7,611,485, and 7,618,395, each incorporated by reference above.

Figure 14A:
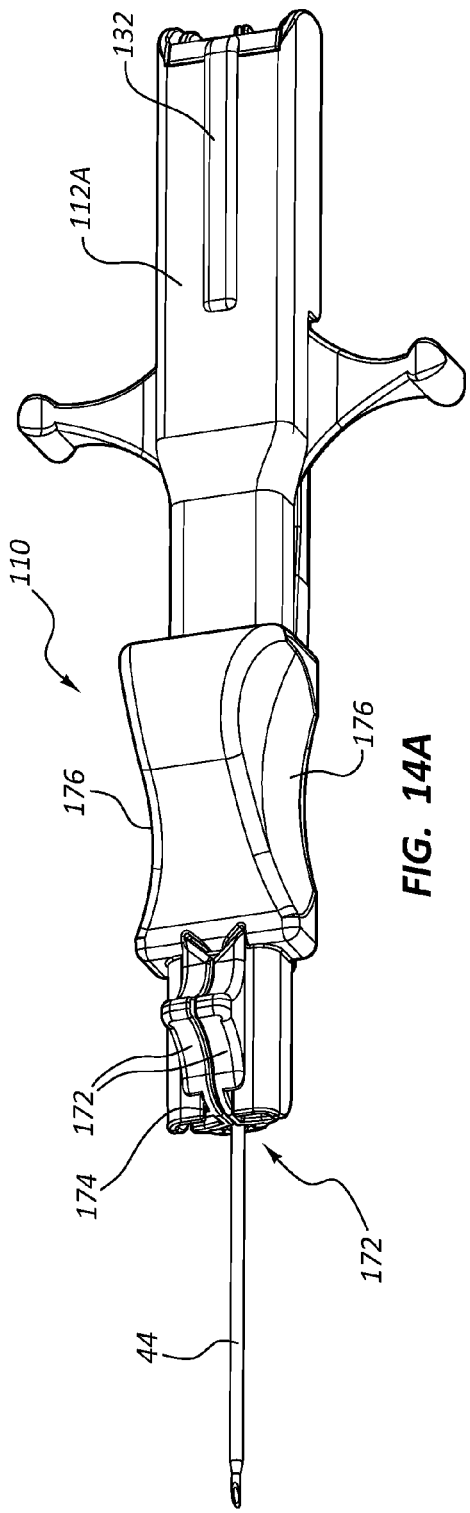
Figure 14B:
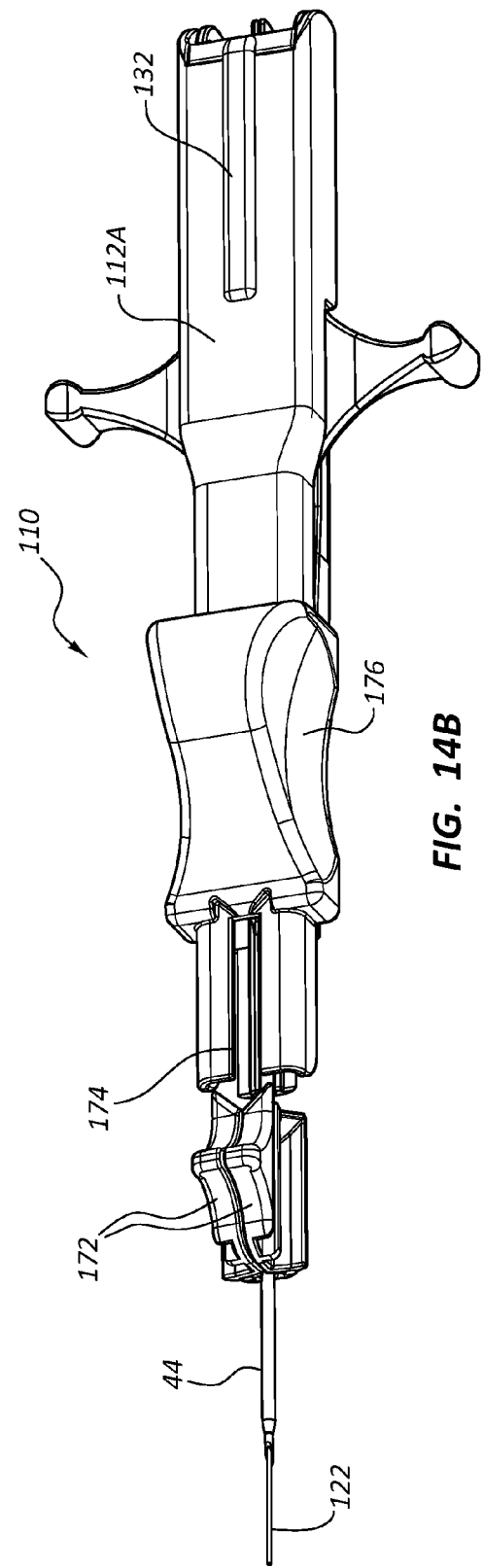

The insertion tool 110 further includes a support structure 170 for stabilizing the needle 116 proximate the distal end of the housing 112. The support structure 170 in the present embodiment includes two flaps 172 that are hingedly connected to the distal portion of the bottom housing portion 112B. When closed as seen in FIGS. 11D and 12A, the flaps 172 serve to stabilize the needle 116 to assist the user of the insertion tool 110 in inserting the needle into the patient. When open (FIG. 14D), the flaps 172 provide an opening to enable the catheter hub 46 to be removed from the distal end of the housing 112, as will be detailed further below. Before the bottom housing portion 112B is slid with respect to the top housing portion 112A, the flaps 172 are disposed in a track 174 defined by the top housing portion. Other types and configurations of support structures can also be employed. The insertion tool 110 further includes gripping surfaces 176 on either side of the housing 112 to aid in use of the tool during catheter insertion procedures, detailed below.

FIGS. 14A-14E depict various stages of use of the insertion tool 110 in inserting a catheter into a patient. With the insertion tool 110 in the configuration shown in FIG. 14A, vascular access is achieved with the needle 116 via user insertion of the needle into the patient at an insertion site. Confirmation of vessel access can be achieved via the observation of blood flashback via a distal notch in the needle 116, as described in the previous embodiment, or in other suitable ways.

Once the distal portion of the needle 116 is disposed within a vessel of the patient, the guidewire 122 is extended past the distal end of the needle and into the vessel by distally advancing the bottom housing portion 112B. Such advancement is achieved in the present embodiment by placing a user's fingers on the folded-up flaps 172 of the bottom housing portion 112B and pushing the flaps distally, thus extending the guidewire 122. The guidewire 122 is advanced until fully extended. The lock out arm 136 of the needle hub 114 then engages the back plate 124 of the bottom housing portion 112B and prevents retraction of the guidewire 122.

At this stage, the handle 146 of the catheter advancement assembly 140 is distally advanced, by a user grasping of one or both arms 150 thereof, so as to distally advance the catheter 42 through the insertion site and into the patient vasculature. This is shown in FIG. 14C, wherein the catheter tube 44 is shown distally advancing over the needle 116 and the guidewire 122.

As shown in FIG. 14D, continued distal advancement of the catheter 42 causes the catheter hub 146 to urge the flaps 172 to open, thus providing a suitable opening through which the hub may pass from the insertion tool housing 112. Note that the flaps 172 are shaped such that contact with the catheter hub 46 urges each flap to fold outward, as seen in FIG. 14D. Note also that the flaps 172 are no longer disposed within the track 174 due to full distal advancement of the guidewire 122 via finger pressure applied to the flaps 172 as described above.

Figure 14E:
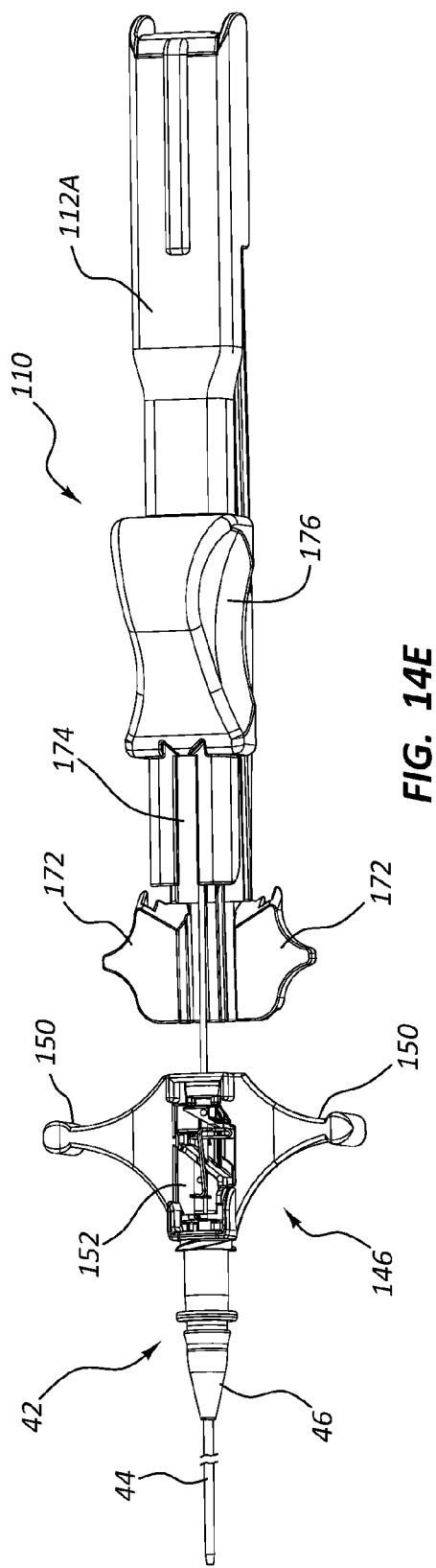
Figure 14F:
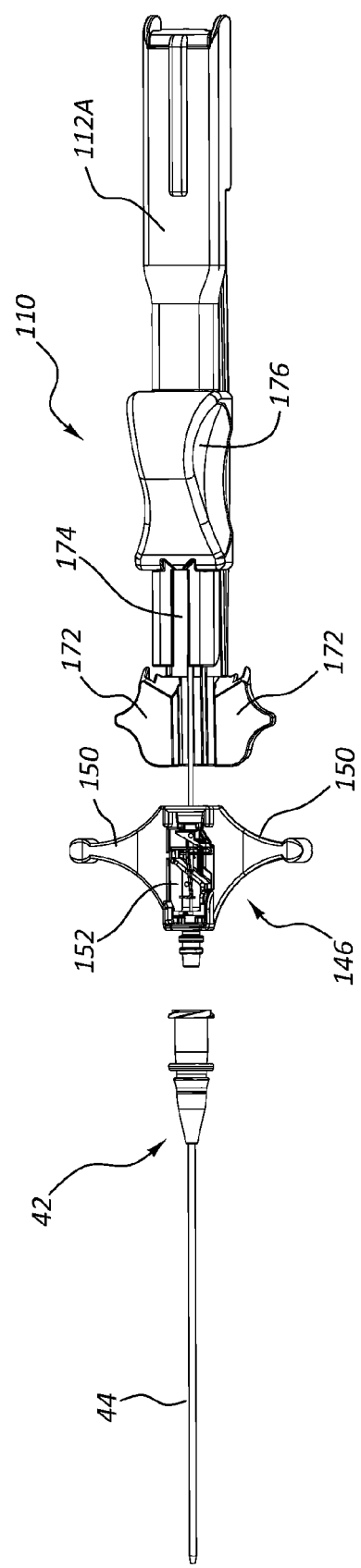

FIG. 14E shows that, with the flaps no longer engaged within the track 174, the top housing portion 112A and bottom housing portion 112B are able to separate at the distal ends thereof such that the handle 146, still attached to the catheter hub 46, can separate from the housing 112. Though not shown at this stage, the needle safety component 156 disposed in the recess 152 of the handle 146 isolates the distal end of the needle 116. The handle 146 can then be manually removed from the catheter hub 46 (FIG. 14F), and placement and dressing of the catheter 42 can be completed. The insertion tool 110, including the needle 116 isolated by the needle safety component 156 of the handle 146, can be safely discarded.

Figure 15A:
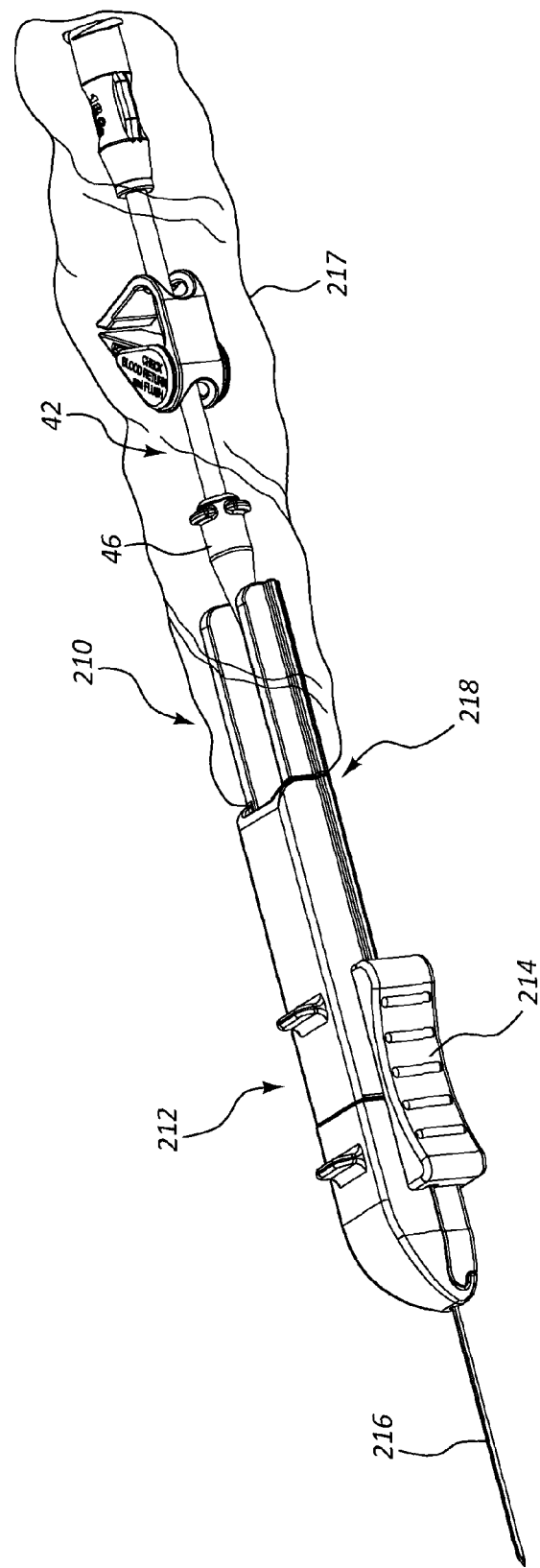
FIGS. 15A and 15B are various views of a catheter insertion device according to one embodiment.

Reference is now made to FIGS. 15A-18 in describing a catheter insertion tool 210 according to one embodiment. The insertion tool 210 includes a housing 212 defined by a top housing portion 212A and a bottom housing portion 212B that together partially enclose the catheter 42. A sliding needle hub 214 supporting a distally extending hollow needle 216 is slidably attached to the housing 212. In particular, the needle hub 214 includes tracks 214A that slidably engage corresponding rails 218 defined on the top and bottom housing portions 212A, 212B in a manner described further below. As shown in FIG. 15A, the needle hub 214 is positioned distally with respect to the housing 212 such that the needle 216 extends through a needle channel 224 (FIG. 18) and out a hole defined in a distal end of the top housing portion 212A so that the needle is positioned as shown in FIG. 15A.

Figure 15B:
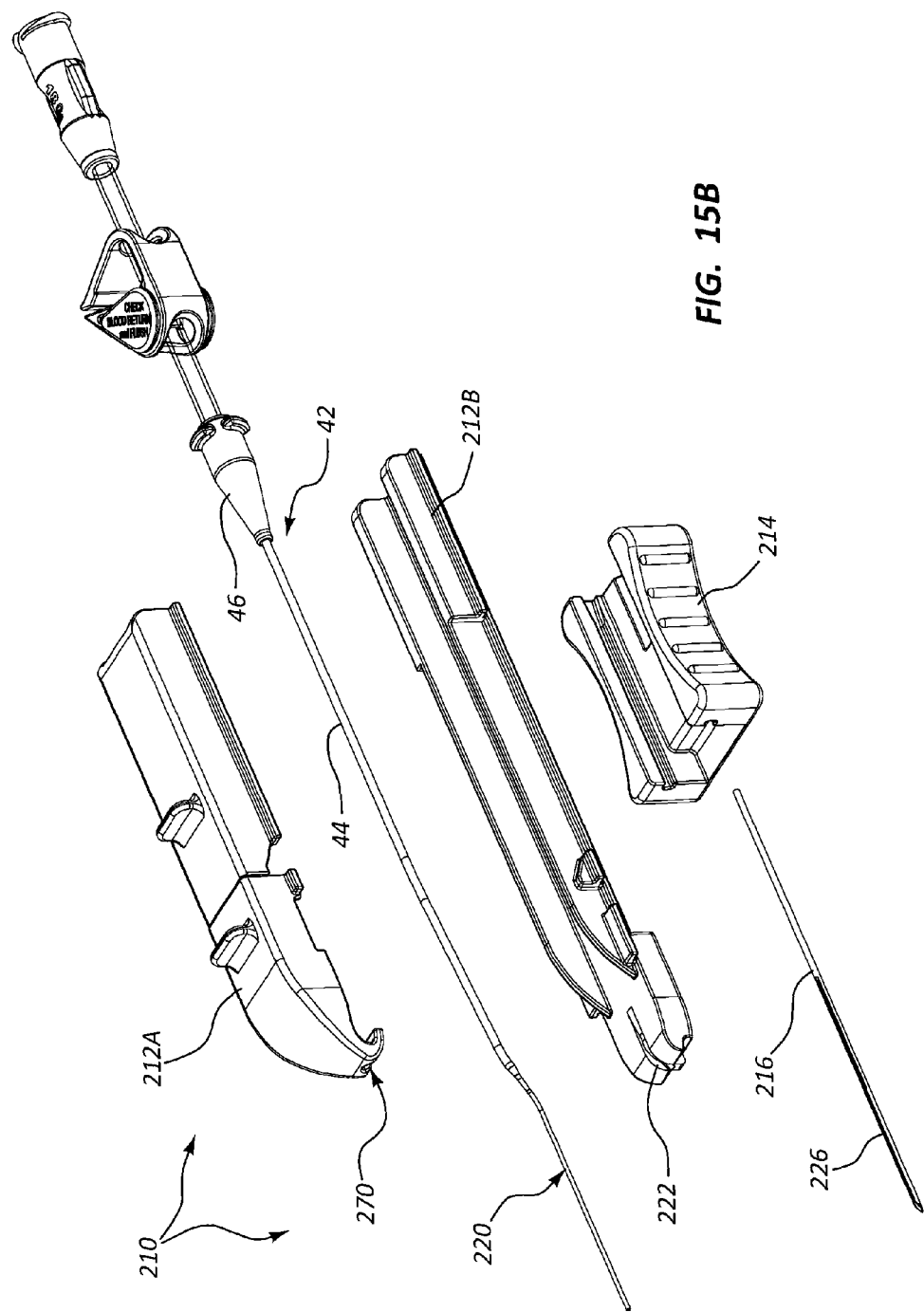
Figure 16:
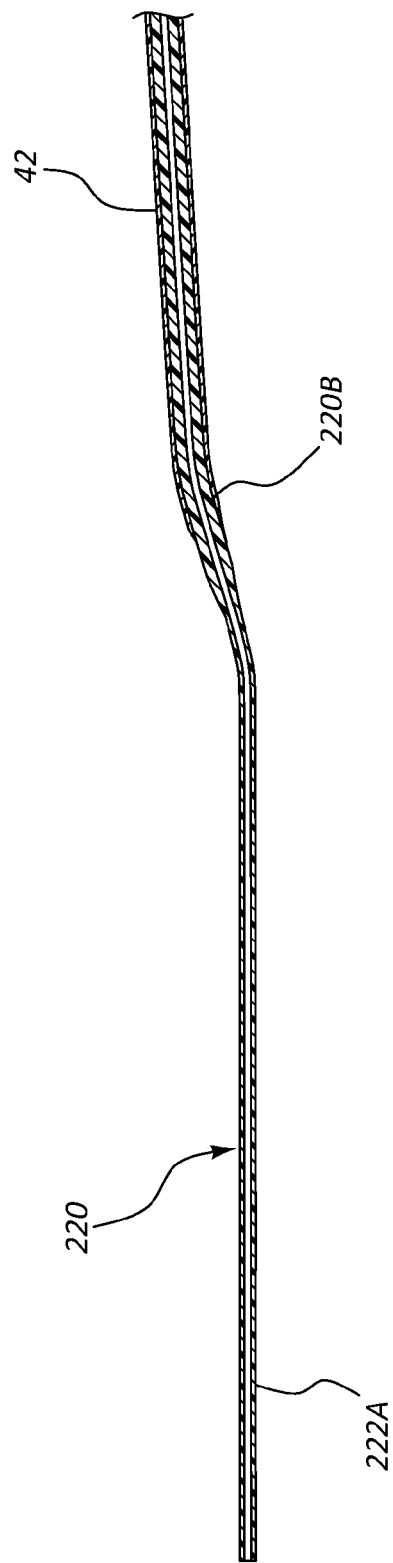
FIG. 16 is a cross sectional side view of an integrated guidewire/dilator for use with the catheter insertion device of FIGS. 15A and 15B.

As seen in FIG. 15A, the housing 212 of the insertion tool 210 encloses a portion of the catheter 42. An integrated guidewire/dilator 220 is included and disposed within the lumen of the catheter tube 44, as shown in FIGS. 15B and 16. The guidewire/dilator 220 includes a distal guidewire portion 220A and a proximal dilator portion 220B. So configured, the guidewire/dilator 220 can not only serve as a guidewire in directing the catheter tube 44 through the insertion site of the patient into the accessed vessel, but can dilate the insertion site in advance of catheter insertion therethrough. In other embodiment, no guidewire/dilator need be used. In one embodiment, it is appreciated that the guidewire/dilator 220 can proximally extend through the entire catheter 42 and include on a proximal end thereof a luer cap connectable to a proximal luer connector of the catheter. Note also that FIG. 15A shows a sterile bag 217 attached to the housing 212 so as to cover and isolate the proximal portion of the catheter 42. For clarity, the bag 217 is included only in FIG. 15A, but could be included with insertion tools of varying configurations so as to protect and isolate portions of the catheter.

As seen in FIGS. 17A-17C, the needle 216 includes a longitudinally extending needle slot 226 extending from a beginning point along the length of the needle to the distal end thereof. FIG. 17B shows that the slot 226 can be optionally wider in a proximal portion thereof relative to more distal slot portions. So configured, the needle slot 226 enables the guidewire/dilator 220 to be inserted into, slid relative to, and removed from the needle 216 during operation of the insertion tool 210, described below. Note that the needle slot can extend the entire length of the needle, in one embodiment.

FIG. 18 shows the manner of entry of the guidewire/dilator 220 into the slot 226 of the needle 216 according to one embodiment, wherein the guidewire/dilator extends distally along a guide channel 222 defined in the top housing portion 212A and into the hollow needle 216, which is disposed in the needle channel 224, via the needle slot. (The guide channel 222 is also seen in FIG. 15B.) In this way, the guidewire/dilator 220 can be distally slid through the hollow needle 216 so as to extend beyond the distal needle end while still being able to be removed from the needle via the slot 226 when the guidewire/dilator and needle are separated from one another, as will be seen.

Figure 19:
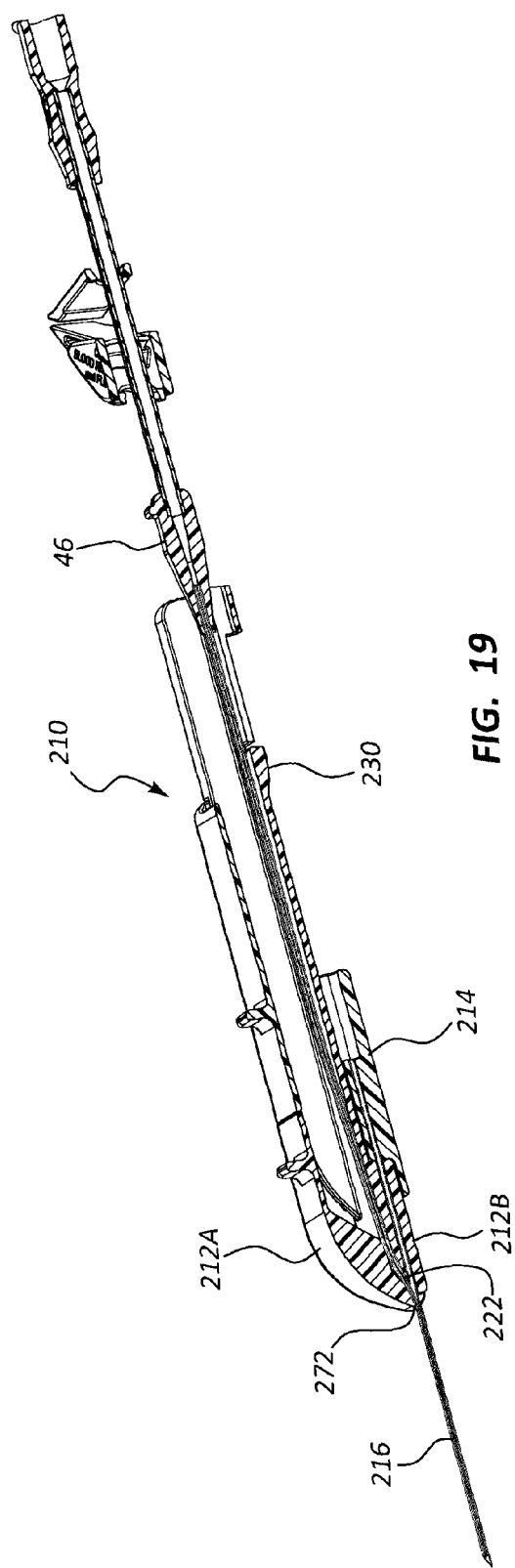
FIG. 19 shows one stage of use of the catheter insertion tool of FIGS. 15A and 15B according to one embodiment.
Figure 22:
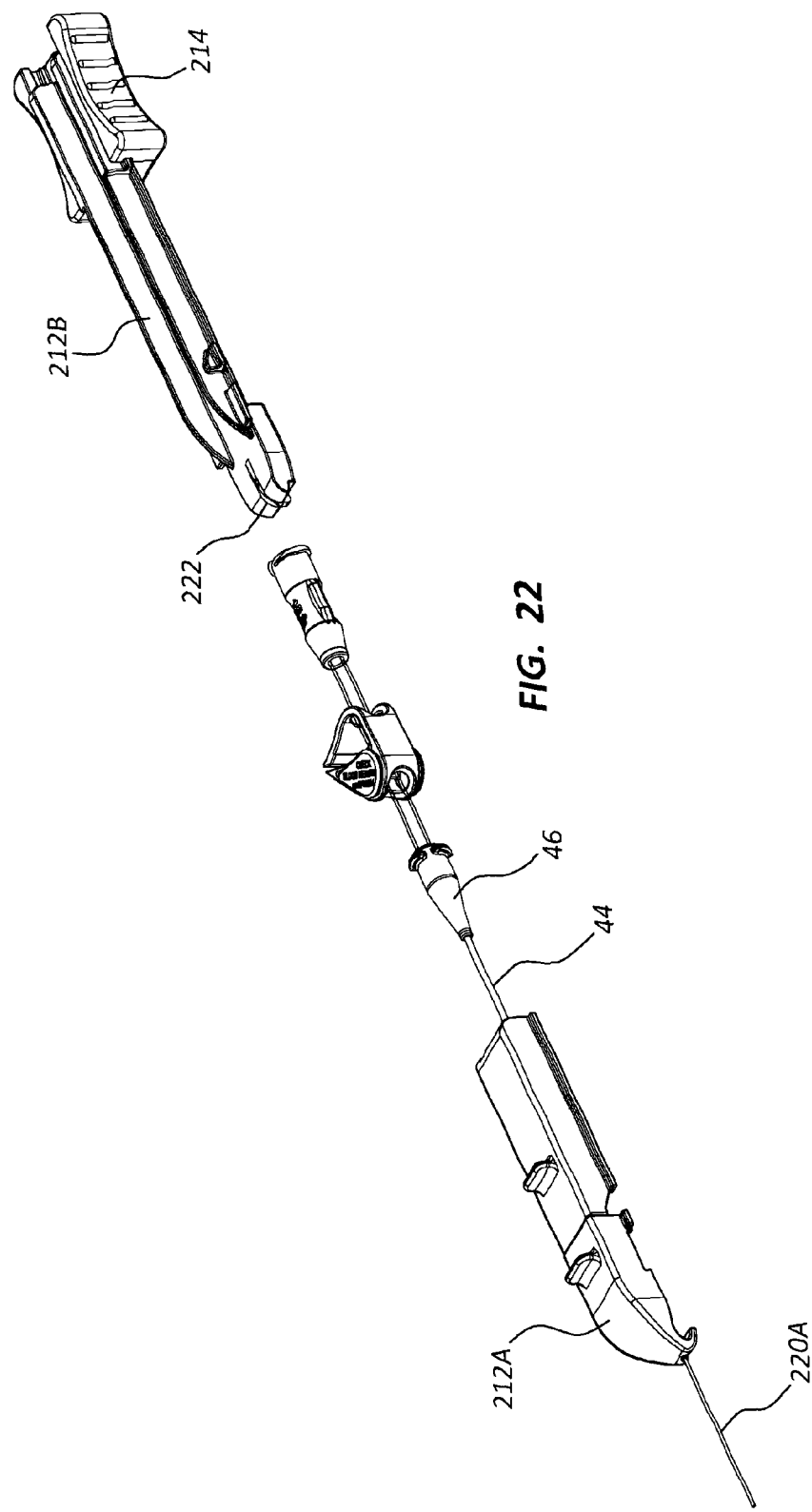
FIG. 22 shows one stage of use of the catheter insertion tool of FIGS. 15A and 15B according to one embodiment.
Figure 23:
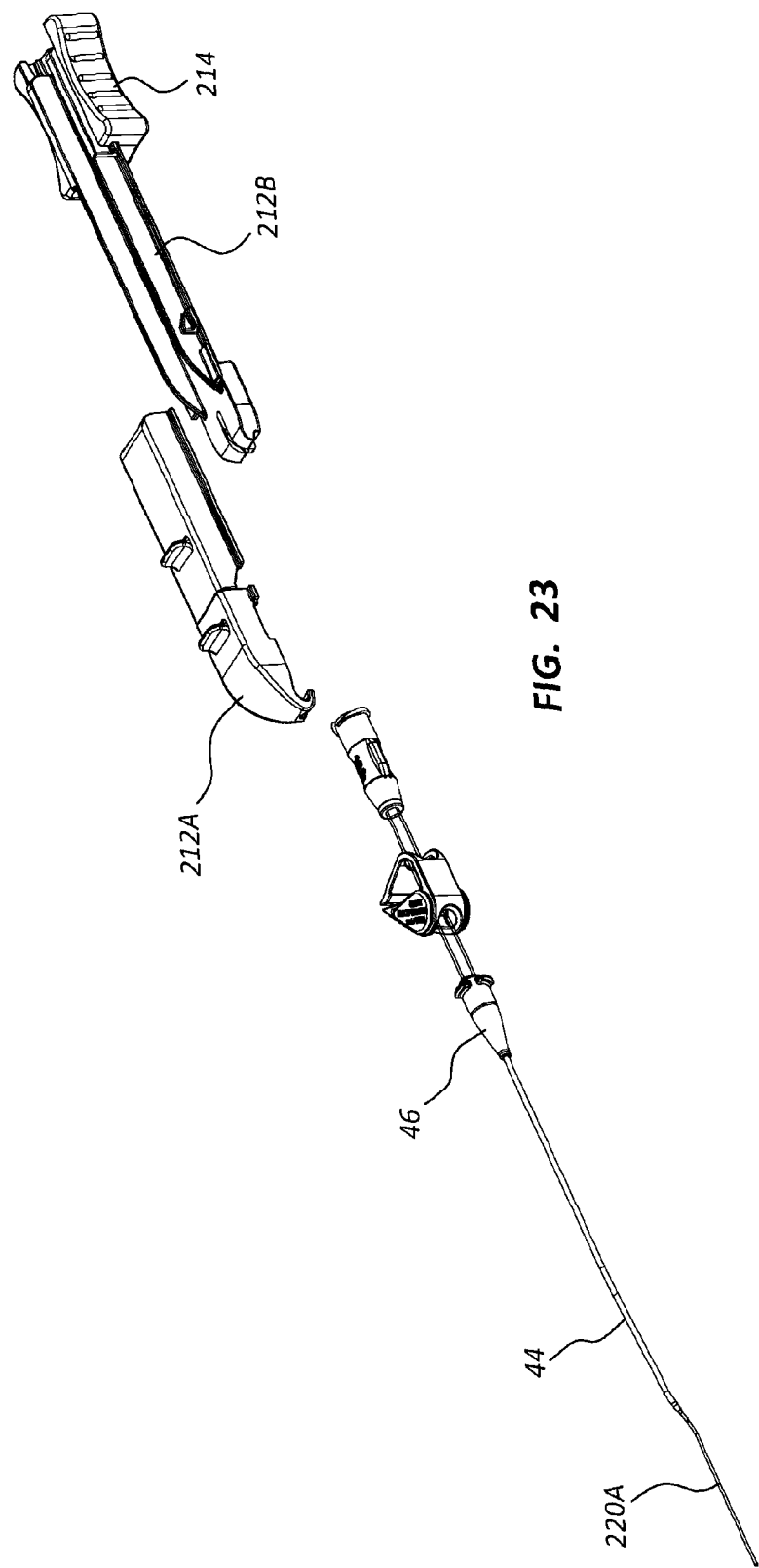
FIG. 23 shows one stage of use of the catheter insertion tool of FIGS. 15A and 15B according to one embodiment.

FIG. 18 also shows a support structure 270 for stabilizing the needle 216, including an interface 272 defined by portions of the top housing portion 212A and the bottom housing portion 212B about the hole through which the needle extends. Of course, other support structures can be employed to provide stability to the needle to assist in inserting the needle into the patient vasculature. FIG. 19 shows details of a lockout 230 for the needle hub 214, included on the bottom housing portion 212B, for preventing further movement of the needle hub after it has been retracted, as described below.

FIGS. 19-24 depict various stages of use of the insertion tool 210 in inserting a catheter into a patient. With the insertion tool 210 in the configuration shown in FIG. 19, vascular access is achieved with the needle 216 via user insertion of the needle into the patient at an insertion site.

Once the distal portion of the needle 116 is disposed within a vessel of the patient, the guidewire/dilator 220 is manually fed through the hollow needle 216 so as to extend past the distal end of the needle and into the vessel. Such advancement is achieved in the present embodiment by distally moving the housing 212 and catheter 42 together while keeping the needle hub 214 stationary. The guidewire 122 is advanced distally a suitable distance, which in the present embodiment, includes advancement until a distal end of the housing 212 arrives at the skin insertion site.

FIGS. 20A and 20B show that after the guidewire/dilator 220 has been distally extended into the vessel, the needle 216 is retracted from the vessel by proximally sliding the needle hub 214 along rail portions 218A disposed on the top housing portion 212A. Proximal sliding of the needle hub 214 continues until the hub engages the rail portions 218B of the bottom housing portion 212B and is fully slid to the proximal end of the housing 212, as shown in FIGS. 21A and 21B. The needle hub 214 engages the lock out 230 (FIG. 20B) so as to prevent future distal movement of the needle hub or needle 216. In this position, the needle 216 is fully retracted into the insertion tool housing 212 such that the distal end of the needle is safely isolated from the user (FIG. 21B). Note that in one embodiment a needle safety component can be added to the insertion tool to further isolate the tip of the needle. Note that the distal portion of the guidewire/dilator 220 remains in the vessel of the patient, having been able to separate from the needle 216 during retraction thereof via the needle slot 226.

At this stage, the bottom housing portion 212B (FIG. 22) and the top housing portion 212A (FIG. 23) are removed from the catheter 42. The catheter 42 can then be inserted through the insertion site and into the vessel of the patient. Note that the guidewire/dilator 220 is still disposed within the catheter tube 44 and that the dilator portion assists the distal end of the catheter tube to enter the vessel by gradually enlarging the insertion site and the vessel entry point.

Figure 24:
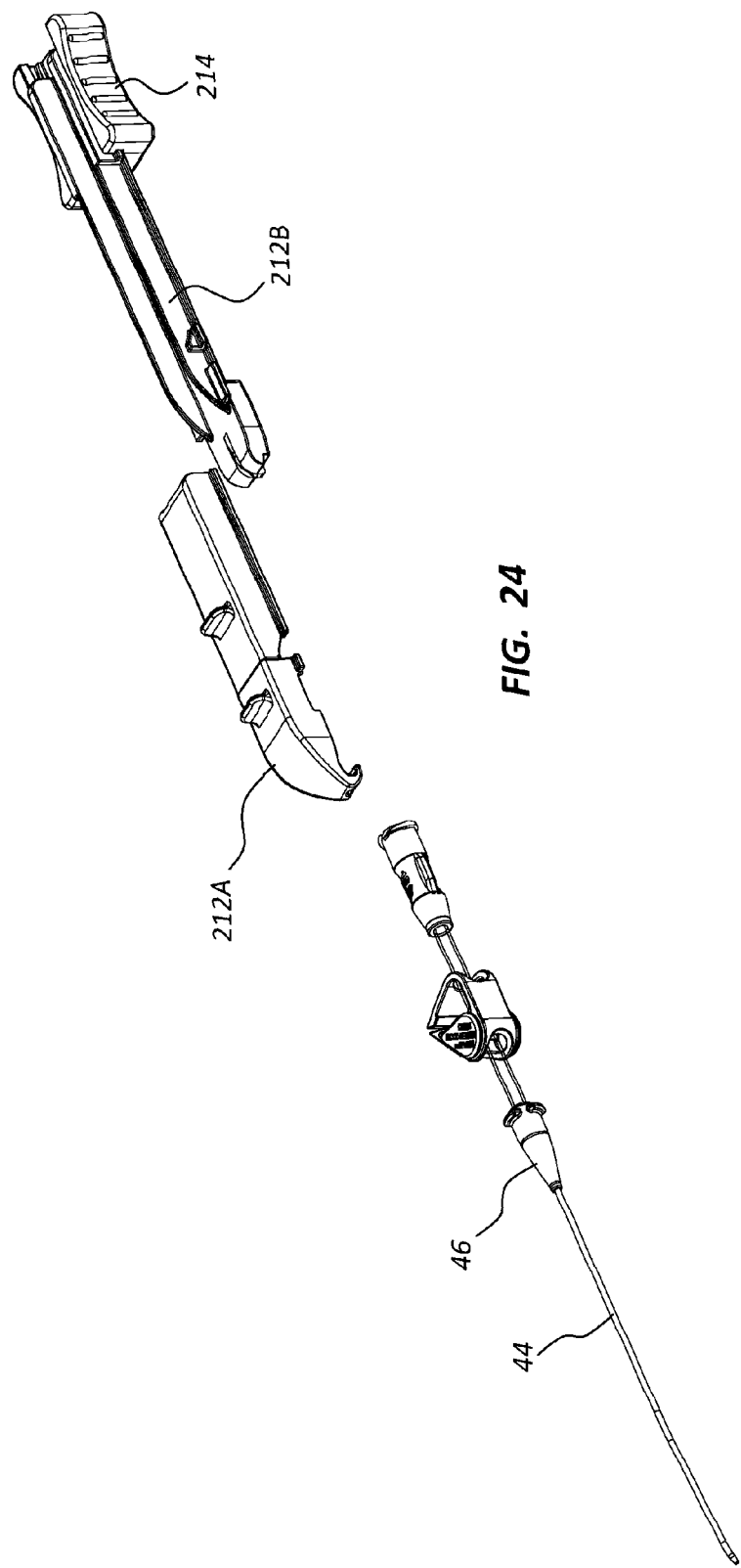
FIG. 24 shows one stage of use of the catheter insertion tool of FIGS. 15A and 15B according to one embodiment.

As mentioned, in one embodiment, the proximal portion of the catheter 42, including the hub 46 and connected extension leg, is covered by a sterile bag, which is attached to the housing 212. The sterile bag can be removed after the catheter is fully inserted into the patient vessel or can be removed when the housing portions 212A and 212B are removed. In FIG. 24, the guidewire/dilator 220 is then removed from the catheter 42 and the catheter dressed and finalized for use. The guidewire/dilator 220 and other portions of the insertion tool 210 are discarded.

Figure 26:
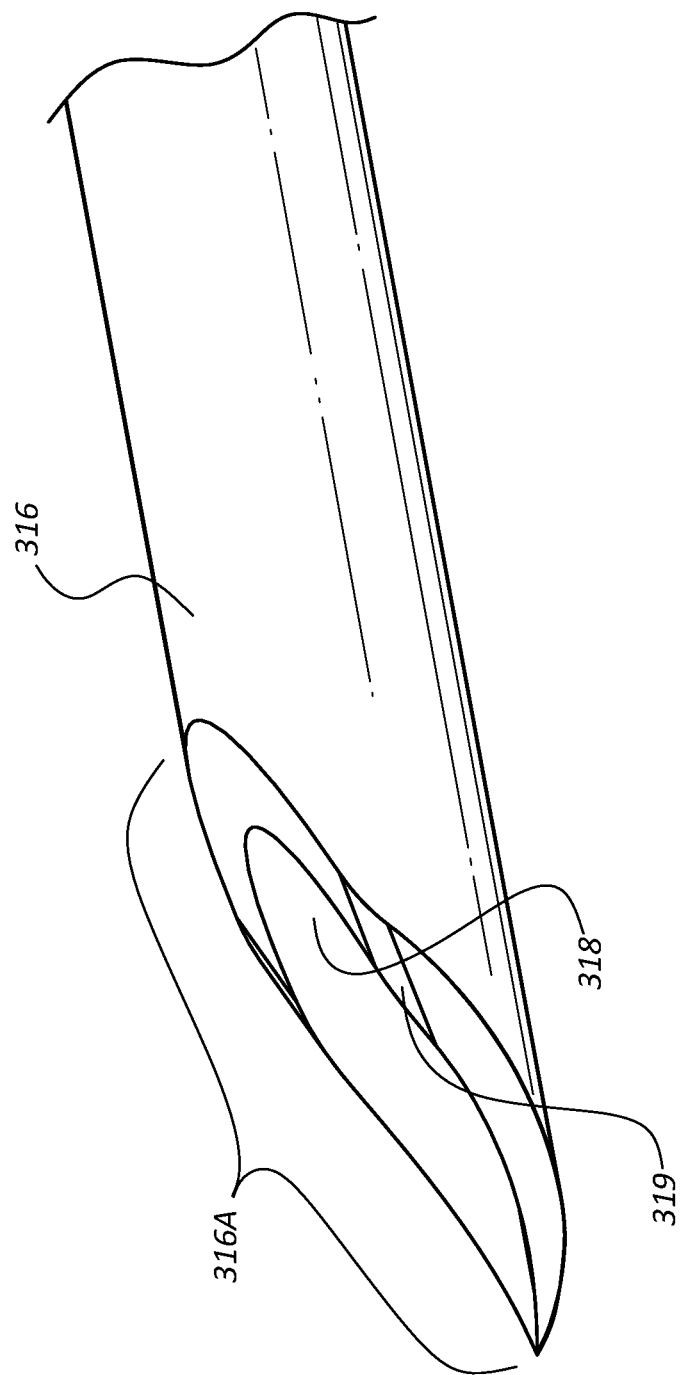
FIG. 26 is a perspective view of a needle distal tip design according to one embodiment.

FIGS. 25A and 25B depict details regarding a needle blunting system for isolating a distal end 316A of a hollow needle 316, according to one embodiment. As shown, the needle distal end 316A includes a bevel that is configured such that its cutting surfaces are disposed at an inner diameter 318 of the needle 316. Thus, when a suitably sized guidewire 320 is distally extended past the distal end 316A of the needle 316, the cutting surfaces of the needle are blocked by the proximity thereto of the guidewire, thus safely isolating the needle end from a user. In addition, blunting the distal end 316A of the needle 316 in this manner prevent the needle end from damaging sensitive inner walls of the vessel after the needle tip has been inserted herein. At this point, a distal end 44A of the catheter tube 44 can then be distally advanced over the needle 316 and guidewire 320. FIG. 26 depicts a needle end bevel 316A according to another embodiment, including an additional fillet component 319. Such a blunting system can be employed in one or more of the insertion tools described herein.

Figure 27:
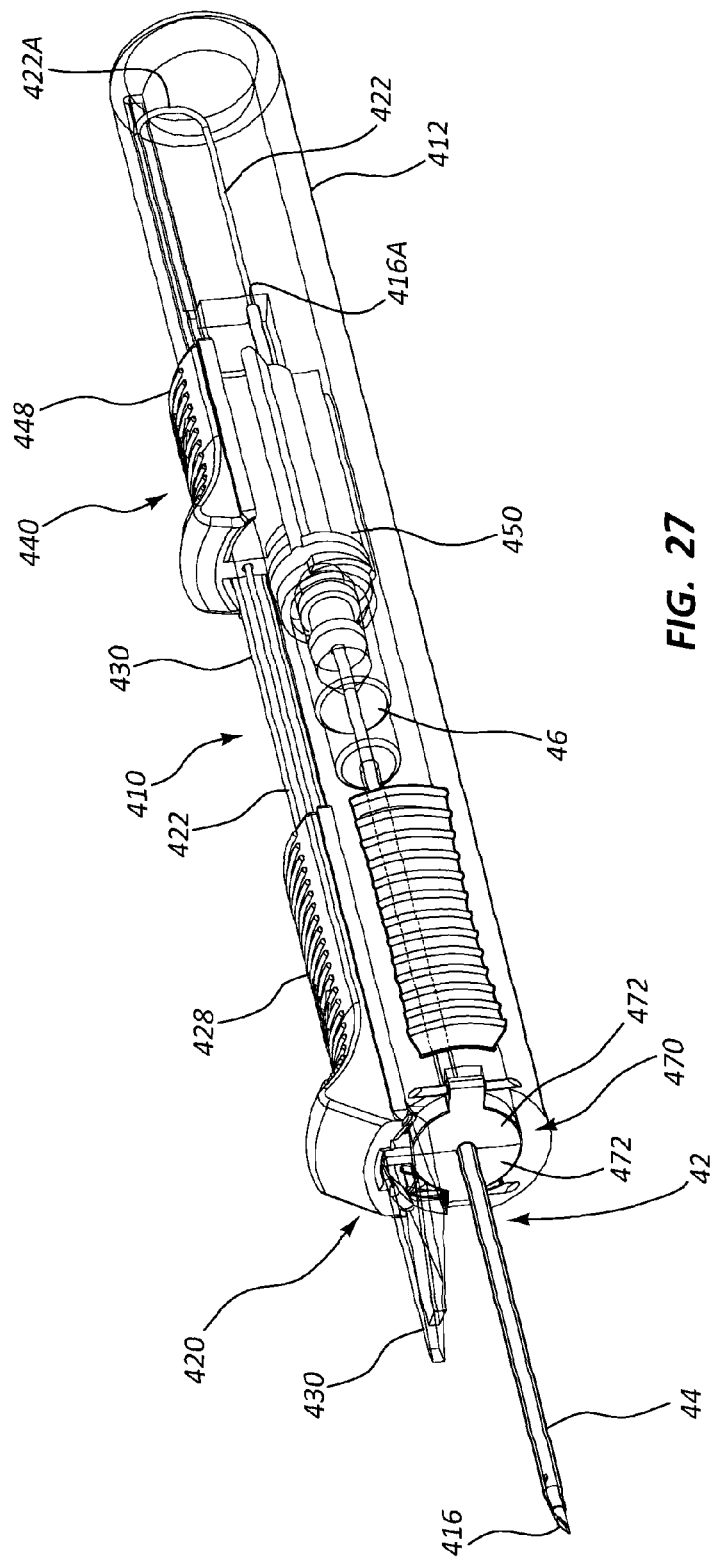
FIG. 27 is a perspective view of a catheter insertion tool according to one embodiment.

Reference is now made to FIG. 27 in describing a catheter insertion tool 410 according to one embodiment. The insertion tool 410 includes a housing 412 that partially encloses the catheter 42. A distally extending hollow needle 416 is disposed with the housing 412 such that the needle extends out the distal end of the housing 412

A guidewire advancement assembly 420 is shown for selectively advancing a guidewire 422, including a slide 428 that slides along a track 430 defined in the housing 412. The guidewire 422 is attached to the slide 428 and extends proximally within the housing 412 until it bends, forming a guidewire bend 422A, toward the distal end of the housing and passes into the hollow needle 416 via a proximal end 416A thereof for selective distal advancement past the distal end of the needle via user actuation of the slide. Distal advancement of the guidewire 422 out the distal end of the needle 416 is stopped when the guidewire bend 422A engages the needle proximal end 416A.

A catheter advancement assembly 440 is also shown for selectively advancing the catheter tube 44 over the needle 416, including a slide 448 that slides along the track 430, and a carriage 450 disposed within the housing 412 and operably connected to the slide 448. The carriage 450 is initially engaged with the catheter hub 46 such that distal sliding of the slide 448 causes the catheter to be distally advanced toward the distal housing end.

The insertion tool 410 further includes a support structure 470 for stabilizing the needle 416, including two doors 472 hingedly attached via pins to the distal end of the housing 412. The doors 472 serve to stabilize the needle 416 during insertion into the patient. Later, when the catheter tube 44 and catheter hub 46 are advanced distally by the slide 448, the doors 472 are opened, enabling the catheter 42 to pass through the doors and be separated by the user from the insertion tool 410. In the present embodiment, a wedge feature is included on the bottom surface of the slide 428, the wedge feature being configured to push the doors 472 open when the slide is slid distally, as described herein. Such a wedge or other suitable feature can be included in other embodiments described herein as well.

After separation from the insertion tool 410, the catheter 42 can then be advanced and placed as needed into the patient by the user. Note that, though none is shown, a needle safety component can be included for isolating the distal tip of the needle 416. In one embodiment, distal sliding of the guidewire slide 428 can partially open the doors 472 in preparation for catheter advancement.

Figure 28:
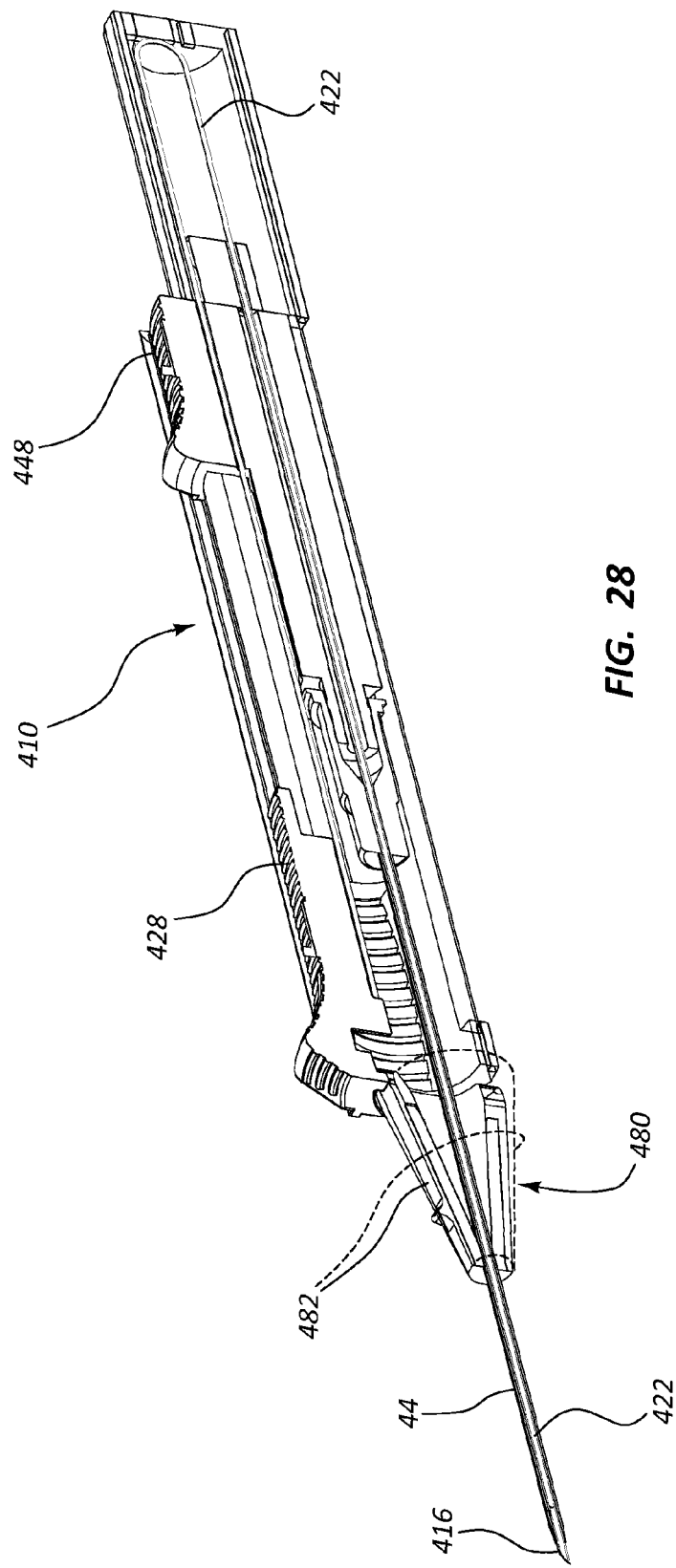
FIG. 28 is a cross sectional view of a catheter insertion tool according to one embodiment.

FIG. 28 shows the insertion tool 410 including a support structure 480 according to another embodiment, wherein two half-conically shaped doors 482 are hingedly connected to the housing 412 (via living hinges or other suitable connective scheme) and configured to stabilize the needle 416. The carriage of the insertion tool 410 in FIG. 28 is also longer relative to that of FIG. 27. Thus, it is appreciated that various different support structures and configurations can be employed for stabilizing the needle at or near its exit point from the insertion tool housing.

Reference is now made to FIGS. 29A and 29B in describing a catheter insertion tool 510 according to one embodiment. The insertion tool 510 includes a housing 512 that partially encloses the catheter 42. A hollow needle 516 distally extends from a needle hub 514 that caps a proximal end of the housing 512 such that the needle extends out the distal end of the housing 512.

A guidewire advancement assembly 520 is shown for selectively advancing a guidewire 522, including a slide 528 that slides along a track 530 defined in the housing 512. The guidewire 522 is attached to the slide 528 and extends proximally within the housing 512 and out through a pigtail 524, attached to the proximal end of the housing 512, via a top one of two holes 514A defined in the needle hub 514. Near the proximal end of the pigtail 524, the guidewire 522 bends to form a U-shaped guidewire bend 522A and distally extends back into the housing 512 to pass into the hollow needle 516 via a bottom one of the two needle hub holes 514A, for eventual distal advancement out the distal end of the needle when the slide 528 is selectively actuated by a user. Such distal advancement of the guidewire 522 out the distal end of the needle 416 is stopped when the guidewire bend 522A abuts the holes 514A defined in the needle hub 514.

A catheter advancement assembly 540 is also shown for selectively advancing the catheter tube 44 over the needle 516, including a slide 548 that slides along the track 530, and a carriage 550 disposed within the housing 512 and operably connected to the slide. The carriage 550 can be initially engaged with the catheter hub 46 such that distal sliding of the slide 548 causes the catheter to be distally advanced toward the distal housing end. In the present embodiment a bulge 522B is included on the guidewire 522 such that, when the guidewire is distally advanced by user actuation of the (guidewire advancement) slide 528, the bulge is advanced and engages an internal portion of the (catheter advancement) slide 548. This in turn causes the slide 548 to be advanced as well, resulting in distal advancement of the catheter 42. Thus, the catheter can be advanced directly via the slide 548, or indirectly via the slide 528, in one embodiment.

The insertion tool 510 further includes a support structure 570 for stabilizing the needle 516, including a plug 572 that includes a plug hole 574 defined therein through which the needle 516 extends. The plug 572 is attached via the track 530 to the slide 528 and occludes the distal end of the housing 512, thus serving to stabilize the needle 516 that passes therethrough during needle insertion into the patient. Later, when the guidewire 522 is advanced distally by the slide 528, the plug 572 also distally advances out the housing 512, thus opening the housing distal end and enabling the catheter 42 to pass therethrough. The catheter 42 can then be separated by the user from the insertion tool 510 and advanced into final position by the user. Note that, though none is shown, a needle safety component can be included for isolating the distal tip of the needle 516. Note also that after the plug 572 is removed from its initial position in the housing 512, the catheter tube 44 and needle 516, no longer being constrained by the support structure plug hole 574, can axially relocate toward the center of the housing, in one embodiment. This holds true for the embodiments of FIGS. 30 and 31 as well.

Figure 30:
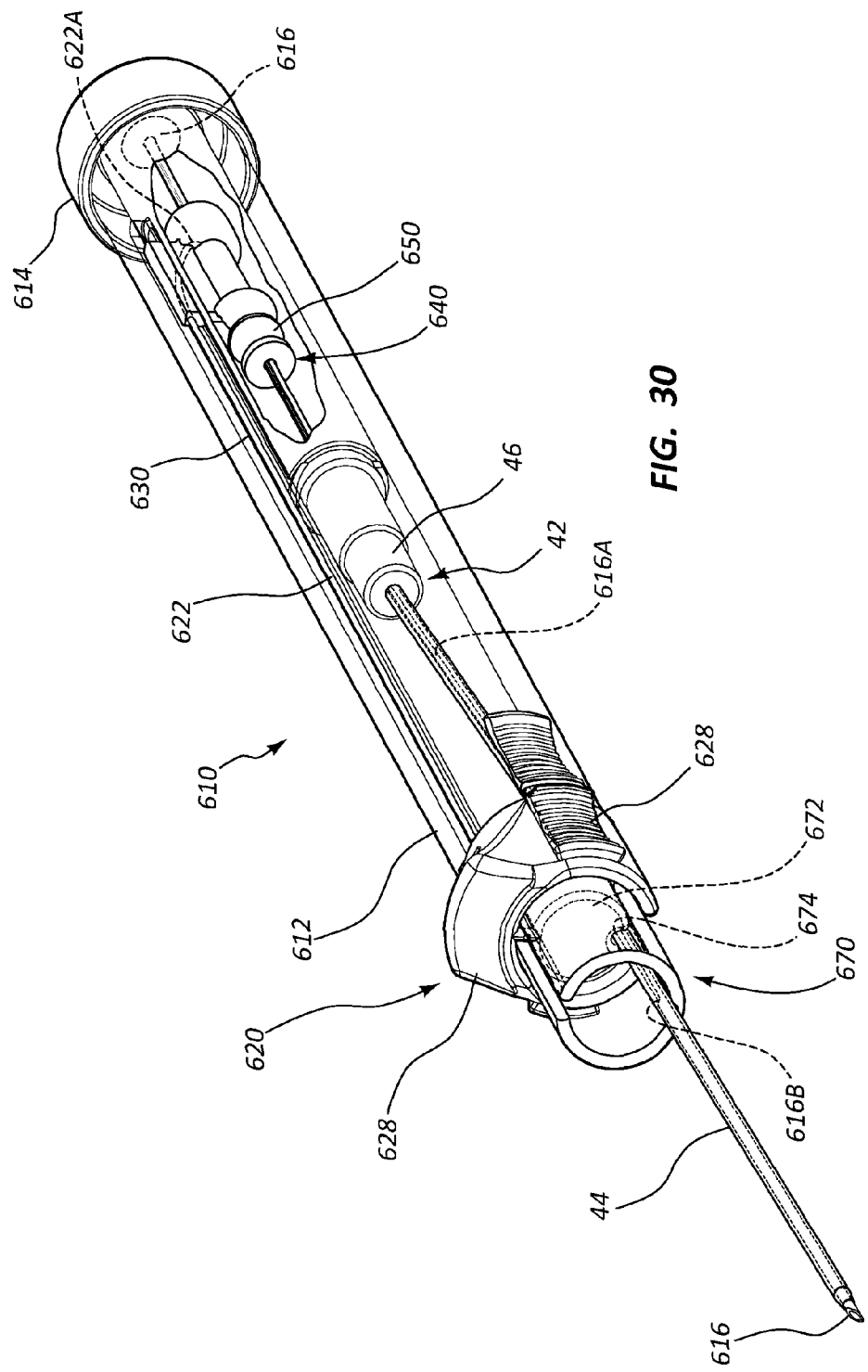
FIG. 30 is a perspective view of a catheter insertion tool according to one embodiment.

Reference is now made to FIG. 30 in describing a catheter insertion tool 610 according to one embodiment. The insertion tool 610 includes a housing 612 that partially encloses the catheter 42. A hollow needle 616 distally extends from a needle hub 614 that caps a proximal end of the housing 612 such that the needle extends out the distal end of the housing 612. The needle 616 includes a longitudinally extending proximal slot 616A that extends from the proximal end of the needle 616 to a distal end 616B of the slot.

A guidewire advancement assembly 620 is shown for selectively advancing a guidewire 622, including a slide 628 that slides along a track 630 defined in the housing 612. The guidewire 622 is attached to the slide 628 and extends proximally within the housing 612 until it bends, forming a U-shaped guidewire bend 622A, toward the distal end of the housing and passes into the hollow needle 616 via the proximal slot 616A thereof for selective distal advancement past the distal end of the needle via user actuation of the slide. Note that distal advancement of the slide 628 causes the slide to separate from the housing 612 while still being attached to the guidewire 622. Distal advancement of the guidewire 622 out the distal end of the needle 616 is stopped when the guidewire bend 622A engages the distal end 616B of the proximal slot 616A of the needle.

A catheter advancement assembly 640 is also shown for selectively advancing the catheter tube 44 over the needle 616, including a carriage 650 disposed within the housing 612 and operably connected to the slide 628 such that actuation of the slide distally advances both the guidewire 622 and the carriage 650. The carriage 650 is not initially engaged with the catheter hub 46, but engages the hub after an amount of distal advancement. This in turn causes the catheter 42 to be distally advanced toward the distal housing end.

The insertion tool 610 further includes a support structure 670 for stabilizing the needle 616, including a plug 672 that includes a plug hole 674 defined therein through which the needle 616 extends. The plug 672 is attached via the track 630 to the slide 628 and occludes the distal end of the housing 612, thus serving to stabilize the needle 616 that passes therethrough during needle insertion into the patient. Later, when the guidewire 622 is advanced distally by the slide 628, the plug 672 also distally advances out the housing 612, thus opening the housing distal end and enabling the catheter 42 to pass therethrough. The catheter 42 can then be separated by the user from the insertion tool 610 and advanced into final position by the user. Note that, in one embodiment, the carriage 650 can include a needle safety component for isolating the distal end of the needle 616.

Figure 31:
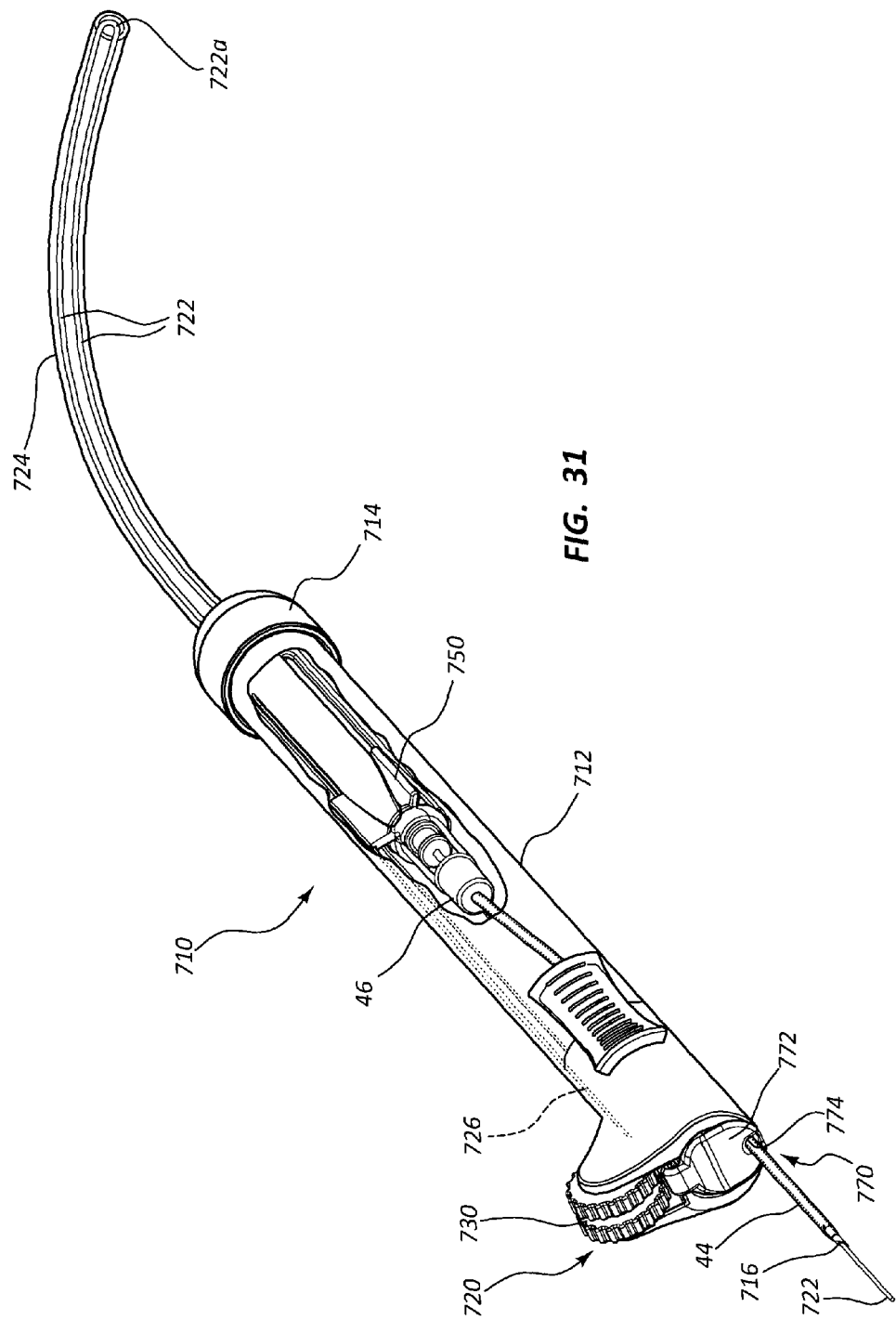
FIG. 31 is a perspective view of a catheter insertion tool according to one embodiment.

Reference is now made to FIG. 31 in describing a catheter insertion tool 710 according to one embodiment. The insertion tool 710 includes a housing 712 that partially encloses the catheter 42. A hollow needle 716 distally extends from a needle hub 714 that caps a proximal end of the housing 712 such that the needle extends out the distal end of the housing 712.

An advancement assembly 720 is shown for selectively advancing a guidewire 722 and catheter 42. The advancement assembly 720 includes a wheel 730, selectively rotatable by a user, that is attached via a filament 726 or other suitable component to a carriage 750. The guidewire 722 is attached to the carriage 750 and extends proximally within the housing 712 and out through a pigtail 724, attached to the proximal end of the housing 712, via a one of two holes defined in the needle hub 514 (similar to the holes 514A in the needle hub 514 of FIGS. 29A, 29B). Near the proximal end of the pigtail 724, the guidewire 722 bends to form a U-shaped guidewire bend 722A and distally extends back into the housing 712 to pass into the hollow needle 716 via the other of the two holes defined in the needle hub 714 for eventual distal advancement out the distal end of the needle when the wheel 730 is selectively actuated by a user. Such distal advancement of the guidewire 722 out the distal end of the needle 716 is stopped when the guidewire bend 722A abuts the above-mentioned holes defined in the needle hub 714.

The advancement assembly 720 selectively advances the catheter tube 44 over the needle 716 and includes the aforementioned carriage 750 disposed within the housing 712 and operably connected to the wheel 730 via the filament 726 such that rotation of the wheel distally advances the carriage 750. The guidewire 722, a proximal end of which being attached to the carriage 750, is also advanced distally through the needle, as described above. Note that in one embodiment the wheel 730, by virtue of the non-rigid filament 726 connecting the wheel to the carriage 750, ensures that the guidewire 722 is only distally advanced, and not proximally retractable.

Distal advancement of the carriage 750 causes the carriage—which is not initially engaged with the catheter hub 46—to engage the hub after an amount of distal advancement. This in turn causes the catheter 42 to be distally advanced toward the distal housing end.

The insertion tool 710 further includes a support structure 770 for stabilizing the needle 716, including a door 772 hingedly attached to the distal end of the housing 712 and including a hole 774 therein for enabling passage of the needle 716 therethrough. The door 772 serves to stabilize the needle 716 during insertion into the patient. Later, when the catheter tube 44 and catheter hub 46 are advanced distally by the wheel 730 and the carriage 750, the door 772 is pushed open by the hub, enabling the catheter 42 to be separated by the user from the insertion tool 710. The catheter 42 can then be advanced for final placement within the patient by the user. Note that, though none is shown, a needle safety component can be included for isolating the distal tip of the needle 716.

Reference is now made to FIGS. 32A-32I in describing a catheter insertion tool 810 according to one embodiment. The insertion tool 810 includes a housing 812 that at least partially encloses the catheter 42. A hollow needle 816 distally extends from a needle hub 814 included within the housing 812 such that the needle initially extends out the distal end of the housing 812. The needle 816 includes a distal slot 816A, similar to the previously described needle slot 226 (FIGS. 17A-17C), for enabling a guidewire/dilator 822, similar to the previously described guidewire/dilator 220 (FIG. 16) to be removably inserted therein. The catheter 42 is disposed over the guidewire/dilator 822.

The needle hub 814 further includes a needle retraction system 818 for selectively retracting the needle 816 into the housing 812 so as to isolate the distal tip of the needle from the user in a safe manner. The retraction system 818 includes a spring 819 or other suitable retraction device operably coupled to the needle 816 for effecting the needle retraction.

An advancement assembly 820 is shown for selectively advancing the guidewire/dilator 822 as well as the catheter 42. The advancement assembly 820 includes a slide 828 that travels in a track 830 defined in the housing 812. The slide 828 is operably attached to a ratchet bar 824 slidably disposed within the housing 812. The ratchet bar 824 includes a plurality of upper teeth 826 for selective catheter advancement, and at least one lower tooth 826A for actuating a retraction trigger 880 of the needle retraction system 818, as will be described. The hub 46 of the catheter 42 disposed within the housing 812 has removably attached thereto a cap 834 including a prong 836 for engaging the upper teeth 826 of the ratchet bar 824.

The insertion tool 810 further includes a support structure 870 for stabilizing the needle 816, including a housing hole 872 defined by the distal end of the housing 812. The housing hole 872 is sized to provide stability to the needle 816 at its point of exit from the housing.

Figure 32I:
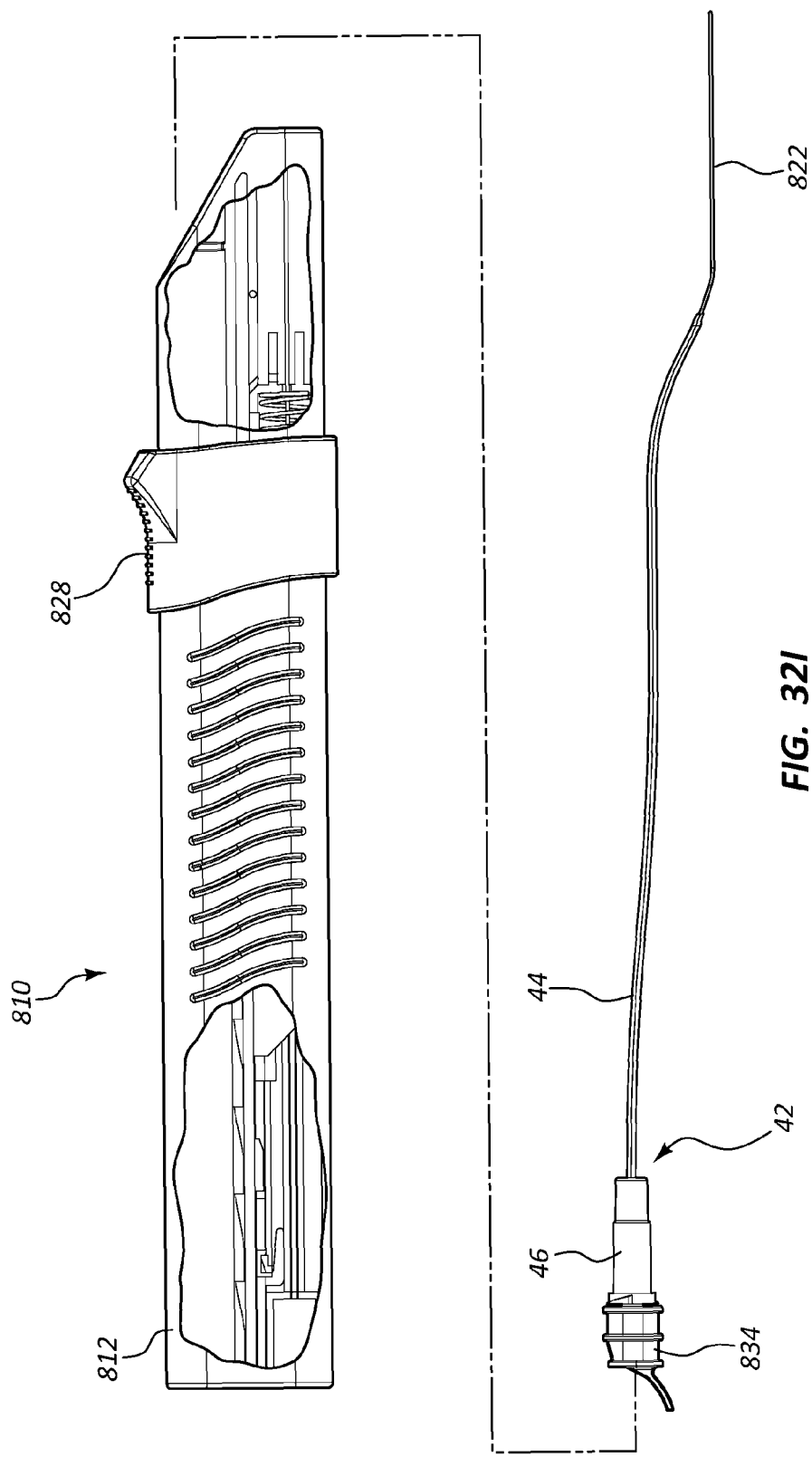

FIGS. 32A-32I depict various stages of use of the insertion tool 810 in inserting a catheter into a patient. With the insertion tool 810 in the configuration shown in FIG. 32A, vascular access is achieved with the needle 816 via user insertion of the needle into the patient at an insertion site. Blood flashback can be observed via the distal slot 816A of the needle 816 to confirm proper positioning of the distal end of the needle within the patient's vessel. As shown in FIG. 32B, the slide 828 is slid distally to advance the guidewire/dilator 822, a distal portion of which is pre-disposed within the needle 816 via the distal slot 816A, distally out the distal end of the needle and into the vessel of the patient. As shown, the guidewire/dilator 822 is advanced indirectly by the ratchet bar 824, which is moved by the slide 828. In particular, a proximate one of the upper teeth 826 of the ratchet bar 824 engages the prong 836 of the cap 834 fitted over the catheter hub 46. Thus, when the slide 828 and ratchet bar 824 are moved distally, the catheter 42 and guidewire/dilator 822 disposed therein are also moved distally, as shown in FIG. 32B. Similar ratcheting movement occurs in the successive steps as well.

Sliding of the slide 828 in the stage shown in FIG. 32B also causes the bottom tooth 826A of the ratchet bar 824 to engage the retraction trigger 880 of the needle retraction system 818. This in turn enables the spring 819 to expand and retract the needle 816 and retraction system 818 into the housing 812 such that the distal tip of the needle is isolated from the user within the housing.

FIG. 32C shows the return of the slide 828 to its initial position, which causes the ratchet bar 824 to also return to its initial position. Because the prong 836 of the cap 834 attached to the catheter hub 46 is distally angled, however, the teeth 826 of the ratchet bar slide past without retracting the catheter 42 such that the catheter remains in position.

In FIG. 32D, the slide 828 is again distally advanced, which causes a proximate upper tooth 826 of the ratchet bar 824 to engage the cap prong 836 and further advance the guidewire/dilator 822 distally into the vessel. As it is disposed over the guidewire/dilator 822, the catheter 42 at this or a successive stage is also advanced into the vessel, depending on catheter length, distance to insertion site, etc. The slide 828 is subsequently retracted to its initial position, as shown in FIG. 32E. Note that ratchet retraction can be user activated or automatically activated by a suitable system included in the insertion tool 810.

In FIG. 32F, the slide 828 and ratchet bar 824 are again distally advanced, resulting in further distal advancement out of the housing 812 of the guidewire/dilator 822 and catheter 42. The slide 828 is subsequently retracted to its initial position, as shown in FIG. 32G. In FIG. 32H, the slide 828 and ratchet bar 824 are distally advanced a final time, resulting in near-complete distal advancement of the guidewire/dilator 822 and attached catheter 42 from the housing 812 of the insertion tool 810. At this stage, the hub 46 of the catheter 42 can be grasped and the catheter removed from the insertion tool 810, which can then be discarded. Final positioning of the catheter 43 within the vessel can then be manually performed by the user. The cap 834 is also removed from the catheter hub 46.

Figure 33A:
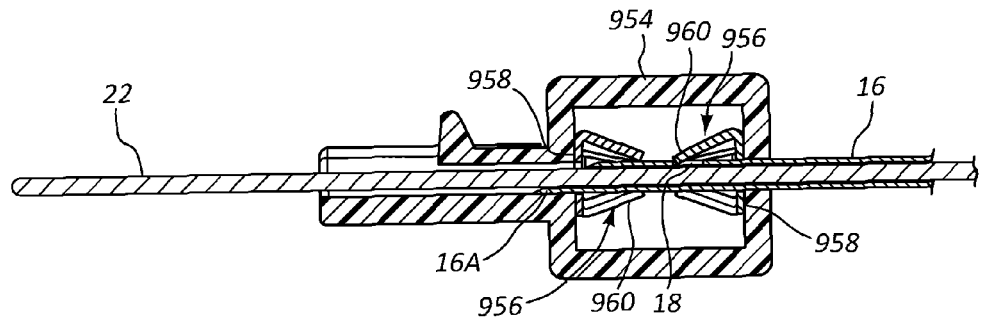
FIGS. 33A-33C are various views of a safety needle component according to one embodiment.
Figure 33B:
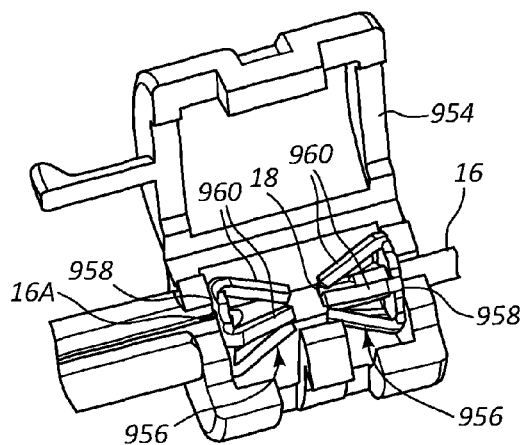
Figure 33C:
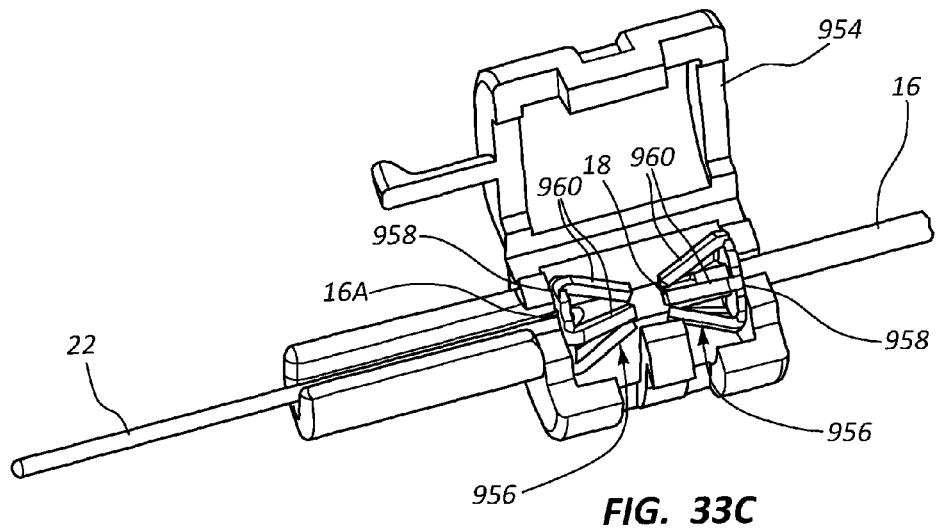

FIGS. 33A-33C depict details of a needle safety component for isolating the distal end 16A of the needle 16, the needle including the distal notch 18 as discussed above in connection with FIGS. 1A-10C, according to one embodiment. As shown, a safety housing 954 including a hinged door is included so as to ride over the needle 16. Two needle safety components 956 are oppositely disposed within the safety housing 954 and each also rides over the needle 16. Each needle safety component includes a base 958 defining a hole through which the needle 16 passes and a plurality of arms 960. The arms 960 extend from the base 958 and converge toward one another in conical fashion such that an end of each arm abuts the needle surface. The arms 960 are configured to engage the notch 18 defined in the distal portion of the needle 16 and prevent further movement of the needle 16 with respect to the needle safety component 956. In particular, each arm 960 compressively engages the outer surface of the needle 16 such that when one of the arms encounters the needle notch 18, the arm will descend into the notch slightly so as to lock the needle 16 in place with respect to the needle safety component 956. Two needle safety components 956 are disposed in the safety housing 954 so as to prevent further needle movement in either direction, distally or proximally. Thus, the distal end 16A of the needle 16 is safely isolated within the safety housing 954, as seen in FIGS. 33A-33C. Note that the needle safety component described here is useful for isolating a needle even when the guidewire 22 still extends therethrough, as seen in FIG. 33C, for example.

In other embodiments, only one needle safety component as described above may be used. Thus, the needle safety component described here serves as one example of a variety of needle safety components that may be employed in connection with the present disclosure.

It is appreciated that in one embodiment the insertion tool can include a sterile sheath or bag that is disposed over a distal portion of the catheter that distally extends from the insertion tool housing so as to isolate the catheter. The needle, pre-disposed within the catheter and retractable into the insertion tool housing, can extend from the bag to gain vascular access. Thereafter, the bag can be compressed toward the housing as the catheter is advanced into the vasculature, then disposed of once the catheter is fully inserted. In one embodiment, the bag can include a grip wing or other device that helps to grasp the catheter or needle through the bag during insertion. Further note that the insertion tools described herein can include a cap or other protective device that is removably attached to the insertion tool before use so as to preserve the sterility of the needle and catheter.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. An insertion tool for inserting a catheter into a body of a patient, comprising:
   a housing;
   a needle having a proximal portion in the housing and a distal portion extending from a distal end of the housing;
   a catheter advancement assembly, comprising:
   the catheter coaxially disposed over the needle, the catheter having a proximal end in the housing and a distal end extending from the distal end of the housing in a catheter first position; and
   a handle coupled to the proximal end of the catheter, the handle extending laterally from the housing in the catheter first position, the handle slidable with respect to the housing to transition the catheter distally from the catheter first position to a catheter second position; and
   a guidewire advancement assembly, comprising:
   a guidewire disposed at least partially in a lumen of the needle; and
   a slide member coupled to the guidewire, the slide member slidable with respect to the housing to transition the guidewire relative to the needle.

2. The insertion tool according to claim 1, wherein a proximal end of the needle is attached to a needle hub, the needle hub coupled to the housing.

3. The insertion tool according to claim 1, wherein the catheter advancement assembly further comprises a catheter hub coupled to the proximal end of the catheter, the catheter hub releasably coupled to the handle.

4. The insertion tool according to claim 1, wherein the handle is designed to separate from the housing in the catheter second position.

5. The insertion tool according to claim 1, wherein the housing includes a first housing portion and a second housing portion held together by the slide member in a guidewire first position.

6. The insertion tool according to claim 5, wherein the slide member releases at least one of the first housing portion and the second housing portion in a guidewire second position distal to the guidewire first position, thereby enabling movement of the handle out of the housing during transition of the catheter from the catheter first position to the catheter second position.

7. The insertion tool according to claim 6, further comprising a lock out component that prevents movement of the guidewire from the guidewire second position to the guidewire first position.

8. The insertion tool according to claim 6, wherein the slide member engages a portion of the needle in the guidewire second position to prevent further distal advancement of the guidewire.

9. The insertion tool according to claim 1, wherein the catheter advancement assembly further comprises a needle safety component designed to capture a tip of the needle therein, the needle safety component releasably coupled to the handle.

10. The insertion tool according to claim 1, further comprising a needle support structure including at least one of a portion of the housing, a component hingedly connected to the housing, and a removable plug.

11. The insertion tool according to claim 10, wherein the needle support structure includes an interface defined by the distal end of the housing.

12. The insertion tool according to claim 1, wherein the needle includes a notch proximate a distal end thereof to enable observation of blood flashback.

13. The insertion tool according to claim 1, wherein the handle further comprises a blood control valve.

* * * * *